(12) United States Patent
Simon et al.

(10) Patent No.: US 11,098,342 B2
(45) Date of Patent: Aug. 24, 2021

(54) TIME LAPSE SEQUENCING: A CONVERTIBLE-NUCLEOSIDE APPROACH TO ENRICHMENT-FREE ANALYSIS OF RNA DYNAMICS

(71) Applicant: Yale University, New Haven, CT (US)

(72) Inventors: Matthew Simon, New Haven, CT (US); Jeremy Schofield, New Haven, CT (US)

(73) Assignee: Yale University, New Haven, CT (US)

( * ) Notice: Subject to any disclaimer, the term of this patent is extended or adjusted under 35 U.S.C. 154(b) by 380 days.

(21) Appl. No.: 15/941,323

(22) Filed: Mar. 30, 2018

(65) Prior Publication Data
US 2018/0282789 A1    Oct. 4, 2018

Related U.S. Application Data

(60) Provisional application No. 62/479,858, filed on Mar. 31, 2017.

(51) Int. Cl.
*C12Q 1/68*    (2018.01)
*C12Q 1/6806*    (2018.01)
*C12Q 1/6869*    (2018.01)

(52) U.S. Cl.
CPC ......... *C12Q 1/6806* (2013.01); *C12Q 1/6869* (2013.01)

(58) Field of Classification Search
CPC .................. C12Q 1/6869; C12Q 1/6806
See application file for complete search history.

(56) References Cited

PUBLICATIONS

Allerson et al., 1997, "A chemical method for site-specific modification of RNA: the convertible nucleoside approach," J Am Chem Soc, 119:7423-7433.
Bhatt et al., 2012, "Transcript dynamics of proinflammatory genes revealed by sequence analysis of subcellular RNA fractions," Cell, 150:279-290.
Churchman and Weissman, 2011, "Nascent transcript sequencing visualizes transcription at nucleotide resolution," Nature, 469:368-373.
Derman et al., 1981, "Transcriptional control in the production of liver-specific mRNAs," Cell, 23:731-739.
Duffy et al., (2015) "Tracking distinct RNA populations using efficient and reversible covalent chemistry," Mol Cell, 59:858-866.
Friedel et al., (2009) "Conserved Principles of Mammalian Transcriptional Regulation Revealed by RNA Half-Life," Nucleic Acids Res. 37:e115. (12 pages).
Frommer et al., 1992, "A genomic sequencing protocol that yields a positive display of 5-methylcytosine residues in individual DNA strands," Proc Natl Acad Sci U.S.A., 89:1827-1831.
Gaidatzis et al., 2015, "Analysis of intronic and exonic reads in RNA-seq data characterizes transcriptional and post-transcriptional regulation," Nat Biotechnol, 33:722-729.

(Continued)

*Primary Examiner* — Jezia Riley
(74) *Attorney, Agent, or Firm* — Riverside Law LLP

(57) ABSTRACT

The invention provides methods and compositions for generating mutations in new nucleic acid molecules through incorporation of a transformable nucleoside into the nucleic acid and subsequent transformation of the nucleoside through oxidative-nucleophilic-aromatic-substitution chemistry, referred to as TimeLapse chemistry. The invention further provides methods for detecting the mutations, referred to as TimeLapse-seq.

9 Claims, 33 Drawing Sheets

Specification includes a Sequence Listing.

(56) References Cited

PUBLICATIONS

Gelsi-Boyer et al., (2009) "Mutations of Polycomb-Associated Gene ASXL1 in Myelodysplastic Syndromes and Chronic Myelomonocytic Leukaemia," Br. J. Haematol. 145:788-800.

Hafner et al., 2010, "Transcriptome-wide identification of RNA-binding protein and microRNA target sites by PAR-CLIP," Cell, 141:129-141.

Harris et al., 1991, "New strategy for the synthesis of oligodeoxynucleotides bearing adducts at exocyclic amino sites of purine nucleosides," J Am Chem Soc, 113:4328-4329.

Hayatsu et al., 1970, "Reaction of sodium bisulfite with uracil, cytosine, and their derivatives," Biochemistry, 9:2858-2865.

Herzog et al., (2017) "Thiol-linked Alkylation of RNA to Assess Expression Dynamics," Nat. Methods 14:1198-1204.

Kwak et al., 2013, "Precise maps of RNA polymerase reveal how promoters direct initiation and pausing," Science, 339:950-953.

MacMillan and Verdine, "Synthesis of functionally tethered oligodeoxynucleotides by the convertible nucleoside approach," 1990, J Org Chem, 55:5931-5933.

Mahat et al., 2016, "Mammalian heat shock response and mechanisms underlying its genome-wide transcriptional regulation," Mol Cell, 62:63-78.

Menet et al., 2012, "Nascent-Seq reveals novel features of mouse circadian transcriptional regulation," Elife, 1:e00011. (25 pages).

Mishima and Steitz, 1995, "Site☐specific crosslinking of 4☐thiouridine☐modified human tRNA (3Lys) to reverse transcriptase from human immunodeficiency virus type I," Embo J, 14:2679-2687.

Moore and Sharp, 1992, "Site-specific modification of pre-mRNA: the 2'-hydroxyl groups at the splice sites," Science, 256:992-997.

Mukherjee et al., 2017, "Integrative classification of human coding and noncoding genes through RNA metabolism profiles," Nat Struct Mol Biol, 24:86-96.

Pandey and Marzluff, 1987, "The Stem-Loop Structure at the 3' End of Histone mRNA is Necessary and Sufficient for Regulation of Histone mRNA Stability," Cell Biol, 7:4557-4559.

Rabani et al., 2011, "Metabolic labeling of RNA uncovers principles of RNA production and degradation dynamics in mammalian cells," Nat Biotechnol, 29:436-442.

Rabani et al., 2014, "High-resolution sequencing and modeling identifies distinct dynamic RNA regulatory strategies," Cell, 159:1698-1710.

Russo et al., (2017) "Metabolic Labeling and Recovery of Nascent RNA to Accurately Quantify mRNA Stability," Methods, 120:39-48.

Saladino et al., 1996, "Transformations of thiopyrimidine and thiopurine nucleosides following oxidation with dimethyldioxirane," Tetrahedron, 52:6759-6780.

Schwalb et al., (2016) "TT-seq maps the human transient transcriptome," Science, 352:1225-1228.

Schwanhäusser et al., (2011) "Global quantification of mammalian gene expression control," Nature 473, 337-342.

Shalgi et al., 2014, "Widespread inhibition of posttranscriptional splicing shapes the cellular transcriptome following heat shock," Cell Rep, 7:1362-1370.

Siegfried et al., 2014, "RNA motif discovery by SHAPE and mutational profiling (SHAPE-MaP)," Nat Methods, 11:959-965.

Sittman et al., 1983, "Histone mRNA concentrations are regulated at the level of transcription and mRNA degradation," Proc Natl Acad Sci U.S.A., 80:1849-1853.

Trinklein et al., 2004, "The role of heat shock transcription factor 1 in the genome-wide regulation of the mammalian heat shock response," Mol Biol Cell, 15:1254-1261.

Wada et al., 2009, "A wave of nascent transcription on activated human genes," Proc natl Acad Sci U.S.A., 106:18357-18361.

Yano and Hayatsu, 1970, "Permanganate oxidation of 4-thiouracil derivatives: Isolation and properties of 1-substituted 2-pyrimidone 4-sulfonates," Biochim Biophys Acta, 199:303-315.

Ziff and Fresco, 1969, "Locating 4-thiouridylate in the primary structure of transfer ribonucleic acids," Biochemistry, 8:3242-3248.

| Sample | HS-1 | HS-2 | no chem | no s⁴U | NHS-1 | NHS-2 |
|---|---|---|---|---|---|---|
| Heat shock | + | + | + | + | - | - |
| s⁴U treatment | + | + | + | - | + | + |
| TimeLapse chemistry | + | + | - | + | + | + |
| Number of input reads | 320373354 | 300303654 | 356893452 | 372226112 | 378220537 | 482848580 |
| Average input read length | 187 | 188 | 189 | 188 | 188 | 187 |
| Uniquely mapped reads number | 103020233 | 107067334 | 123530686 | 120135447 | 125345776 | 154004462 |
| Mismatch rate per base, % | 1.53% | 1.52% | 1.45% | 1.48% | 1.52% | 1.57% |
| Deletion rate per base | 0.08% | 0.08% | 0.04% | 0.10% | 0.08% | 0.11% |
| Deletion average length | 1.84 | 1.86 | 2.13 | 1.8 | 1.79 | 1.75 |
| Insertion rate per base | 0.06% | 0.07% | 0.05% | 0.08% | 0.06% | 0.07% |
| Insertion average length | 2.11 | 2.15 | 2.35 | 2.04 | 1.85 | 1.87 |
| Reads mapped to multiple loci | 12722801 | 14224326 | 16532208 | 16870001 | 17378285 | 24111157 |
| % of reads mapped to multiple loci | 3.86% | 4.59% | 4.63% | 4.53% | 4.59% | 4.99% |
| Reads mapped to too many loci | 1062234 | 963376 | 1013113 | 1556313 | 1467386 | 2104411 |
| % of reads mapped to too many loci | 0.32% | 0.31% | 0.28% | 0.42% | 0.39% | 0.45% |
| % of reads unmapped: too many mismatches | 1.15% | 1.16% | 0.90% | 1.01% | 1.10% | 1.34% |
| % of reads unmapped: too short | 62.59% | 58.58% | 58.96% | 60.74% | 59.90% | 60.17% |
| % of reads unmapped: other | 0.79% | 0.62% | 0.60% | 1.02% | 0.85% | 1.16% |

Figure 29

TIME LAPSE SEQUENCING: A CONVERTIBLE-NUCLEOSIDE APPROACH TO ENRICHMENT-FREE ANALYSIS OF RNA DYNAMICS

CROSS REFERENCE TO RELATED APPLICATIONS

This application claims priority to U.S. Provisional Application No. 62/479,858, filed Mar. 31, 2017 which is hereby incorporated by reference herein in its entirety.

STATEMENT REGARDING FEDERALLY SPONSORED RESEARCH OR DEVELOPMENT

This invention was made with government support under HD083992 and GM007223 awarded by the National Institutes of Health (NIH). The government has certain rights in the invention.

BACKGROUND OF THE INVENTION

Regulated changes in cellular RNA populations are inherent to dynamic biological systems. RNA content can be analyzed by RNA-sequencing (RNA-seq), which captures the biological state at the time the sample was harvested, but fails to capture the rich dynamics of the transcriptome. Unlike non-invasive methods such as microscopy, RNA-seq does not offer temporal information because the sample is destroyed when making a sequencing library. While these dynamics are not captured in a traditional RNA-seq experiment, rapid changes in regulated transcription have been observed by examining sites of active RNA polymerase II through biochemical enrichment of transcripts that are in the process of being synthesized (e.g., nuclear run-on (Derman et al., 1981, Cell, 23:731-739) by PRO-seq (Kwak et al., 2013, Science, 339:950-953) and NET-seq (Churchman and Weissman, 2011, Nature, 469:368-373). In mammals, transcriptional dynamics on the timescale of minutes to hours have been observed for circadian rhythms (Menet et al., 2012, Elife, 1:e00011) and the immune response through identifying new transcripts that co-fractionate with chromatin (Bhatt et al., 2012, Cell, 150:279-290), or by examining unspliced transcripts that still contain introns (Wada et al., 2009, Proc natl Acad Sci U.S.A., 106:18357-18361; Gaidatzis et al., 2015, Nat Biotechnol, 33:722-729). Metabolic labeling and enrichment of new transcripts has been used to construct kinetic models of distinct transcript populations (Rabani et al., 2011, Nat Biotechnol, 29:436-442) and to classify transcripts including non-coding RNAs (Mukherjee et al., 2017, Nat Struct Mol Biol, 24:86-96).

Thus, there is a need in the art for a method to provide temporal information about the sequenced RNA to provide a more detailed portrait of the biological state of a sample. The current invention satisfies this need.

SUMMARY OF THE INVENTION

In one embodiment, the invention relates to a method for generating mutations in amplification products derived from newly synthesized nucleic acid molecules comprising: a) contacting a cell with a thiol-containing nucleoside, wherein the thiol-containing nucleoside is incorporated into at least one newly synthesized nucleic acid molecule; b) isolating the nucleic acid molecules from the cell; c) contacting the isolated nucleic acid molecules with an oxidant and a nucleophile, thereby converting the modified base to an analog of a different base; and d) amplifying the isolated nucleic acid molecules.

In one embodiment, the oxidant is hydrogen peroxide ($H_2O_2$), sodium iodate ($NaIO_3$), potassium permagnate ($KMnO_4$), sodium periodate ($NaIO_4$), or meta-Chloroperoxybenzoic acid (mCPBA).

In one embodiment, the nucleophile is 2,2,2-trifluoroethylamine (TFEA), benzylamine ($C_6H_5CH_2NH_2$), O-methylhydroxylamine hydrochloride ($MeONH_2$), aniline ($C_6H_5NH_2$), hydrazine ($H_2NNH_2$), ammonia ($NH_3$), 1,1-dimethylethylenediamine ($(CH_3)_2NCH_2CH_2NH_2$), methylamine ($CH_3NH_2$), propargylamine ($HCCCH_2NH_2$), allylamine ($H_2CCHCH_2NH_2$), 2-azidoethylamine ($N_3CH_2CH_2NH_2$), cysteiamine disulfide ($(HSCH_2CH_2S)_2$), or 4-(Trifluoromethyl)benzylamine ($CF_3C_6H_4CH_2NH_2$).

In one embodiment, the oxidant is $NaIO_4$ and the nucleophile is TFEA.

In one embodiment, the nucleic acid molecule is a ribonucleic acid molecule. In one embodiment, the thiol-containing nucleoside is 4-thiouridine ($s^4U$), 6-thioguanine ($s^6G$), or 6-thiodeoxyguanosine ($s^6dG$).

In one embodiment, the thiol-containing nucleoside comprises $s^4U$ and the thiol-containing nucleoside is converted into an analog of cytidine. In one embodiment, the mutation is a U to C mutation.

In one embodiment, the thiol-containing nucleoside is $s^6G$ or $s^6dG$, and the thiol-containing nucleoside is converted into an analog of adenine. In one embodiment, the mutation is a G to A mutation.

In one embodiment, the nucleic acid molecule is a deoxyribonucleic acid molecule. In one embodiment, the thiol-containing nucleoside is 4-thiothymine ($s^4T$), $s^6G$ or $s^6dG$.

In one embodiment, the thiol-containing nucleoside comprises $s^4T$ and the thiol-containing nucleoside is converted into an analog of cytidine. In one embodiment, the mutation is a U to C mutation.

In one embodiment, the thiol-containing nucleoside is $s^6G$ or $s^6dG$, and the thiol-containing nucleoside is converted into an analog of adenine. In one embodiment, the mutation is a G to A mutation.

In one embodiment, the invention relates to a method for identifying newly synthesized nucleic acid molecules comprising: a) contacting a cell with a modified base, wherein the modified base is incorporated into at least one newly generated nucleic acid molecule; b) isolating the nucleic acid molecules from the cell; c) contacting the isolated nucleic acid molecules with an oxidant and a nucleophile, wherein the modified base is converted to an analog of a different base; d) detecting the presence of the analog of a different base or a mutation that is the result of amplification thereof; and e) identifying a nucleic acid molecule comprising the analog of a different base as being a newly generated nucleic acid molecule.

In one embodiment, the oxidant is $H_2O_2$, $NaIO_3$, $KMnO_4$, $NaIO_4$, or mCPBA.

In one embodiment, the nucleophile is TFEA, benzylamine, $MeONH_2$, aniline, hydrazine, ammonia, 1,1-dimethylethylenediamine, methylamine, propargylamine, allylamine, 2-azidoethylamine, cysteiamine disulfide or 4-(Trifluoromethyl)benzylamine.

In one embodiment, the oxidant is $NaIO_4$ and the nucleophile is TFEA.

In one embodiment, the nucleic acid molecule is a ribonucleic acid molecule. In one embodiment, the thiol-containing nucleoside is $s^4U$, $s^6G$, or $s^6dG$.

In one embodiment, the thiol-containing nucleoside comprises $s^4U$ and the thiol-containing nucleoside is converted into an analog of cytidine. In one embodiment, the mutation is a U to C mutation.

In one embodiment, the thiol-containing nucleoside is $s^6G$ or $s^6dG$, and the thiol-containing nucleoside is converted into an analog of adenine. In one embodiment, the mutation is a G to A mutation.

In one embodiment, the nucleic acid molecule is a deoxyribonucleic acid molecule. In one embodiment, the thiol-containing nucleoside is $s^4T$, $s^6G$ or $s^6dG$.

In one embodiment, the thiol-containing nucleoside comprises $s^4T$ and the thiol-containing nucleoside is converted into an analog of cytidine. In one embodiment, the mutation is a U to C mutation.

In one embodiment, the thiol-containing nucleoside is $s^6G$ or $s^6dG$, and the thiol-containing nucleoside is converted into an analog of adenine. In one embodiment, the mutation is a G to A mutation.

In one embodiment, the step of detecting comprises sequencing the nucleic acid molecules.

In one embodiment the invention relates to a kit for use in a method of generating mutations in amplification products derived from newly synthesized nucleic acid molecules comprising at least one of: a) a thiol-containing nucleoside; b) an oxidant; and c) a nucleophile.

In one embodiment the kit comprises a thiol-containing nucleoside, an oxidant and a nucleophile. In one embodiment the thiol-containing nucleoside is $s^4U$, the oxidant is $NaIO_4$ and the nucleophile is TFEA.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIG. 1, comprising FIG. 1A depicts a schematic diagram of TimeLapse-seq. New metabolically labeled RNAs are isolated and treated with TimeLapse chemistry, converting 4-thiouridine ($s^4U$) into a modified cytosine (C*) that is identified through increased numbers of T-to-C mutations upon sequencing (increasingly shaded.) FIG. 1B depicts experimental results demonstrating that $s^4U$ can be transformed into a convertible nucleoside intermediate through oxidation, which is then converted to C* through aminolysis. Below, LC-MS extracted ion chromatograms show the disappearance of $s^4U$ (front line) and the appearance of a product with the expected mass of C* (back line). FIG. 1C depicts a schematic diagram of the restriction enzyme assay used to optimize TimeLapse chemistry. FIG. 1D depicts experimental results from the restriction enzyme assay using optimized TimeLapse chemistry conditions. FIG. 1E depicts experimental results demonstrating that both oxidant and amine are necessary for TimeLapse chemistry. FIG. 1F depicts experimental results demonstrating LC-MS extracted ion chromatograms for $s^4U$ (front trace) and a product (back trace) with the expected mass of C* following TimeLapse chemistry. FIG. 1G depicts experimental results demonstrating 1H NMR spectra 4-thiouracil with (top) and without (bottom) TimeLapse chemistry with integrations displayed below peaks. Peaks are tentatively assigned to the structures displayed (left). Peaks corresponding to amide protons are shifted downfield and are not shown in above view. *Multiplet assigned to excess TFEA. FIG. 1H depicts experimental results demonstrating a primer extension assay measuring the efficiency of reverse transcriptase (RT) read-through on an IVT RNA. $s^4U$-containing IVT RNA was treated with 600 mM TFEA and 10 mM $NaIO_4$ for 1 hour at 45° C., followed by reverse transcription with a Cy5-labeled RT primer. With chemical treatment, the RT efficiently reads through a majority (>98%) of chemical adducts, consistent with transcriptome-wide TimeLapse-seq data. FIG. 1I depicts experimental results demonstrating the rate of chemistry induced read lost for slow (fraction new=0-0.33), middle (fraction new=0.34-0.66), and fast (fraction new=0.67-1) turnover transcripts from MEF cells treated with 1 mM $s^4U$ for 1 hour followed by TimeLapse-seq.

FIG. 3, comprising FIG. 7A depicts a schematic diagram of the reaction scheme. FIG. 7B depicts the results of example experiments demonstrating data from LC-MS extracted ion chromatograms (EICs) of G and 8-oxoG 50 μM standards, compared to EICs of G and 8-oxoG after incubating G under the indicated conditions. FIG. 7C depicts the results of example experiments demonstrating transcriptome-wide G-to-T and T-to-C mutation rates for replicate samples with or without TimeLapse chemistry (Chem) and $s^4U$ treatment ($s^4U$). FIG. 7D depicts the results of example experiments demonstrating representative browser shots of the Myc transcript displaying a high degree of T-to-C mutations with TimeLapse chemistry and $s^4U$, and levels of G-to-T mutations comparable to background levels of T-to-C mutations. FIG. 3E depicts a schematic diagram of the reaction showing the resultant desired oxidative nucleophilic aromatic substitution reaction, and also the oxidation of the vicinal diol of the nucleoside leading to the product shown here in addition to dehydration products. In an intact RNA, this reaction will only happen at unphosphorylated 3'-termini, and is not expected to adversely influence TimeLapse-seq. FIG. 3F depicts the results of example experiments demonstrating an LC-MS analysis of a reaction as shown in FIG. 3E.

FIG. 4, comprising FIG. 4A depicts the results of example experiments demonstrating an analysis of the effect of different nucleophiles on TimeLapse chemistry. $s^4U$-containing IVT RNA ($s^4U$ RNA, Table 1) was treated with indicated amine (600 mM) and $NaIO_4$ (10 mM) in 1.5 M sodium acetate pH 5.2 for 1 h at 45° C. and analyzed using a NotI digestion assay. Treatment with 2,2,2-trifluoroethylamine (TFEA) consistently results in a high degree (~80%) of digestion. FIG. 4B depicts the results of example experiments demonstrating an analysis of the effect of different oxidants. $s^4U$ RNA (50 µM) was treated with indicted oxidant (10 mM) and TFEA in 100 mM sodium acetate pH 5.2 for 1 h at 45° C. FIG. 4C depicts the results of example experiments demonstrating an analysis of different reaction times and temperatures. $s^4U$ RNA was incubated with indicated conditions in 100 mM sodium acetate pH 5.2. FIG. 4D depicts the results of example experiments demonstrating the results from the restriction enzyme assay indicating efficient (~80%) T-to-C* conversion with optimized TimeLapse chemistry (left: 600 mM TFEA, 10 mM $NaIO_4$, 1 hour, 45° C.), and quantification of replicate assays (right, +$s^4U$ and +TimeLapse chemistry normalized average efficiency=86%, n=4). *Conversion efficiency was not calculated for panel A so instead values without normalization are provided.

FIG. 5, comprising FIG. 5A depicts a schematic of targeted TimeLapse-seq. Mouse cells were treated with 700 µM $s^4U$ for 2 hours, followed by RNA isolation, TimeLapse chemistry, reverse transcription with Actb and Gapdh specific primers (Table 2), cDNA amplification and sequencing. Targeted sequencing reads were analyzed for rates of mutation to C. FIG. 5B depicts correlation plots of raw N-to-C mutation frequencies in targeted TimeLapse-seq with and without $s^4U$ or chemistry. FIG. 5C depicts the results of example experiments demonstrating the cumulative distribution of normalized N-to-C mutation frequencies in RNAs from $s^4U$ treated cells, with and without TimeLapse chemistry. FIG. 5D depicts exemplary replicate barplots of normalized N-to-C mutation frequencies for selected regions of Actb and Gapdh mRNAs from $s^4U$ treated cells with and without TimeLapse chemistry treatment. Annotated U nucleotides generally display higher T-to-C mutation frequencies in a TimeLapse chemistry-dependent treatment. Biological replicates display a high degree of similarity in T-to-C mutation frequencies. FIG. 5E depicts an exemplary barplot of normalized mutation frequencies from targeted TimeLapse-seq of the MYC transcript for 1 hour $s^4U$ treatment in K562 cells.

FIG. 9, comprising FIG. 9A depicts exemplary MEF cell viability assays with increasing concentrations of $s^4U$ (0, 50, 100, 500 and 1000 µM). FIG. 9B depicts exemplary MEF cell viability assays with increasing concentrations of Triton-X-100 (0, 0.5, 1, and 2%). MEF cells were plated at $10^6$ cells/ml and allowed to rest overnight. An MTT assay (ATTC MTT Cell Proliferation Assay kit) was performed in triplicate after indicated treatment for 1 h. After treatment and lysis, absorbance at 570 nm was measured. FIG. 9C depicts an exemplary MA-plot of expression levels in RNA-seq in MEF cells treated with 1 mM $s^4U$ for 1 hour, compared to cells without $s^4U$ treatment. FIG. 9D depicts exemplary correlation plots demonstrating high correspondence between the transcript-level read counts for all controls. Image shows correlation values for the log10 transformed read counts of all transcripts with greater than one read per sample (n=10422). Bottom left shows plotted data points, and in the upper right is the Pearson's r correlation value. Each condition was tested with two replicates. Conditions are: ++, with $s^4U$ treatment and chemical treatment; +–, with $s^4U$ treatment but no chemical treatment; –+, no $s^4U$ treatment but with chemical treatment; ––, neither $s^4U$ treatment nor chemical treatment.

FIG. 11, comprising FIG. 11A and FIG. 11B depict exemplary correlation analysis of the number of RNA-seq counts and number of T-to-C mutations found in each transcript between replicates treated with TimeLapse chemistry. FIG. 11C and FIG. 11D depict exemplary correlation analysis of the number of RNA-seq counts and number of T-to-C mutations found in each transcript between replicates of samples from cells subjected to heat shock. FIG. 11E and FIG. 11F depict exemplary correlation analysis of inferred new read count for each transcript between replicates subjected to TimeLapse chemistry with heat shock or without heat shock, determined by the fraction new analysis described in methods.

FIG. 12, comprising FIG. 12A depicts exemplary experimental results demonstrating that the frequencies of mutation were binned indicated on a scale from yellow to red and mapped onto a conformational model of this region of human 7SK (ref 39). FIG. 12B depicts exemplary experimental results demonstrating that each nucleotide was classified as either single stranded or basepaired. Differences between mutation rates of the basepaired and single stranded nucleotides were not found to be significantly different when analyzed using a two-sided Wilcoxon test.

FIG. 13, comprising FIG. 13A depicts exemplary experimental results demonstrating (Left) tracks depicting coverage from all reads (gray) for transcripts with slow (Ybx1), moderate (Dhx9), or fast (Fos12) rates of turnover, and (Right), tracks from reads with increasing numbers of T-to-C mutations (see scale) displaying mutational content provided by TimeLapse chemistry (right, y-axis zoom 3×). FIG. 13B depicts exemplary experimental results demonstrating the distribution of reads with each number of T-to-C mutations (points) overlaid on a model of the estimated distribution of reads from new transcripts and pre-existing transcripts (gray) for Ybx1, Dhx9, and Fos12. The estimated fraction of new reads is indicated for each plot. Light gray, 95% CI. FIG. 13C depicts exemplary experimental results demonstrating the distribution of T-to-C mutations found in reads mapping to Ybx1, Dhx9, and Fos12, separated by total, exonic, or intronic reads. FIG. 13D depicts exemplary experimental results demonstrating TT-TimeLapse-seq and RNA-seq tracks of DHX9. FIG. 13E depicts exemplary experimental results demonstrating a cumulative distribution plot of reads containing splice-junctions in RNA-seq, and TT-TimeLapse-seq. FIG. 13F depicts exemplary experimental results demonstrating a cumulative distribution plot of intron-only reads in RNA-seq and TT-TimeLapse-seq with the same scale as in FIG. 13E. FIG. 13G depicts exemplary results from experiments using TimeLapse-seq to distinguish new RNAs after heat shock. Log2 fold changes after heat shock in total RNA-seq counts and new RNA counts for the top RNAs identified in FIG. 13B as significantly changed upon heat shock (Padj<0.01). FIG. 13H depicts exemplary experimental results demonstrating RNA-seq and TimeLapse-seq tracks of Hsph1 (top) and Hsp90aa1 (bottom) upon heat shock.

FIG. 15, comprising FIG. 15A depicts exemplary experimental results demonstrating a correlation of estimated RNA half-lives between 1 h TimeLapse-seq replicates in MEF cells. FIG. 15B depicts exemplary experimental results demonstrating a correlation with previously reported RNA half-lives in mouse 3T3 cells (Schwanhausser et al. 2011, ref 17). FIG. 15C depicts exemplary experimental results demonstrating a correlation of replicate RNA-seq counts from K562 4 hour TimeLapse-seq samples. FIG. 15D depicts exemplary experimental results demonstrating estimated RNA transcript half-lives from K562 4 hour TimeLapse-seq samples FIG. 15E depicts exemplary experimental results demonstrating a correlation of estimated RNA transcript half-lives from TimeLapse-seq compared to RNA transcript half-lives derived from Friedel et al. (2009) Nucleic Acids Res. 37:e115). FIG. 15F depicts exemplary experimental results demonstrating a plot of estimated half-lives for K562 transcripts, filtered by indicated GO annotation term, and average half-lives for each family.

FIG. 16, comprising FIG. 16A depicts exemplary experimental results demonstrating the probability of successfully detecting changes in the new read pool when the chemical efficiency (ychem, 80%) is varied. FIG. 16B depicts exemplary experimental results demonstrating the probability of successfully detecting changes in the new read pool when the fraction of new transcripts (n, 0.2) is varied. FIG. 16C depicts exemplary experimental results demonstrating the probability of successfully detecting changes in the new read pool when the fold change (x, 2) is varied. FIG. 16D depicts exemplary experimental results demonstrating the probability of successfully detecting changes in the new read pool when the read length (1r, 150) is varied. FIG. 16E depicts exemplary experimental results demonstrating the probability of successfully detecting changes in the new read pool when the background mutation rate (po, 0.001) is varied. FIG. 16F depicts exemplary experimental results demonstrating the probability of successfully detecting changes in the new read pool when the $s^4U$ incorporation rate (pn, 0.042) is varied.

FIG. 17, comprising FIG. 17A depicts an exemplary scheme of TTTimeLapse- seq. FIG. 17B depicts exemplary experimental results demonstrating a TT-TimeLapse-seq track of ACTB. FIG. 17C depicts exemplary experimental results demonstrating a cumulative distribution analysis of splice-junction reads from RNA-seq and TT-seq experiments, along with TT-seq reads filtered for T-to-C mutation content. FIG. 17D depicts exemplary experimental results demonstrating a cumulative distribution analysis of intronic reads from RNA-seq and TT-seq experiments, along with TT-seq reads filtered for T-to-C mutation content. Biochemical enrichment of RNA from cells treated with $s^4U$ for 5 min results in a depletion of splice-junction reads, present in processed mRNAs. T-to-C mutation-containing reads display a marked decrease in splice-junction content compared to biochemical enrichment alone, consistent with reports of background mRNA contamination observed in biochemical enrichment experiments (Rabani et al., (2014) Cell, 159:1698-1710). Similarly, T-to-C mutation-containing reads display an increase in intron-only containing reads. FIG. 17E depicts exemplary experimental results demonstrating a correlation analysis of total read counts in TT-TimeLapse-seq replicates. FIG. 17F depicts exemplary experimental results demonstrating a correlation analysis of intronic read counts in TT-TimeLapse-seq replicates. FIG. 17G depicts exemplary experimental results demonstrating a correlation analysis of splice-junction read counts in TT-TimeLapse-seq replicates. FIG. 17H depicts an exemplary barplot of the distribution of T-to-C mutations in replicates of RNA-seq input, TT-TimeLapse-seq total, or TT-TimeLapse-seq reads filtered for intron or splice-junction content. FIG. 17I depicts an exemplary table of proportions of contaminating reads for TT-TimeLapse-seq replicates by mutation count per read estimated through splice-junction or intron analysis.

FIG. 19, comprising FIG. 19A depicts the results of example experiments demonstrating that TimeLapse-seq leads to a global increase in T-to-C mutations that is dependent on s⁴U treatment and TimeLapse chemistry ($p<2\times10^{-16}$, Wilcoxon). Box-and-whiskers plot displaying the number of uniquely aligned reads with two or more T-to-C mutations for each RNA. Counts are log transformed with a pseudo-count of one added to each. FIG. 19B (left) provides exemplary browser tracks depicting coverage from all reads (light gray) or reads with increasing numbers of T-to-C mutations (see scale) for Myc, a fast-turnover transcript. FIG. 19B (right) depicts the results of example experiments demonstrating the distribution of reads with each number of T-to-C mutations (points) overlaid on a model estimating the distribution of reads from new transcripts (dark gray) and pre-existing transcripts (light gray). The estimated fraction of new reads is indicated for each plot with 95% confidence interval shown in light gray. FIG. 19C depicts the results of example experiments demonstrating the estimated half-lives of each transcript (top 1150 transcripts). The transcripts are ordered by half-life and depicted with a line representing the mean estimated half-life for each gene, with individual replicates depicted as points overlaid on the plot. RNAs are labeled to illustrate transcripts with diverse turnover rates. FIG. 19D depicts exemplary transcripts with different rates of turnover and their associated histograms, as in FIG. 19B.

FIG. 24, comprising FIG. 24A depicts exemplary experimental results demonstrating TimeLapse-seq tracks depicting heat shock induction of Hspa1b. FIG. 24B depicts exemplary experimental results demonstrating a differential expression analysis using TimeLapse-seq to distinguish new RNAs (left) and total RNA (right) with and without heat shock (DEseq2; dark points: padj<0.1). FIG. 24C depicts exemplary experimental results demonstrating the Rsrp1 transcript appears to be stabilized upon heat shock, with the terminal exon displaying the highest degree of stabilization. FIG. 24D depicts exemplary experimental results demonstrating qPCR quantification of varying Rsrp1 transcript features (Table 3). FIG. 24E depicts exemplary experimental results demonstrating the log2 fold change of total RNA-seq reads and TimeLapse-seq inferred new reads upon heat shock. Highlighted are histone mRNAs, which appear to be destabilized upon heat shock. FIG. 24F depicts an exemplary browser shot and T-to-C mutation distribution of Hist1h1d mRNA. Total RNA levels of Hist1h1d mRNAs decrease, though the fraction of new RNAs during the 1 hour heat shock remain consistent, suggesting a post-transcriptional degradation mechanism observed previously in replicative histone mRNAs during select stages of the cell cycle. FIG. 24G depicts exemplary experimental results demonstrating a qPCR analysis of Hist1h1d. FIG. 24H depicts exemplary experimental results demonstrating a differential expression analysis of RNA-seq data from (Shalgi et al., (2014) Cell Rep, 7:1362-1370), demonstrating a decrease in histone mRNAs due to heat shock.

FIG. 25, comprising FIG. 25A provides example Time-Lapse-seq tracks depicting an RNA (Hspa1b) that is induced upon heat shock, with histogram as in FIG. 19. FIG. 25B depicts an example differential expression analysis of Time-Lapse-seq data demonstrating larger fold changes in the TimeLapse-seq data than is apparent from RNA-seq analysis (DEseq2, incorporates a zero-centered normal prior), with purple points representing $p_{adj}<0.05$. FIG. 25C provides an example heatmap depicting the row-normalized relative expression levels of differentially expressed genes upon heat shock. FIG. 25D depicts the results of example experiments demonstrating that TimeLapse-seq reveals the induction of Hsph1 upon heat shock, which is not evident in RNA-seq analysis. FIG. 25E depicts the results of example experiments demonstrating that total Hist1h1d RNA is reduced upon heat shock, but displays a similar fraction of new transcripts, suggesting heat-shock-induced degradation of pre-existing transcripts. FIG. 2F depicts the results of example experiments demonstrating a different terminal exon of Rsrp1 is induced upon heat shock.

FIG. 26, comprising FIG. 26A depicts the results of example experiments demonstrating a differential gene expression analysis comparing counts of T-to-C mutations in each transcript with total reads. Reads with high turnover are over-represented in the normalized T-to-C reads, while low turnover genes are underrepresented. This plot depicts variance-stabilized fold-change (DESeq2) compared to the normalized mean expression level. Transcripts are darkened if they have a BH adjusted p-value of less than 0.1 (DESeq2 default values). FIG. 26B depicts an example heatmap of transcripts with significant fold change. While the analysis to determine the gene-set only included samples that were not subjected to heat shock, all samples are depicted here. Selected transcripts in each set are annotated.

FIG. 27, comprising FIG. 27A depicts the results of example experiments demonstrating ASXL1 tracks from TimeLapse-seq (4-hour $s^4U$ treatment) with exon-containing regions expanded (lower panel). FIG. 27B depicts the results of example experiments demonstrating the exonic T-to-C mutation distributions for ASXL1 in comparison with three transcripts with different stabilities, ACTB, CDK1, and FOSL1.

FIG. 28, comprising FIG. 28A depicts the results of example experiments demonstrating the mutation distribution for the different regions of the ASXL1 transcript from 4 hour TimeLapse-seq data in MEF cells. FIG. 28B depicts the results of example experiments demonstrating RT-qPCR for ASXL1 isoforms and DHX9 mRNA (normalized to actin levels) following transcriptional inhibition by actinomycin D. FIG. 28C depicts the results of example experiments demonstrating the location of qPCR primers for the ASXL1 transcript used in actinomycin D transcription block in K562 cells. Fraction remaining (frac9h) values for each primer are estimated using actin normalized Ct values after 9 hours of transcriptional inhibition FIG. 29 depicts a table providing sequencing statistics for various conditions.

DETAILED DESCRIPTION OF THE INVENTION

Figure 1A:
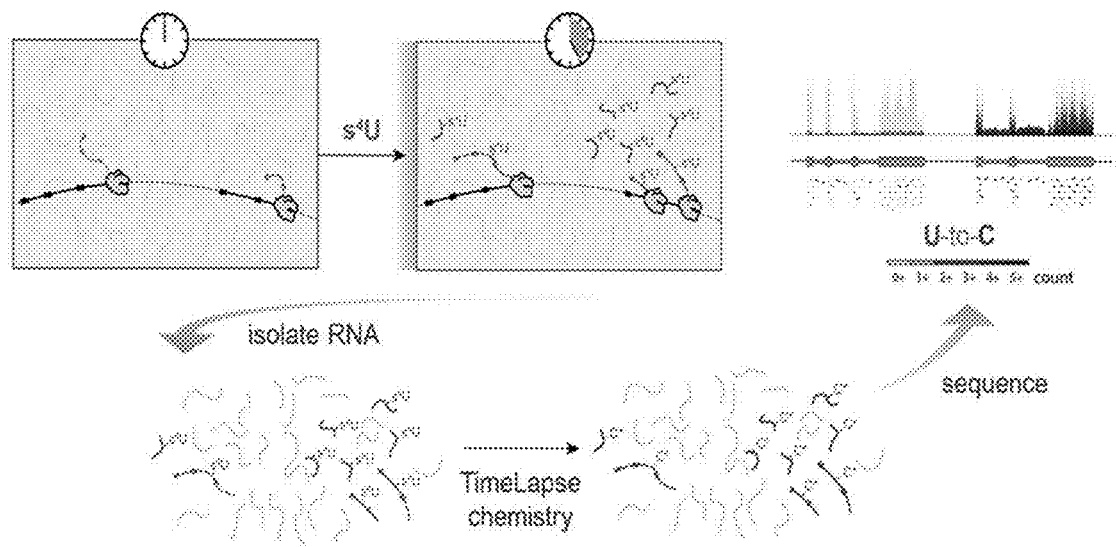
FIG. 1A through FIG. 1I, depicts the results of example experiments demonstrating that TimeLapse-seq uses a convertible nucleoside approach to identify new transcripts in a sequencing experiment.

The invention described herein arises from the development of a nucleic acid-friendly oxidative-nucleophilic-aromatic-substitution chemistry (TimeLapse chemistry) to convert a thiol-containing nucleoside (e.g., $s^4U$, $s^6G$, $s^6dG$ or $s^4T$) into an analog of a different base. Nucleic-acid friendly conditions have a near neutral pH to avoid base-catalyzed hydrolysis of the labile phosphodiester linkages, and conditions that will not destroy other functionality on the RNA such as oxidative damage to the nucleobases themselves. The substitution leads to apparent U-to-C, T-to-C, or G-to-A mutations that mark newly synthesized (nascent) nucleic acid molecules upon sequencing. The substitution leads to progressively higher levels of the mark over time, providing information about when the nucleic acid was synthesized. In various embodiments, the invention provides methods for performing TimeLapse-seq to reveal nucleotide dynamics, regulation, and turnover of nucleic acid molecules that are concealed in traditional sequencing methods.

In some embodiments, the methods of the invention are useful for identifying when nucleic acid molecules were synthesized including, but not limited to, newly synthesized DNA molecules, including nuclear and mitochondrial (mtDNA) molecules, and newly synthesized RNA molecules, including mRNA, rRNA, noncodingRNA (ncRNA), large ncRNA (lncRNA), small nuclear RNA (snRNA), small cytoplasmic RNA (scRNA), small nucleolar RNA (snoRNA), small interfering RNA (siRNA) and microRNA (miRNA) molecules.

In various embodiments, the nucleic acid molecule for use in the invention can be in a cell or isolated from a cell. In various embodiments, a cell can be in a cell culture, in a live tissue slice, or in a primary cell culture derived from a primary cell of a subject. In some embodiments, the nucleic acid molecule is from a normal cell or from a disease cell. In some embodiments, the nucleic acid molecule is from a cell undergoing a treatment.

In one embodiment, the invention provides methods for introducing one or more mutations into newly synthesized nucleic acid molecules in a cell or a population of cells. In one embodiment, the methods comprise contacting a cell with a thiol-containing nucleoside, isolating at least one nucleic acid molecule, and converting the thiol-containing nucleoside into an analog of a different base in at least one cell in order to generate a mutation. In one embodiment, the conversion of the thiol-containing nucleoside into an analog of a different base is performed by contacting the at least one nucleic acid molecule with an oxidant and a nucleophile. The method of converting a thiol-containing nucleoside in a nucleic acid molecule into an analog of a different base by contacting the nucleic acid molecule with an oxidant and a nucleophile is referred to herein as TimeLapse chemistry.

In some embodiments, the invention relates to methods of sequencing an isolated nucleic acid. The methods of sequencing an isolated nucleic acid comprising a base analog generated using TimeLapse chemistry as described herein is referred to herein as TimeLapse-seq. In the TimeLapse-seq methodology, a mutated nucleic acid molecule is generated, with at least one U-to-C, T-to-C, or G-to-A mutation. Subsequent sequencing and analysis using a mutational mapping strategy can be used to determine which nucleic acid molecules that were synthesized after the introduction of a thiol-containing nucleoside (i.e., contain at least one U-to-C, T-to-C, or G-to-A mutation due to the conversion of a thiol-containing nucleoside to an analog of a different base using TimeLapse chemistry) and those that were synthesized before the introduction of the a thiol-containing nucleoside (i.e., do not contain at least one U-to-C, T-to-C, or G-to-A mutation due to the conversion of a thiol-containing nucleoside to an analog of a different base using TimeLapse chemistry).

In some embodiments, the methods of the invention are useful for identifying nucleic acid molecules that were actively transcribed during the time period that a cell is contacted with a thiol-containing nucleoside. In one embodiment, a nucleic acid molecule that is being actively transcribed is one that is upregulated or is accumulating. These nucleic acid molecules may be identified as molecules that have incorporated a thiol-containing nucleoside or have acquired a mutation due to the conversion of a thiol-containing nucleoside.

In some embodiments, the methods of the invention are useful for identifying nucleic acid molecules that were not being actively transcribed during the time period that a cell is contacted with a thiol-containing nucleoside. In one embodiment, a nucleic acid molecule that is not being actively transcribed is one that is downregulated or is not accumulating. These nucleic acid molecules may be identified as molecules that did not incorporated a thiol-containing nucleoside or did not acquired a mutation due to the conversion of a thiol-containing nucleoside.

In one embodiment, the methods of the invention are useful for characterizing nucleic acid dynamics, for example through characterizing newly synthesized nucleic acid molecules at one or more time points and/or under one or more treatment conditions. In one embodiment, the one or more time points may be one or more time points during the cell cycle of a population of cells, such as synchronized cell population. In one embodiment, the one or more time points may be before and after a treatment with, by way of non-limiting examples, a pharmaceutical agent, a treatment that alters the level or expression of a gene or gene product (e.g., a gene therapy, a microRNA replacement therapy, an anti-microRNA therapy, an siRNA therapy, treatment with a protein, treatment with a peptide, treatment with an antibody), or a treatment that alters a condition of a cell (e.g., alteration in temperature, oxygen level, desiccation). Such methods are useful for, by way of a non-limiting example, evaluating changes in DNA or RNA expression as a result of a treatment.

In one embodiment, the methods of the invention are useful for characterizing nucleic acid dynamics associated with a cell type, with a cell stage, or with a disease or disorder. Such methods are useful for, by way of non-limiting example, evaluating DNA or RNA expression or dynamics associated with a particular cell type, cell stage, or disease or disorder.

Definitions

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"Amplification" refers to any means by which a polynucleotide sequence is copied and thus expanded into a larger number of polynucleotide molecules, e.g., by reverse transcription, polymerase chain reaction, and ligase chain reaction, among other methods.

"Antisense" refers to the nucleic acid sequence of the non-coding strand of a double stranded DNA molecule encoding a protein, or to a sequence which is substantially homologous to the non-coding strand. As defined herein, an antisense sequence is complementary to the sequence of a double stranded DNA molecule encoding a protein. It is not necessary that the antisense sequence be complementary solely to the coding portion of the coding strand of the DNA molecule. The antisense sequence may be complementary to regulatory sequences specified on the coding strand of a DNA molecule encoding a protein, which regulatory sequences control expression of the coding sequences.

Herein, the term "barcode" refers to a sequence that can or will be used to group nucleic acid molecules. The present invention provides for attaching a barcode sequence to a nucleic acid of interest, such as a naturally occurring or a synthetically derived nucleic acids. For example, sequences that undergo randomly primed synthesis in the proximity of a particular surface can or will be physically attached to the sequence of a barcode or to the sequences of a barcode set, as defined below.

The term "barcode set" refers to one or more barcodes that contain sequence features that distinguish them as distinct from other barcode sets. A barcode set can contain unrelated sequences, or sequences that are in some manner related, such as sequences in which there are errors or intentional differences introduced during their synthesis. As a non-limiting example, each barcode in a barcode set can have a sequence such as XRRXXX, in which X indicates a defined nucleotide, such as guanine (G), adenine (A), thymine (T), cytosine (C), uracil (U), and inosine (I), or other nucleotide, and R indicates any purine nucleotide. These nucleotides will be referred to by their single letter codes, G, A, T, C, U, and I, throughout.

"Binding" is used herein to mean that a first moiety interacts with a second moiety.

"Biological sample," as that term is used herein, means a sample obtained from a single-cellular or multi-cellular organism that can be used to assess the level of expression of a nucleic acid according to the method of the invention. Such a sample includes, but is not limited to, a cell, a blood sample, or a tissue sample.

"Complementary" as used herein refers to the broad concept of subunit sequence complementarity between two nucleic acids, e.g., two DNA molecules. When a nucleotide position in both of the molecules is occupied by nucleotides normally capable of base pairing with each other, then the nucleic acids are considered to be complementary to each other at this position. Thus, two nucleic acids are complementary to each other when a substantial number (at least 50%) of corresponding positions in each of the molecules are occupied by nucleotides which normally base pair with each other (e.g., A:T and G:C nucleotide pairs). As defined herein, an antisense sequence is complementary to the sequence of a double stranded DNA molecule encoding a protein. It is not necessary that the antisense sequence be complementary solely to the coding portion of the coding strand of the DNA molecule. The antisense sequence may be complementary to regulatory sequences specified on the coding strand of a DNA molecule encoding a protein, which regulatory sequences control expression of the coding sequences.

A "coding region" of a gene consists of the nucleotide residues of the coding strand of the gene and the nucleotides of the non-coding strand of the gene which are homologous with or complementary to, respectively, the coding region of an mRNA molecule which is produced by transcription of the gene.

A "coding region" of an mRNA molecule also consists of the nucleotide residues of the mRNA molecule which are matched with an anticodon region of a transfer RNA molecule during translation of the mRNA molecule or which encode a stop codon. The coding region may thus include nucleotide residues corresponding to amino acid residues which are not present in the mature protein encoded by the mRNA molecule (e.g., amino acid residues in a protein export signal sequence).

The term "contig" has general meaning in the art, and refers to contiguous partial sequences that can or may be assembled into a single sequence. Assembly is typically done by aligning sequences to each other or to a reference sequence, or a combination of both.

"Denaturing" or "denaturation of" a complex comprising two polynucleotides (such as a first primer extension product and a second primer extension product) refers to dissociation of two hybridized polynucleotide sequences in the complex. The dissociation may involve a portion or the whole of each polynucleotide. Thus, denaturing or denaturation of a complex comprising two polynucleotides can result in complete dissociation (thus generating two single stranded polynucleotides), or partial dissociation (thus generating a mixture of single stranded and hybridized portions in a previously double stranded region of the complex).

A "disease" is a state of health of an animal wherein the animal cannot maintain homeostasis, and wherein if the disease is not ameliorated, then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

A "genomic DNA" is a DNA strand which has a nucleotide sequence homologous with a gene as it exists in the natural host. By way of example, a fragment of a chromosome is a genomic DNA.

The term "isoform," when applied to RNA, refers to RNA molecules that share some portion but not all of their sequence, and derive from the same gene. For RNA, the sequences can differ due to alternative promoter usage or post-transcriptional processing, such as splicing and polyadenylation. With respect to RNA, differences due to mutations are also included. When applied to DNA, isoform refers to two or more DNA regions that substantially map to the same one or more chromosome region, and that share some portion but not all of their sequence. With respect to DNA, also included are differences due to mutations. Of particular but non-exclusive interest with respect to DNA isoforms are chromosomal rearrangements.

An "isolated cell" refers to a cell which has been separated from other components and/or cells which naturally accompany the isolated cell in a tissue or organism.

An "isolated nucleic acid" refers to a nucleic acid (or a segment or fragment thereof) which has been separated from sequences which flank it in a naturally occurring state, e.g., a RNA fragment which has been removed from the sequences which are normally adjacent to the fragment. The term also applies to nucleic acids which have been substantially purified from other components which naturally accompany the nucleic acid, e.g., RNA or DNA or proteins, which naturally accompany it in the cell. The term therefore includes, for example, purified genomic or transcriptomic cellular content In the context of the present invention, the following abbreviations for the commonly occurring nucleic acid bases are used. "A" refers to adenosine, "C" refers to cytidine, "G" refers to guanosine, "T" refers to thymidine, and "U" refers to uridine.

Sequence "mutation," as used herein, refers to any sequence alteration in a sequence of interest in comparison to a reference sequence. A reference sequence can be a wild type sequence or a sequence to which one wishes to compare a sequence of interest. A sequence mutation includes single nucleotide changes, or alterations of more than one nucleotide in a sequence, due to mechanisms such as substitution, deletion or insertion. Single nucleotide polymorphism (SNP) is also a sequence mutation as used herein.

"Newly synthesized" or "nascent" nucleic acid molecules, as used herein, refers to those nucleic acid molecules that have been synthesized after a specific event or time point, as compared to nucleic acid molecules synthesized prior to a specific event or time point. In the context of the current invention, nascent nucleic acid molecules are those molecules synthesized after addition of a thiol-containing nucleoside which incorporate at least one thiol-containing nucleoside into the nucleic acid molecule.

"Nucleic acid analogs" are structurally modified, polymeric analogs of DNA and RNA made by chemical synthesis from monomeric nucleotide analog units, and possessing some of the qualities and properties associated with nucleic acids. PNA and phosphorothioate oligonucleotides are examples of two of many nucleic acid analogs known in the art. "Watson/Crick base-pairing" and "Watson/Crick complementarity" refer to the pattern of specific pairs of nucleotides, and analogs thereof, that bind together through hydrogen bonds, e.g., A pairs with T and U, and G pairs with C. The act of specific base-pairing is "hybridization" or "hybridizing." A hybrid forms when two, or more, complementary strands of nucleic acids or nucleic acid analogs undergo base-pairing.

The term "oligonucleotide" typically refers to short polynucleotides, generally no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

A "polynucleotide" means a single strand or parallel and anti-parallel strands of a nucleic acid. Thus, a polynucleotide may be either a single-stranded or a double-stranded nucleic acid. The term "nucleic acid" typically refers to large polynucleotides.

A "primer" is generally a nucleotide sequence (i.e., a polynucleotide), generally with a free 3'-OH group, that hybridizes with a template sequence (such as a target RNA, or a primer extension product) and is capable of promoting polymerization of a polynucleotide complementary to the template. A "primer" can be, for example, an oligonucleotide. It can also be, for example, a sequence of the template (such as a primer extension product or a fragment of the template created following RNase cleavage of a template-DNA complex) that is hybridized to a sequence in the template itself (for example, as a hairpin loop), and that is capable of promoting nucleotide polymerization.

A "random primer," as used herein, is a primer that comprises a sequence that is designed not necessarily based on a particular or specific sequence in a sample, but rather is based on a statistical expectation (or an empirical observation) that the sequence of the random primer is hybridizable (under a given set of conditions) to one or more sequences in the sample. The sequence of a random primer (or its complement) may or may not be naturally-occurring, or may or may not be present in a pool of sequences in a sample of interest. The amplification of a plurality of RNA species in a single reaction mixture would generally, but not necessarily, employ a multiplicity of random primers. As is well understood in the art, a "random primer" can also refer to a primer that is a member of a population of primers (a plurality of random primers) which collectively are designed to hybridize to a desired and/or a significant number of target sequences. A random primer may hybridize at a plurality of sites on a nucleic acid sequence. The use of random primers provides a method for generating primer extension products complementary to a target polynucleotide which does not require prior knowledge of the exact sequence of the target. Conventional notation is used herein to describe polynucleotide sequences: the left-hand end of a single-stranded polynucleotide sequence is the 5'-end; the left-hand direction of a double-stranded polynucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand"; sequences on the DNA strand which are located 5' to a reference point on the DNA are referred to as "upstream sequences"; sequences on the DNA strand which are 3' to a reference point on the DNA are referred to as "downstream sequences."

"Probe" refers to a polynucleotide that is capable of specifically hybridizing to a designated sequence of another polynucleotide. A probe specifically hybridizes to a target complementary polynucleotide, but need not reflect the exact complementary sequence of the template. In such a case, specific hybridization of the probe to the target depends on the stringency of the hybridization conditions. Probes can be labeled with, e.g., chromogenic, radioactive, or fluorescent moieties and used as detectable moieties.

"Homologous," as used herein, refers to the subunit sequence similarity between two polymeric molecules, e.g., between two nucleic acid molecules, e.g., two DNA molecules or two RNA molecules, or between two polypeptide molecules. When a subunit position in both of the two molecules is occupied by the same monomeric subunit, e.g., if a position in each of two DNA molecules is occupied by adenine, then they are completely or 100% homologous at that position. The percent homology between two sequences is a direct function of the number of matching or homologous positions, e.g., if half (e.g., five positions in a polymer ten subunits in length) of the positions in two compound sequences are homologous then the two sequences are 50% identical, if 90% of the positions, e.g., 9 of 10, are matched or homologous, the two sequences share 90% homology.

In addition, when the terms "homology" or "identity" are used herein to refer to the nucleic acids and proteins, it should be construed to be applied to homology or identity at both the nucleic acid and the amino acid sequence levels.

A "sequence read" corresponds to a determination of the nucleotides in a target nucleic acid molecule in the order in which they occur and can or will include only a part of the target molecule, and can or will exclude other parts of the target molecule. The sequencing read in this context does not necessarily correspond to a fixed length. Current sequencing methods can produce reads of various lengths. Some sequencing methods, including but not limited to those that use physical separation of molecules of different sizes, can or will produce sequence reads ranging from one nucleotide to more than a thousand nucleotides. Alternatively, some sequencing methods produce shorter reads consisting of 1 to 50 nucleotides, 1 to 100 nucleotides, 1 to 200 nucleotides and longer, and the possible lengths may increase as technology improves.

The term "sequence" refers to the sequential order of nucleotides in a nucleic acid molecule, or, depending on context, refers to a molecule or part of a molecule in which a particular sequential order of nucleotides exists.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range and, when appropriate, partial integers of the numerical values within ranges. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range. It is understood that any and all whole or partial integers between any ranges set forth herein are included herein.

Description

In one embodiment, the present invention is a method of generating mutations in nucleic acid molecules. The method comprises the steps of contacting a cell with a thiol-containing nucleoside so that at least one thiol-containing nucleoside is incorporated into a nucleic acid molecule, isolating the nucleic acid molecules, treating the isolated nucleic acid molecules with an oxidant and a nucleophile to convert a thiol-containing nucleoside to a convertible nucleoside intermediate and further convert the convertible nucleoside intermediate into an analog of a different base (i.e., an analog of a base that is not the same as the base of the thiol-containing nucleoside or nucleobase).

In one embodiment, the present invention is a method of identifying newly synthesized (or nascent) nucleic acid molecules by inducing at least one mutation in a nucleic acid sequence and then determining the presence and/or location of the at least one mutation. The method comprises the steps of contacting a cell with a thiol-containing nucleoside so that at least one thiol-containing nucleoside is incorporated into a nucleic acid molecule, isolating the nucleic acid molecules, treating the isolated nucleic acid molecules with an oxidant and a nucleophile to convert a thiol-containing nucleoside or nucleobase to a convertible nucleoside intermediate and further convert the convertible nucleoside intermediate into an analog of a different base (i.e., an analog of a base that is not the same as the base of the thiol-containing nucleoside or nucleobase), amplifying the nucleic acid molecule comprising an analog of a different base thereby generating a mutation in the amplification product, and determining the presence or location of a mutation in the amplification product.

In some embodiments, the methods of the invention are useful for identifying nucleic acid molecules that were being actively transcribed during the time period that a cell is contacted with a thiol-containing nucleoside.

In one embodiment, the methods of the invention are useful in that they capture both nucleic acid molecules comprising a thiol-containing nucleoside and nucleic acid molecules that do not comprise a thiol-containing nucleoside. This allows the method of the invention to analyze those nucleic acid molecules that were being actively transcribed and those that were not. This method provides an advantage over pull-down methods that only capture actively transcribed nucleic acid molecules (e.g., BrdU based sequencing methods.) Therefore, in some embodiments, the methods of the invention are useful for identifying nucleic acid molecules that were not being actively transcribed (i.e. were silent) during the time period that a cell is contacted with a thiol-containing nucleoside.

In some embodiments, the methods of the invention are useful for revealing the dynamics of newly synthesized nucleic acid molecules. In various embodiments, the dynamics include stability, synthesis and degradation of particular newly synthesized nucleic acid molecules within a diverse and changing population of nucleic acid molecules.

In some embodiments, the methods of the invention are useful for identifying nucleic acid molecules that were upregulated (i.e., increases expression) during the time period that a cell is contacted with a thiol-containing nucleoside or nucleobase.

In some embodiments, the methods of the invention are useful for identifying nucleic acid molecules that were downregulated (i.e., decreased expression) during the time period that a cell is contacted with a thiol-containing nucleoside.

In various embodiments, the thiol-containing nucleoside or nucleobase used in the methods of the invention is at least one selected from the group consisting of 4-thiouridine ($s^4U$), 6-thioguanine ($s^6G$), 6-thiodeoxyguaosine ($s^6dG$) and 4-thiothymidine ($s^4T$). In one embodiment, a thiol nucleobase is added, and an enzyme expressed in the cell transforms the nucleobase into a nucleotide. For example, in one embodiment, a nucleobase is 4-thiouricil which is transformed into 4-thiouridine.

In one embodiment, the selection of the thiol-containing nucleoside or nucleobase is dependent on whether DNA or RNA based nucleic acid molecules are being detected. In one embodiment, the invention is a method of identifying a newly transcribed RNA molecule. Therefore, in one embodiment, the thiol-containing nucleoside or nucleobase is one of 4-thiouricil, $s^4U$, $s^6G$ and $s^6dG$ such that one of $s^4U$, $s^6G$ and $s^6dG$ is incorporated into newly transcribed RNA molecules.

In one embodiment, the invention is a method of identifying a newly replicated DNA molecule. Therefore, in one embodiment, the thiol-containing nucleoside or nucleobase is one of $s^4T$, $s^6G$ and $s^6dG$ such that one of $s^4T$, $s^6G$ and $s^6dG$ is incorporated into newly replicated DNA molecules.

In one embodiment, a thiol-containing nucleoside or nucleobase is converted to a convertible nucleoside intermediate and further converted into an analog of a different base (i.e., an analog of a base that is not the same as the base of the thiol-containing nucleoside or nucleobase). In one embodiment, 4-thiouricil, $s^4U$ or $s^4T$ is converted into a cytidine analog. In one embodiment, $s^6G$ or $s^6dG$ is converted into an adenine analog.

In various embodiments, the mutation generated in a newly synthesized nucleic acid molecule is dependent on the thiol-containing nucleoside or nucleobase used. In one embodiment, the thiol-containing nucleoside or nucleobase is 4-thiouricil or $s^4U$ and the mutation generated by the method of the invention is a U to C mutation. In one embodiment, the thiol-containing nucleoside or nucleobase is $s^4T$ and the mutation generated by the method of the invention is a T to C mutation. In one embodiment, the thiol-containing nucleoside or nucleobase is $s^6G$ or $s^6dG$ and the mutation generated by the method of the invention is a G to A mutation.

In various embodiments, the oxidant used in the methods of the invention is at least one selected from the group consisting of hydrogen peroxide ($H_2O_2$), sodium iodate ($NaIO_3$), potassium permagnate ($KMnO_4$), sodium periodate ($NaIO_4$), and meta-Chloroperoxybenzoic acid (mCPBA).

In various embodiments, the nucleophile used in the methods of the invention is at least one selected from the group consisting of 2,2,2-trifluoroethylamine (TFEA), benzylamine ($C_6H_5CH_2NH_2$), O-methylhydroxylamine hydrochloride ($MeONH_2$), aniline ($C_6H_5NH_2$), hydrazine ($H_2NNH_2$), ammonia ($NH_3$), 1,1-dimethylethylenediamine (($CH_3)_2NCH_2CH_2NH_2$), methylamine ($CH_3NH_2$), propargylamine ($HCCCH_2NH_2$), allylamine ($H_2CCHCH_2NH_2$), 2-azidoethylamine ($N_3CH_2CH_2NH_2$), cysteiamine disulfide (($HSCH_2CH_2S)_2$) and 4-(Trifluoromethyl)benzylamine ($CF_3C_6H_4CH_2NH_2$).

In one embodiment, the oxidant is mCPBA and the nucleophile is at least one of TFEA, benzylamine, $MeONH_2$, aniline, ammonia, and 4-(Trifluoromethyl)benzylamine. In one embodiment, the oxidant is sodium iodate and the nucleophile is $MeONH_2$. In one embodiment, the oxidant is sodium periodate and the nucleophile is at least one of TFEA, benzylamine, and aniline. In one embodiment, the oxidant is hydrogen peroxide and the nucleophile is TFEA.

Assays

In various embodiments, the methods of the invention are useful to examine nucleic acid dynamics in any cell type. In one embodiment, a cell of use in the method of the invention is any cell this is undergoing active nucleic acid synthesis. The cell may be from any organism, including but not limited to, a plant, an animal, and a microorganism including bacteria, cyanobacteria, archaea, fungi, protozoa, and algae. A bacteria may be a gram positive or a gram negative bacteria. In one embodiment, an organism is a model organism useful for research.

In one embodiment, the organism is a mammal. Non-limiting examples of mammalian cell types that are appropriate for use in the methods of the invention include, but are not limited to stem and progenitor cells (e.g., embryonic stem cells, hematopoietic stem cells, mesenchymal stem cells, neural crest cells, etc.), endothelial cells, muscle cells, myocardial, smooth and skeletal muscle cells, mesenchymal cells, epithelial cells, hematopoietic cells (e.g., lymphocytes, including T-cells, such as Th1 T cells, Th2 T cells, Th0 T cells, cytotoxic T cells, B cells, pre-B cells, etc.; monocytes; dendritic cells; neutrophils; and macrophages; natural killer cells; mast cells; etc.); adipocytes, cells involved with particular organs, such as thymus, endocrine glands, pancreas, and brain (e.g., neurons, glia, astrocytes, dendrocytes, etc.).

In one embodiment, the methods of the invention are useful for examining nucleic acid dynamics following infection with a virus, including nucleic acid dynamics of viral DNA or viral RNA. Therefore, in one embodiment, the cell is a cell infected with a virus.

In one embodiment, the methods of the invention are useful for examining nucleic acid dynamics of endogenous nucleic acid molecules. In one embodiment, the methods of the invention are useful for examining nucleic acid dynamics of exogenous nucleic acid molecules. In various embodiments, therefore, the cell comprises an exogenous nucleic acid molecule (e.g., an expression vector for expression of an exogenous nucleic acid).

In some embodiments, the methods of the invention are useful to examine nucleic acid dynamics of cells undergoing or having undergone a treatment. In various embodiments, a treatment is a therapeutic treatment or a non-therapeutic treatment. In various embodiments, a treatment is at least one of treatment with a pharmaceutical agent, a treatment that alters the level or expression of a gene or gene product (e.g., a gene therapy, a microRNA replacement therapy, an anti-microRNA therapy, an siRNA therapy, treatment with a protein, treatment with a peptide, treatment with an antibody) or a treatment that alters a condition of a cell (e.g., alteration in temperature, oxygen level, desiccation).

In some embodiments, the methods of the invention are useful to examine nucleic acid dynamics in healthy, normal or control cells. In one embodiment, the methods of the invention are useful to examine nucleic acid dynamics in cells associated with a disease or disorder. In various embodiments, the disease or disorder may be hereditary or non-hereditary. In various embodiments, the disease or disorder may be a single gene disease or disorder, a complex disease or disorder (e.g., a disease such as, but not limited to, heart disease, diabetes, and obesity that does not have a single genetic cause), an epigenetic disease or disorder, an infectious disease, or any other known or unknown disease or disorder. The methods of the invention are not limited with regard to the disease or disorder that can evaluated using the method of the invention, but rather any cell associated with any disease or disorder can be evaluated using the method of the invention.

Nucleic acids can be obtained using known techniques. Nucleic acid herein includes DNA molecules, including but not limited to nuclear DNA and mtDNA molecules, and RNA molecules including but not limited to mRNA, rRNA, noncodingRNA (ncRNA), large ncRNA (lncRNA), small nuclear RNA (snRNA), small cytoplasmic RNA (scRNA), small nucleolar RNA (snoRNA), small interfering RNA (siRNA) and microRNA (miRNA) molecules. The nucleic acid can be double-stranded or single-stranded (i.e., a sense or an antisense single strand) and can be complementary to a nucleic acid encoding a polypeptide. The nucleic acid can be naturally occurring nucleic acid molecules (e.g., genomic DNA molecules), synthetic nucleic acid molecules (e.g., recombinant DNA molecules), or nucleic acid molecules derived therefrom (e.g., transcripts made from recombinant DNA molecules).

There are many methods known in the art for the detection of specific nucleic acid sequences and new methods are continually reported. A great many such methods involve the generation of an amplification product. Such methods include, but are not limited to polymerase chain reaction (PCR), reverse transcription, ligase chain reaction, loop mediated isothermal amplification, multiple displacement amplification, and nucleic acid sequence based amplification. In one embodiment, an amplification product is generated during sequencing, for example by a polymerase enzyme during single-molecule sequencing.

In one embodiment, a process for the detection of nucleic acid takes advantage of the polymerase chain reaction (PCR). The PCR process is well known in the art (U.S. Pat. No. 4,683,195, U.S. Pat. No. 4,683,202, and U.S. Pat. No. 4,800,159). To briefly summarize PCR, nucleic acid primers, complementary to opposite strands of a nucleic acid amplification target nucleic acid sequence, are permitted to anneal to the denatured sample. A DNA polymerase (typically heat stable) extends the DNA duplex from the hybridized primer. The process is repeated to amplify the nucleic acid target. If the nucleic acid primers do not hybridize to the sample, then there is no corresponding amplified PCR product.

In PCR, the nucleic acid probe can be labeled with a tag. In one embodiment, the detection of the duplex is done using at least one primer directed to the target nucleic acid. In yet another embodiment of PCR, the detection of the hybridized duplex comprises electrophoretic gel separation followed by dye-based visualization.

Nucleic acid amplification procedures by PCR are well known and are described in U.S. Pat. No. 4,683,202. Briefly, the primers anneal to the target nucleic acid at sites distinct from one another and in an opposite orientation. A primer annealed to the target sequence is extended by the enzymatic action of a heat stable polymerase. The extension product is then denatured from the target sequence by heating, and the process is repeated. Successive cycling of this procedure on both strands provides exponential amplification of the region flanked by the primers.

Amplification is then performed using a PCR-type technique, that is to say the PCR technique or any other related technique. Two primers, complementary to the target nucleic acid sequence are then added to the nucleic acid content along with a polymerase, and the polymerase amplifies the DNA region between the primers.

Stem-loop RT-PCR is a PCR method that is useful in the methods of the invention to amplify and quantify nucleic acid molecules of interest (See Caifu et al., 2005, Nucleic Acids Research 33:e179; Mestdagh et al., 2008, Nucleic Acids Research 36:e143; Varkonyi-Gasic et al., 2011, Methods Mol Biol 744:145-57). Briefly, the method includes two steps: RT and real-time PCR. First, a stem-loop RT primer is hybridized to a miRNA molecule and then reverse transcribed with a reverse transcriptase. Then, the RT products are quantified using conventional real-time PCR.

The expression "specifically hybridizing in stringent conditions" refers to a hybridizing step in the process of the invention where the oligonucleotide sequences selected as probes or primers are of adequate length and sufficiently unambiguous so as to minimize the amount of non-specific binding that may occur during the amplification. The oligonucleotide probes or primers herein described may be prepared by any suitable methods such as chemical synthesis methods.

Hybridization is typically accomplished by annealing the oligonucleotide probe or primer to the template nucleic acid under conditions of stringency that prevent non-specific binding but permit binding of this template nucleic acid which has a significant level of homology with the probe or primer.

Among the conditions of stringency is the melting temperature (Tm) for the amplification step using the set of primers, which is in the range of about 50° C. to about 95° C. Typical hybridization and washing stringency conditions depend in part on the size (i.e., number of nucleotides in length) of the template nucleic acid or the oligonucleotide probe, the base composition and monovalent and divalent cation concentrations (Ausubel et al., 1994, eds Current Protocols in Molecular Biology).

In one embodiment, the amplifications are real-time amplifications performed using a labeled probe, capable of specifically hybridizing in stringent conditions with a segment of a nucleic acid sequence, or polymorphic nucleic acid sequence. The labeled probe is capable of emitting a detectable signal every time each amplification cycle occurs.

The real-time amplification, such as real-time PCR, is well known in the art, and the various known techniques will be employed in the best way for the implementation of the present process. These techniques are performed using various categories of probes, such as hydrolysis probes, hybridization adjacent probes, or molecular beacons. The techniques employing hydrolysis probes or molecular beacons are based on the use of a fluorescence quencher/reporter system, and the hybridization adjacent probes are based on the use of fluorescence acceptor/donor molecules.

Hydrolysis probes with a fluorescence quencher/reporter system are available in the market, and are for example commercialized by the Applied Biosystems group (USA). Many fluorescent dyes may be employed, such as FAM dyes (6-carboxy-fluorescein), or any other dye phosphoramidite reagents.

Among the stringent conditions applied for any one of the hydrolysis-probes of the present invention is the Tm, which is in the range of about 50° C. to 95° C. In one embodiment, the Tm for a hydrolysis-probes is in the range of about 55° C. to about 80° C. In one embodiment, the Tm applied for a hydrolysis-probe is about 75° C.

In one embodiment, the method includes determining the sequence of the nucleic acid molecules. Direct sequence analysis can be used to determine the sequence of the nucleic acid molecules of interest. A sample comprising nucleic acid can be used, and PCR or other appropriate methods can be used to amplify all or a fragment of the nucleic acid, and/or its flanking sequences, if desired.

In one embodiment, the nucleic acid may be prepared (e.g., library preparation) for massively parallel sequencing in any manner as would be understood by those having ordinary skill in the art. Current methods for library preparation attempt to uniformly sample all sequences across every nucleic acid molecule, optimally with sufficient overlap to allow reassembly of the sequences from which they derive, or alternatively, to allow inference of the sequence by alignment with reference sequences. These methods are generally known in the art and generally relate to generating multiple copies of (amplifying) the complementary sequence of the nucleic acid sequences of interest. These standard methods have in common that the libraries of sequences that they contain correspond to the sequences of genes, or in various embodiments, from the messenger RNAs (i.e., mRNAs) transcribed from genes. In one embodiment, the libraries include RNA sequences from DNA regions that are not necessarily considered to be genes, including but not limited to microRNAs, short interfering RNAs, long non-coding RNAs, and others. Similar libraries contain sequences directly obtained from DNA, including but not limited to genomic DNA, organelle DNA, mitochondrial DNA, chloroplast DNA, pathogen DNA, commensal organism DNA, viral DNA, parasite DNA, and symbiotic organism DNA.

While there are many variations of library preparation, the purpose is to construct nucleic acid fragments of a suitable size for a sequencing instrument and to modify the ends of the sample nucleic acid to work with the chemistry of a selected sequencing process. Depending on application, nucleic acid fragments may be generated having a length of about 100-1000 bases. It should be appreciated that the present invention can accommodate any nucleic acid fragment size range that can be generated by a sequencer. This can be achieved by capping the ends of the fragments with nucleic acid adapters. These adapters have multiple roles: first to allow attachment of the specimen strands to a substrate (bead or slide) and second have nucleic acid sequence that can be used to initiate the sequencing reaction (priming). In many cases, these adapters also contain unique sequences (bar-coding) that allow for identification of individual samples in a multiplexed run. The key component of this attachment process is that only one nucleic acid fragment is attached to a bead or location on a slide. This single fragment can then be amplified, such as by a PCR reaction, to generate hundreds of identical copies of itself in a clustered region (bead or slide location).

One aspect of the present invention provides in part for methods to attach barcodes to nucleic acid molecules by primed synthesis in which the barcode is attached to the randomized or partially randomized primer, and the subsequent preparation of the resulting barcoded nucleic acid molecules for sequencing. The invention provides in part for grouping the nucleic acid molecules with attached barcodes and inferring or deducing the sequences of the single sample from which they derive.

In one embodiment, clusters of identical nucleic acid molecules form a product that is sequenced. The sequencing can be performed using any standard sequencing method or platform, as would be understood by those having ordinary skill in the art. Representative sequencing methods that can be used in the method of the invention include, but are not limited to direct manual sequencing (Church and Gilbert, 1988, Proc Natl Acad Sci U.S.A., 81:1991-1995; Sanger et al., 1977, Proc Natl Acad Sci U.S.A., 74:5463-5467; Beavis et al. U.S. Pat. No. 5,288,644); automated fluorescent sequencing; single-stranded conformation polymorphism assays (SSCP); clamped denaturing gel electrophoresis (CDGE); denaturing gradient gel electrophoresis (DGGE) (Sheffield et al., 1981, Proc Natl Acad Sci U.S.A., 86:232-236), mobility shift analysis (Orita et al., 1989, Proc Natl Acad Sci U.S.A., 86:2766-2770; Rosenbaum and Reissner, 1987, Biophys. Chem, 265:1275; Keen et al., 1991, Trends Genet, 7:5); RNase protection assays (Myers, et al., 1985, Science, 230:1242); Luminex xMAP™ technology; HTS (Gundry and Vijg, 2011, Mutat Res, doi:10.1016/j.mrfmmm.2011.10.001); NGS (Voelkerding et al., 2009, Clinical Chemistry, 55:641-658; Su et al., 2011, Expert Rev Mol Diagn, 11:333-343; Ji and Myllykangas, 2011, Biotechnol Genet Eng Rev, 27:135-158); and/or ion semiconductor sequencing (Rusk, 2011, Nature Methods, doi:10.1038/nmeth1330; Rothberg et al., 2011, Nature, 475:348-352). Next-gen sequencing platforms including, but not limited to, Illumina HiSeq, Illumina MiSeq, Life Technologies PGM, Pacific biosciences RSII and Helicos Heliscope can be used in the method of the invention for sequencing the nucleic acid molecules. These and other methods, alone or in combination, can be used to detect and quantify at least one nucleic acid molecule of interest.

The probes and primers according to the invention can be labeled directly or indirectly with a radioactive or nonradioactive compound, by methods well known to those skilled in the art, in order to obtain a detectable and/or quantifiable signal; the labeling of the primers or of the probes according to the invention is carried out with radioactive elements or with nonradioactive molecules. Among the radioactive isotopes used, mention may be made of $^{32}$P, $^{33}$P, $^{35}$S or $^{3}$H. The nonradioactive entities are selected from ligands such as biotin, avidin, streptavidin or digoxigenin, haptenes, dyes, and luminescent agents such as radioluminescent, chemoluminescent, bioluminescent, fluorescent or phosphorescent agents.

In one embodiment, the sequencing is single-molecule sequencing which allows complete genomes to be sequenced on a single microarray chip in a single sequencing reaction. The principle of this technology is that large numbers of short sequences are immobilized as single strands on a surface where they can be individually visualized with a sensitive microscope and camera. Every fragment is then sequenced simultaneously with fluorescent nucleotides and a polymerase enzyme, and the sequence information from all of the molecules is recorded simultaneously within a single camera frame.

The invention also provides methods which employ (usually, analyze) the products of the methods of the invention, such as preparation of libraries (including cDNA and differential expression libraries); sequencing, detection of sequence alteration(s) (e.g., genotyping or nucleic acid mutation detection); determining presence or absence of a sequence of interest; gene expression profiling; differential amplification; preparation of an immobilized nucleic acid (which can be a nucleic acid immobilized on a microarray), and characterizing (including detecting and/or quantifying) mutations in nucleic acid products generated by the methods of the invention.

In one embodiment, the invention provides methods of generating mutations in newly synthesized nucleic acid molecules in a cell, said method comprising (a) contacting a cell with a thiol-containing nucleoside or nucleobase, (b) isolating nucleic acid molecules from the cell, and (c) contacting the nucleic acid molecules with an oxidant and a nucleophile.

In some embodiments, the invention provides methods of analyzing newly synthesized nucleic acid molecules in a cell, said methods comprising (a) contacting a cell with a thiol-containing nucleoside or nucleobase, (b) isolating nucleic acid molecules from the cell, (c) contacting the nucleic acid molecules with an oxidant and a nucleophile, (d) sequencing the isolated nucleic acid molecules, and (e) analyzing the sequencing reads to identify those reads containing a mutation generated by conversion of a thiol-containing nucleoside or nucleobase of the invention.

In one embodiment, the thiol-containing nucleoside or nucleobase is one of 4-thiouricil, s$^4$U, s$^6$G, s$^6$dG and s$^4$T.

In one embodiment, the method relates to identification of newly transcribed RNA molecules. Therefore, in one embodiment, the thiol-containing nucleoside or nucleobase is one that can be incorporated into nascent transcripts in a cell. In one embodiment, the thiol-containing nucleoside is generated in the cell from a thiol-containing nucleobase. In one embodiment, the thiol-containing nucleobase is 4-thiouricil, which is converted into $s^4U$. In one embodiment, the thiol-containing nucleoside is $s^4U$ and the mutation generated by the method of the invention is a U to C mutation in amplification products generated from nascent transcripts. In one embodiment, the thiol-containing nucleoside is one of $s^6G$ and $s^6dG$ and the mutation generated by the method of the invention is a G to A mutation in amplification products generated from nascent transcripts.

In one embodiment, the method relates to identification of newly replicated DNA molecules. Therefore, in one embodiment, the thiol-containing nucleoside or nucleobase is one that can be incorporated into newly replicated DNA molecules in a cell. In one embodiment, the thiol-containing nucleoside is $s^4T$ and the mutation generated by the method of the invention is a T to C mutation in amplification products generated from newly replicated DNA. In one embodiment, the thiol-containing nucleoside is one of $s^6G$ and $s^6dG$ and the mutation generated by the method of the invention is a G to A mutation in amplification products generated from newly replicated DNA.

In one embodiment, a thiol-containing nucleoside or nucleobase is provided in a concentration sufficient for at least one thiol-containing nucleoside to be incorporated into a newly synthesized nucleic acid molecule. In one embodiment, a thiol-containing nucleoside or nucleobase is provided at a concentration of at least 100 nM, at least 500 nM, at least 1 µM, at least 5 µM, at least 10 µM, at least 50 µM, at least 100 µM, at least 500 µM, at least 1 mM, at least 5 mM, at least 10 mM, at least 50 mM, at least 100 mM, at least 500 mM, at least 1M or greater than 1M.

In one embodiment, a thiol-containing nucleoside or nucleobase is provided for a time period sufficient for at least one thiol-containing nucleoside or nucleobase to be incorporated into a newly synthesized nucleic acid molecule. In one embodiment, a thiol-containing nucleoside or nucleobase is provided for at least 1 minute, at least 5 minutes, at least 10 minutes, at least 20 minutes, at least 30 minutes, at least 40 minutes, at least 50 minutes, at least 60 minutes, at least 70 minutes, at least 80 minutes, at least 90 minutes, at least 100 minutes, at least 120 minutes, at least 150 minutes, at least 180 minutes, at least 210 minutes, at least 240 minutes, or greater than 240 minutes.

In one embodiment, the thiol-containing nucleoside or nucleobase is provided for a time period sufficient to incorporate the thiol-containing nucleoside into at least 50%, at least 60%, at least 70%, at least 80%, at least 90%, at least 95%, at least 98%, at least 99%, or greater than 99% of newly synthesized nucleic acid molecules and then removed from the media. In one embodiment, the thiol nucleoside is added for at least 2 hours, at least 4 hours, at least 8 hours, at least 12 hours, at least 24 hours, at least 48 hours, at least 36 hours, or greater than 36 hours.

In one embodiment, a thiol-containing nucleoside or nucleobase is provided for a limited time period such that it is only incorporated into recently synthesized nucleic acid molecules. In one embodiment, a thiol-containing nucleoside or nucleobase is provided for less than 5 hours, less than 4 hours, less than 3 hours, less than 2 hours or less than 1 hour.

In one embodiment, the time for which a cell is contacted with a thiol-containing nucleoside or nucleobase and the concentration of the nucleoside or nucleobase can be varied based on the experimental design (e.g., the number of newly synthesized nucleic acid molecules having an incorporated thiol-containing nucleoside or nucleobase and/or the time frame during which newly synthesized nucleic acid molecules are being evaluated.) A person of skill in the art would easily understand how to vary these parameters to achieve a desired outcome based on the disclosure herein.

In various embodiments, the oxidant is at least one of hydrogen peroxide, sodium iodate, sodium periodate, and meta-Chloroperoxybenzoic acid.

In various embodiments, the nucleophile is at least one of TFEA, benzylamine, $MeONH_2$, aniline, hydrazine, ammonia, 1,1-Dimethylethylenediamine, and 4-(Trifluoromethyl)benzylamine.

In various embodiments, the oxidant is meta-Chloroperoxybenzoic acid and the nucleophile is at least one of TFEA, benzylamine, $MeONH_2$, aniline, ammonia, and 4-(Trifluoromethyl)benzylamine. In one embodiment, the oxidant is sodium iodate and the nucleophile is $MeONH_2$. In various embodiments, the oxidant is sodium periodate and the nucleophile is one of TFEA, benzylamine, and aniline. In one embodiment, the oxidant is hydrogen peroxide and the nucleophile is TFEA.

In one embodiment, the nucleic acid molecules are contacted with a solution comprising a nucleophile and an oxidant is subsequently added thereto. In one embodiment, an oxidant is added dropwise to a solution containing isolated nucleic acid molecules and a nucleophile.

In one embodiment, a nucleophile is provided in a concentration sufficient for conversion of at least one thiol-containing nucleoside or nucleobase to a convertible nucleoside intermediate. In one embodiment, a nucleophile is provided at a concentration of at least 100 nM, at least 500 nM, at least 1 µM, at least 5 µM, at least 10 µM, at least 50 µM, at least 100 µM, at least 500 µM, at least 1 mM, at least 5 mM, at least 10 mM, at least 50 mM, at least 100 mM, at least 500 mM, at least 1M or greater than 1M.

In one embodiment, an oxidant is provided in a concentration sufficient for conversion of at least one convertible nucleoside intermediate into an analog of a different base (i.e., a cytidine analog for $s^4T$ or $s^4U$ or an adenine analog for $s^6G$ or $s^6dG$). In one embodiment, an oxidant having a concentration of at least 100 nM, at least 500 nM, at least 1 µM, at least 5 µM, at least 10 µM, at least 50 µM, at least 100 µM, at least 500 µM, at least 1 mM, at least 5 mM, at least 10 mM, at least 50 mM, at least 100 mM, at least 500 mM, at least 1M or greater than 1M is provided drop-wise to a solution comprising a nucleic acid molecule and a nucleophile.

Methods of analyzing the sequencing reads may include the use of bioinformatics methods for filtering, aligning, and characterizing sequencing reads. Such bioinformatics methods may include, but are not limited to, filtering of sequencing reads for unique sequences, trimming of sequencing reads (e.g., to remove sequencing adaptor sequences or low quality bases), filtering of sequencing reads for reads greater than a minimum length, generation of contigs and alignment of sequencing reads to a reference genome. In some embodiments, bioinformatics methods include methods for identifying mutation sites in sequencing reads (e.g., methods to determine sites of T-to-C mutations). In some embodiments, the methods include processing an aligned BAM file in R using Rsamtools and determining the sites and numbers of mutations.

In some embodiments, the methods include one or more measures to remove from the analysis those specific mutations that are determined to not be a result of the method of the invention. Exemplary mutations that are determined to not be a result of the method of the invention include, but are not limited to, mutations at positions with a base quality score of less than or equal to 55 that are less than four nucleotides from the end of the sequencing read, and sites of common SNPs or RNA modifications. Methods for identifying sites of common SNPs or RNA modifications include, but are not limited to, identifying T-to-C SNP sites or G-to-A SNP sites in control samples using bcftools, identifying locations where T-to-C or G-to-A mutations are high in non-treated controls, and identifying sites where T-to-C or G-to-A mutations are anomalously high relative to other sites within the same gene.

In one embodiment, the method of the invention further includes the step of analyzing and characterizing those sequencing reads containing a mutation generated by conversion of a convertible nucleoside of the invention as being generated from a nascent mRNA transcript. In one embodiment, the step of analyzing and characterizing sequencing reads containing a mutation is performed using at least one bioinformatics method. Bioinformatics methods appropriate for use in analyzing and characterizing sequencing reads may include, but are not limited to, methods to examine the distribution of reads with T-to-C or G-to-A mutations, methods to make genome-coverage tracks, methods to normalize the data, methods for generating heatmaps, or any other tool known in the art or developed for the purpose of identifying and analyzing mutations in sequencing data.

Kits

The present invention also includes kits useful in the methods of the invention. Such kits comprise components useful in any of the methods described herein, including for example, at least one of a thiol-containing nucleoside or nucleobase, a reagent for performing oxidative-nucleophilic-aromatic-substitution chemistry, primers, probes, oligonucleotide arrays, restriction enzymes, antibodies, allele-specific oligonucleotides, means for amplification of a subject's nucleic acids, means for reverse transcribing a subject's RNA, means for analyzing a subject's nucleic acid sequence, and instructional materials. For example, in one embodiment, the kit comprises components useful for one or more of the generation, detection and quantification of at least one mutation in a nucleic acid molecule. In various embodiments, at least one control nucleic acid molecule is contained in the kit, such as a positive control, a negative control, or a nucleic acid molecule useful for assessing the quality of a sequencing run.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Example 1

TimeLapse-Seq Adds a Temporal Dimension to RNA Sequencing

Global analyses of cellular RNAs provide a detailed portrait of the biological state of a sample. RNA sequencing (RNA-seq) offers a snapshot of cellular RNA populations, but does not provide temporal information about the sequenced RNA. Time Lapse Sequencing (TimeLapse-seq), a chemical method to encode temporal information into an RNA sequencing experiment, has been developed and is demonstrated herein. In TimeLapse-seq, a sample is treated with $s^4U$, a metabolic label that is incorporated into new RNAs (FIG. 1A). Nucleic acids that have a thiol-containing nucleoside (e.g., $s^4U$ or $s^4T$) in their composition are treated with oxidative-nucleophilic-aromatic-substitution chemistry (i.e., TimeLapse chemistry), comprising an oxidant (e.g., $NaIO_4$) in the presence of a nucleophile (e.g., $CF_3CH_2NH_2$). These reaction conditions lead to the conversion of a base from one effective identity (e.g., T) into a base of another effective identity (e.g., C). The conversion of the thiolated base into another leading to apparent U-to-C mutations that mark new transcripts can be observed by assays including sequencing. TimeLapse-seq is used to reveal heat-shock-induced dynamics, unexpected levels of post-transcriptional regulation, and differences in global RNA turnover that are concealed in traditional RNA-seq, illustrating the opportunities provided by incorporating a temporal dimension into RNA sequencing.

The results presented herein provide 1) experimental Mass spectrometry data demonstrating the conversion of $s^4U$ and $s^4T$ to amine containing C-analogues, 2) an experimental restriction enzyme digestion assay demonstrating the high efficiency of this chemistry under a number of conditions (>70% conversion) and the compatibility of this chemistry with oligoribonucleotides and enzymatic manipulation, 3) exemplary targeted sequencing data showing these conditions lead to conversion only when all components are present ($s^4U$-RNA, oxidant and nucleophile), 4) exemplary RNA-Seq data from metabolically labeled cellular RNA with and without chemical treatment demonstrating that this approach captures different RNA turnover rates for different cellular RNAs, and 5) experimental data demonstrating that this approach can reveals cryptic dynamics of the RNA pool (e.g., changes in RNA upon cellular heatshock.)

Further this assay captures both "labeled" (i.e., nucleic acid molecules that incorporated a $s^4U$ or $s^4T$) and those that are "unlabeled." This demonstrates that only a subpopulation of RNA is labeled, and further provides an advantage over pull-down methods that only capture "labeled" nucleic acid molecules (e.g., BrdU based sequencing methods.)

The materials and methods are now described

Materials

All commercially available materials were purchased from the indicated suppliers and used without further purification. 4-thiouridine ($s^4U$), and Meta-chloroperoxybenzoic acid (mCPBA) were purchased from Alfa Aesar (Haverhill, Mass.). 4-thiouridine-5'-triphosphate ($s^4UTP$) was purchased from TriLink BioTechnologies (San Diego, Calif.). 2,2,2-trifluoroethylamine (TFEA), sodium acetate, EDTA, Tris hydrochloride, acrylamide/bis-acrylamide 30% solution, and phenol: chloroform: isoamyl (25:24:1) were purchased from Sigma Aldrich (St. Louis, Mo.). Sodium periodate ($NaIO_4$) and ammonium bicarbonate were purchased from Acros Organics (Geel, Belgium). Dithiothreitol (DTT) was purchased from Thermo Fisher Scientific (Waltham, Mass.). Phosphate buffered saline (PBS) was purchased from AmericanBio (Natick, Mass.). Dulbecco's Modified Eagle Medium (DMEM), fetal bovine serum (FBS), Trizol reagent, TURBO DNase and SuperScript III Reverse Transcriptase were purchased from Life Technologies (Carlsbad, Calif.). KAPA Taq Ready Mix was purchased from Kapa Biosystems Inc (Wilmington, Mass.). Penicillin-streptomycin (P/S) and 33mm 0.45 μm PDVF syringe filters were purchased from EMD Millipore (Billerica, Mass.). NotI HF restriction enzyme and NEBNext Ultra Directional RNA Library Prep Kit were purchased from New England Biolabs (Ipswich, Mass.). SMARTer Stranded Total RNA Kit (Pico Input) was purchased from Takara Bio USA (Mountain View, Calif.). Hypersil Gold 3 um, 160×2.1 mm column was purchased from Thermo Fisher Scientific (Waltham, Mass.).

Instrumentation

LC-MS measurements were carried out on an Agilent 6550A Q-TOF. Analysis of fluorescent RNAs was carried out on a GE Healthcare Typhoon FLA 9500. RNA-seq was performed on Illumina HiSeq 2500 and Illumina HiSeq 4000 instruments.

LC-MS Analysis of Nucleosides

To a solution of $s^4U$ (50 μM) and ammonium bicarbonate (10 mM) was added TFEA (600 mM). mCPBA (10 mM) was dissolved in ethanol and added dropwise to the reaction mixture. After 1 hour at 25° C. the reaction was analyzed by reverse-phase LC-MS with a Hypersil GOLD column (Thermo, 3 μm, 160×2.1 mm) using chromatography conditions as previously described (Duffy et al., 2015, Mol Cell, 59:858-866). Masses were collected using positive ion mode and extracted ions were identified and integrated using Agilent MassHunter software.

Nuclear Magnetic Resonance Analysis of Nucleobase Chemistry 4-thiouracil (4.3 mg, 1 equiv) was dissolved in DMSO-$d_6$, and TFEA (3.4 μl, 1.3 equiv) was added to the solution. After mixing, a solution of $NaIO_4$ in DMSO-$d_6$ (12.3 mg, 1.7 eq) was added to the nucleobase and amine solution, and the reaction was allowed to proceed at 45° C. for 4 hours. $^1H$ NMR spectra were processed using the MestReNova software.

NotI Restriction Endonuclease Assay

An RNA containing a single $s^4U$ was in-vitro transcribed (IVT) from a synthesized DNA template strand using T7 RNA polymerase and $s^4UTP$ in place of UTP for 16 hours at 37° C. The reaction mixture was treated with TURBO DNase for 1 hour at 37° C. The RNA was purified using denaturing PAGE, the resulting band was gel purified by crushing the gel slice and soaking it in extraction buffer (1 mM EDTA, 1 mM DTT, 20mM Tris, 300 mM NaOAc pH 5.2) at 4° C. for 4 hours. The supernatant was passed through a 0.45 μM syringe filter, and the RNA was ethanol precipitated and washed with 75% ethanol prior to resuspension in nuclease-free water.

Figure 1D:
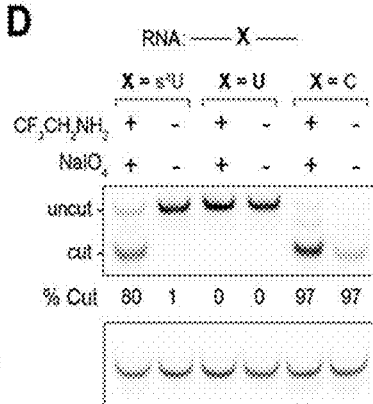
Figure 1E:
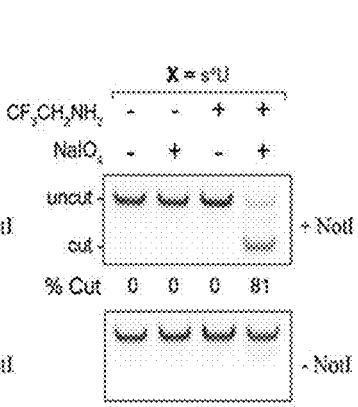
Figure 2:
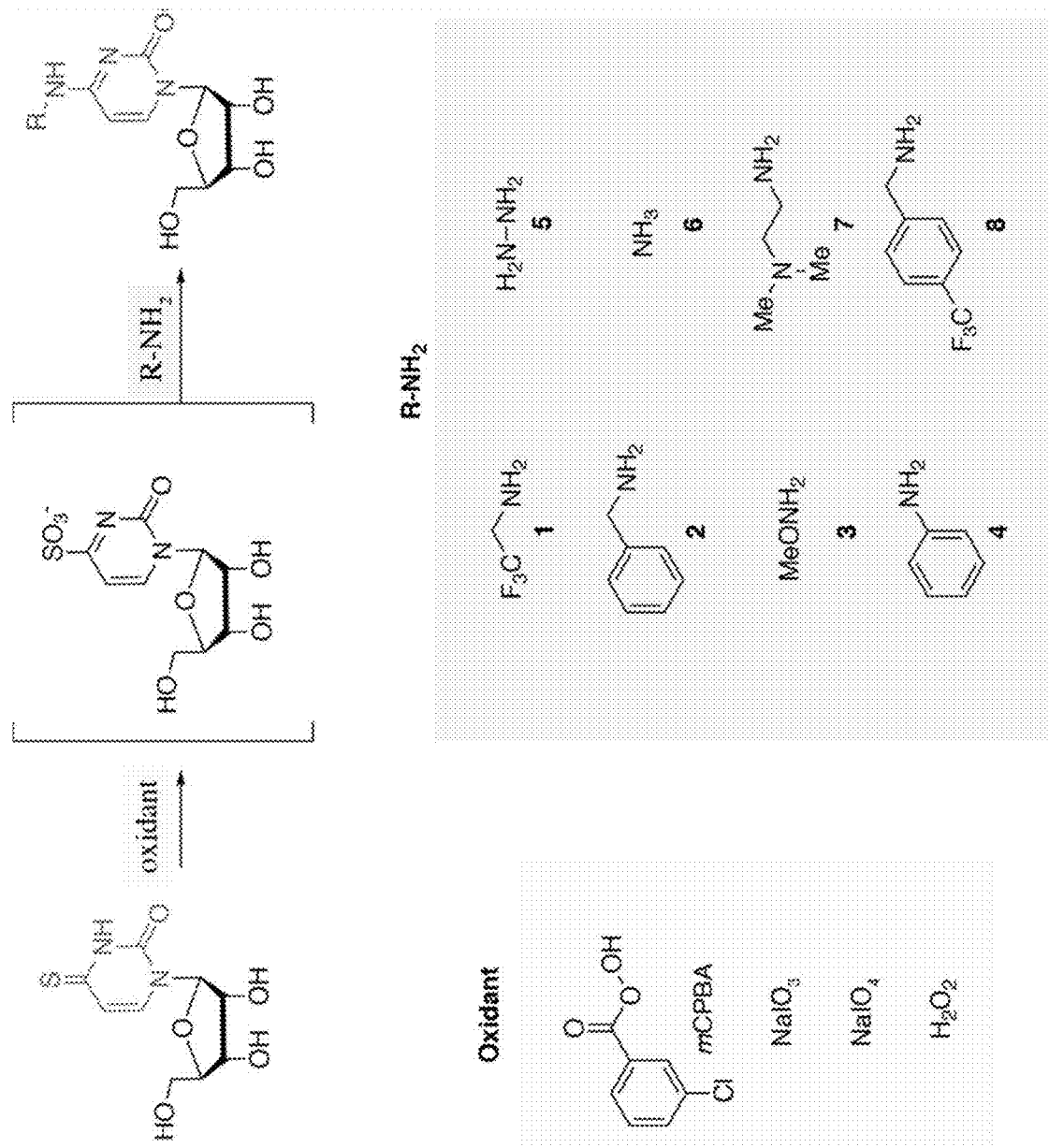
FIG. 2 depicts the results of example experiments demonstrating the development of conditions to convert 4-thiouridine ($s^4U$) into a convertible nucleoside. An LC-MS assay was used to qualitatively analyze reactions of $s^4U$ with different combinations of oxidants and nucleophiles (R—$NH_2$). In all cases, $s^4U$ (50 μM) was incubated with indicated amine and oxidant for 1 hour, the reaction products were analyzed by reversed-phase LC-MS and extracted ion chromatograms were analyzed for the product masses. Extracted ions were observed for the desired products for mCPBA with nucleophiles 1, 2, 3, 4, 6, 8; $NaIO_3$ with nucleophile 3; $NaIO_4$ with nucleophiles 1, 2, 4; $H_2O_2$ with nucleophile 1. Note that $NaIO_4$ also leads to oxidation of the vicinal diol of the free nucleoside, although this reaction does not influence downstream analyses in TimeLapse-seq.

IVT RNAs were screened for optimal TimeLapse chemistry as follows: RNA (120 ng) was added to a mixture of amine and water. A solution of oxidant was then added drop wise and the reaction mixture was incubated at the temperature and time indicated (see FIG. 1D and FIG. 2). The RNA was then ethanol precipitated and washed three times with 75% ethanol prior to resuspension in nuclease-free water.

After chemical treatment, IVT RNA (50 ng) was reverse transcribed with SuperScript III according to the manufactures directions. The cDNA was PCR amplified for 30 cycles with a fluorescent forward primer, then amplified an additional 2 cycles using ⅕ of the previous PCR reaction material with non-labeled primers (Table 1). The amplified PCR product was then incubated with NotI HF for 1 hour at 37° C. The fluorescent products were visualized using native PAGE followed by scanning with a Typhoon FLA imager and the proportion of cut product was determined using ImageJ.

TABLE 1

In vitro transcription (IVT) templates and restriction enzyme (RE) assay primer sequences

| Identifier | SEQ ID NO: | Sequence |
|---|---|---|
| IVT template | 23 | CTTGCGTTTCTCTCGTCCTT ctgtcttgctgttgttcGCG ACCGCcctgtGCGGTTGTGT CTTTTGTCCTGCCTATAGTG AGTCGTATTAATTTC |
| IVT positive control template | 24 | CTTGCGTTTCTCTCGTCCTT ctgtcttgctgttgttcGCG GCCGCcctgtGCGGTTGTGT CTTTTGTCCTGCCTATAGTG AGTCGTATTAATTTC |
| IVT T7 promoter | 19 | GAAATTAATACGACTCACTA TA |
| RE RT and reverse primer | 20 | CTTGCGTTTCTCTCGTCCTT |
| RE fluorescent forward primer | 21 | /5Cy5/AGGACAAAAGACAC AACCGC |
| RE forward primer | 22 | AGGACAAAAGACACAACCGC |
| Primer extension RT | 25 | /5Cy5/CTTGCGTTTCTCTC GTCCTT |

Targeted TimeLapse Sequencing

Mouse embryonic fibroblast (MEF) cells were grown at 37° C. in DMEM containing 10% FBS and 1% P/S. At approximately 60% confluence, the media was replaced with media supplemented with $s^4U$ (700 μM). After two hours, the cells were rinsed with PBS, resuspended in TRIzol reagent, and stored overnight at −80° C. Following chloroform extraction, total RNA was ethanol precipitated with 1 mM DTT and washed with 75% ethanol. Total RNA was resuspended and treated with TURBO DNase, then extracted with acidic phenol:chloroform:isoamyl alcohol and ethanol precipitated and washed as described above. Isolated total RNA was added to a mixture of TFEA (600 mM), EDTA (1 mM) and sodium acetate pH 5.2 (100 mM) in water. A solution of $NaIO_4$ (10 mM) was then added drop wise and the reaction mixture was incubated for 1 hour at 45° C. Potassium chloride (300 mM) and sodium acetate pH 5.2 (300 mM) were added and the reaction mixture was allowed to stand on ice for 10 minutes prior to centrifugation (>10000 rpm, 30 minutes, 4° C.) to precipitate remaining periodate. The RNA in the supernatant was then ethanol precipitated and washed three times with 75% ethanol prior to resuspension in nuclease-free water. The chemically treated RNAs were then reverse transcribed using a mixture of mouse Actb and Gapdh-specific mRNA RT primers (Table 2). The resulting cDNA was then amplified with Phusion polymerase using corresponding forward PCR primers to produce PCR amplicons approximately 150 nucleotides (nt) in length. An Illumina sequencing library was constructed using the NEBNext Ultra Directional RNA Library Prep kit. Paired-end 75bp sequencing was performed on an Illumina HiSeq 2500 instrument. Sequencing reads were trimmed to remove adaptor sequences and aligned to the mouse genome using Bowtie2. Aligned reads were parsed to identify mutations at each nucleotide position in the Actb and Gapdh mRNAs using analyses adapted from (Siegfried et al., 2014, Nat Methods, 11:959-965). Raw mutation probabilities were determined by dividing the number of recorded mutation events by the number of reads at that position. Mutation probabilities were normalized to appropriate control samples and filtered by read depth (only positions with depth >3,000 were included in analyses). Analyses and figure plot generation were performed in R using the tidyverse, corrplot, and multiplot packages (Siegfried et al., (2014) Nat Methods, 11:959-965; Wei et al., (2017), Visualization of a Correlation Matrix, Version 0.84). The enrichment in mutation rates was tested for significance using a two-sided Wilcoxon test. Targeted sequencing was performed in duplicate using biologically distinct samples.

TABLE 2

Targeted TimeLapse-seq primer sequences

| Identifier | SEQ ID NO: | Sequence |
|---|---|---|
| mActB1 Forward Sequence | 1 | CTACACGACGCTCTTCCGATCTNNNNN ACTGAGCTGCGTTTTACACCC |
| mActB2 Forward Sequence | 2 | CTACACGACGCTCTTCCGATCTNNNNN AATTTCTGAATGGCCCAGGTCT |
| mActB3 Forward Sequence | 3 | CTACACGACGCTCTTCCGATCTNNNNN ATGGTGGGAATGGGTCAGAAGG |
| mActB4 Forward Sequence | 4 | CTACACGACGCTCTTCCGATCTNNNNN TGAAGTGTGACGTTGACATCCG |
| mGapdh1 Forward Sequence | 5 | CTACACGACGCTCTTCCGATCTNNNNN TCCGTCGTGGATCTGACGTG |
| mGapdh2 Forward Sequence | 6 | CTACACGACGCTCTTCCGATCTNNNNN CTCTTCCACCTTCGATGCCG |
| mGapdh3 Forward Sequence | 7 | CTACACGACGCTCTTCCGATCTNNNNN AGGACACTGAGCAAGAGAGGC |
| mGapdh4 Forward Sequence | 8 | CTACACGACGCTCTTCCGATCTNNNNN CAGCAATGCATCCTGCACCA |
| hMYC1 Forward Sequence | 26 | CTACACGACGCTCTTCCGATCTNNNNN CTTGGCGGGAAAAAGAACGG |
| hMYC2 Forward Sequence | 27 | CTACACGACGCTCTTCCGATCTNNNNN GCATCCACGAAACTTTGCCC |
| hMYC3 Forward Sequence | 28 | CTACACGACGCTCTTCCGATCTNNNNN TACTGCGACGAGGAGGAGAA |
| hMYC4 Forward Sequence | 29 | CTACACGACGCTCTTCCGATCTNNNNN CAGGACTGTATGTGGAGCGG |
| mActB1 Reverse Sequence | 9 | CAGACGTGTGCTCTTCCGATCTTCCTG AGTCAAAAGCGCCAAAAC |
| mActB2 Reverse Sequence | 10 | CAGACGTGTGCTCTTCCGATCTGGTGT GGCACTTTTATTGGTCTCAAGTC |
| mActB3 Reverse Sequence | 11 | CAGACGTGTGCTCTTCCGATCTGCCAC ACGCAGCTCATTGTAG |
| mActB4 Reverse Sequence | 12 | CAGACGTGTGCTCTTCCGATCTGAGGA GCAATGATCTTGATCTTCATGG |
| mGapdh1 Reverse Sequence | 13 | CAGACGTGTGCTCTTCCGATCTCATCG AAGGTGGAAGAGTGGG |
| mGapdh2 Reverse Sequence | 14 | CAGACGTGTGCTCTTCCGATCTGGTGG GTGGTCCAGGGTTTC |
| mGapdh3 Reverse Sequence | 15 | CAGACGTGTGCTCTTCCGATCTGTGGG TGCAGCGAACTTTATTG |
| mGapdh4 Reverse Sequence | 16 | CAGACGTGTGCTCTTCCGATCTACAGC TTTCCAGAGGGGCC |
| hMYC1 Reverse Sequence | 30 | CAGACGTGTGCTCTTCCGATCTTATTC GCTCCGGATCTCCCT |
| hMYC2 Reverse Sequence | 31 | CAGACGTGTGCTCTTCCGATCTCCTTT CAGAGAAGCGGGTCC |
| hMYC3 Reverse Sequence | 32 | CAGACGTGTGCTCTTCCGATCTCGAAG GGAGAAGGGTGTGAC |
| hMYC4 Reverse Sequence | 33 | CAGACGTGTGCTCTTCCGATCTGGTAC AAGCTGGAGGTGGAG |
| Forward PCR Amplification primer | 17 | CAGACGTGTGCTCTTCCGATC |
| Reverse PCR Amplification primer | 18 | CTACACGACGCTCTTCCGATCT |

Targeted TimeLapse-seq of K562 RNA was performed similarly with the following exceptions. Cells were grown at 37° C. in RPMI containing 10% FBS and 1% P/S. At approximately 50% confluence, the media was supplemented with a range of $s^4U$ concentrations (10-40 μM) for 1 hour. Total RNA was isolated and chemically treated as described previously. The chemically treated RNAs were then reverse transcribed using a mixture of human MYC-specific mRNA RT primers. A targeted sequencing library was prepared and analyzed as described above.

Cell Viability.

MEF cells were grown at 37° C. in DMEM containing 10% FBS and 1% P/S. Cells were plated at $10^6$ cells/mL in a 96-well microtiter plate and allowed to recover overnight. Cells were then treated in triplicate with increasing concentrations of $s^4U$ (0-1 mM) for 1 hour, and the ATCC MTT Cell Proliferation Assay kit was used according to manufacturer's instructions to assess cell viability.

Transcriptome-Wide TimeLapse-seq

MEF cells were grown at 37° C. in DMEM containing 10% FBS and 1% P/S. At approximately 60% confluence, the media was replaced and supplemented with $s^4U$ (1 mM). The cells were incubated at 37° C. for 1 hour, at which point total RNA was isolated and chemically treated as described in the targeted sequencing section. For heat shock analyses, at approximately 60% confluence, the media was replaced and supplemented with $s^4U$ (1 mM), and heat shocked cells were incubated at 42° C. for 1 hour. RNA was prepared as described for the Targeted TimeLapse-seq libraries. For each sample, 10 ng of total RNA was used to construct a sequencing library using the Clontech SMARTer Stranded Total RNA-Seq kit (Pico Input) with ribosomal cDNA depletion. Paired-end 100 bp sequencing was performed on an Illumina HiSeq 4000 instrument. TimeLapse-seq was performed in duplicate using biologically distinct samples for experimental samples both with and without heat shock. Raw and processed sequencing data have been submitted to the GEO database.

TT-TimeLapse-seq

K562 cells were grown at 37° C. in RPMI containing 10% FBS and 1% P/S. At approximately 50% confluence, the media was supplemented with $s^4U$ (1 mM). The cells were incubated at 37° C. for 5 minutes, at which point total RNA isolation and genomic DNA depletion were performed as described above. 50 μg of total RNA was subjected to MTS chemistry, followed by biotinylation and streptavidin enrichment essentially as previously described (Duffy et al., (2015) Mol Cell, 59:858-866) with the following modification: after SAV beads were washed three times with high-salt wash buffer (1 M NaCl, 100 mM Tris pH 7.4, 10 mM EDTA, 0.05% Tween), beads were incubated in TE buffer (10 mM Tris pH 7.4, 1 mM EDTA) at 55° C. for 15 min, followed by two washes with prewarmed 55° C. TE buffer. After elution from SAV beads, enriched RNA was purified using one equivalent volume of Agencourt RNAclean XP beads according to manufacturer's instructions instead of purification by ethanol precipitation. Enriched RNA and input RNA were chemically treated as previously described. Chemically treated RNA was purified using 1 equivalent volume of Agencourt RNAclean XP beads according to manufacturer's instructions. Purified material was then incubated in a reducing buffer (10 mM DTT, 100 mM NaCl, 10 mM Tris pH 7.4, 1 mM EDTA) at 37° C. for 30 min, followed by a second RNAclean bead purification. For each sample, all enriched material or 10 ng of total RNA input was used to construct a sequencing library using the Clontech SMARTer Stranded Total RNA-Seq kit (Pico Input) with ribosomal cDNA depletion. Paired-end 150 bp sequencing was performed on an Illumina HiSeq 4000 instrument. TimeLapse-seq was performed in duplicate using biologically distinct samples for experimental samples. Raw and processed sequencing data have been submitted to the GEO database.

Samples for TimeLapse-seq Analysis of K562 mRNA

K562 cells were grown as previously described. At approximately 50% confluence, the media was supplemented with s$^4$U (100 μM). The cells were incubated at 37° C. for 4 h, at which point total RNA was isolated using the RNeasy mini kit with the following modifications: buffers RLT and RPE were supplemented with 1% final 2-mercaptoethanol (BME); an additional 80% EtOH wash was performed after the RPE step; and the column was spun at maximum speed for 5 minutes to dry before elution with water. The isolated RNA was then chemically treated and purified as previously described. For each sample, 10 ng of total RNA was used to construct a sequencing library using the Clontech SMARTer Stranded Total RNA-Seq kit (Pico Input) with ribosomal cDNA depletion. Paired-end 150 bp sequencing was performed on an Illumina HiSeq 4000 instrument. TimeLapse-seq was performed in duplicate using biologically distinct samples for experimental samples. Raw and processed sequencing data have been submitted to the GEO database.

Transcriptional Inhibition

K562 cells were grown as described above. At approximately 50% confluence, cells were treated in duplicate with actinomycin D (2 μg/mL final) for 30 min, 1 hour, 3 hours, 5 hours, and 9 hours, or left untreated. Total RNA isolation and genomic DNA depletion were then performed as previously described. RT was performed using the SuperScript VILO cDNA synthesis kit, and qPCR was performed using primers specific to ACTB, DHX9, and ASXL1 (Table 3). qPCR ct values for DHX9 and ASXL1 were then averaged and normalized to those of ACTB for each timepoint. The normalized fraction remaining was estimated for each primer pair by dividing the relative abundance of each timepoint by the relative abundance at t=0.

TABLE 3 qPCR primer sequences

| Identifier | SEQ ID NO: | Sequence |
| --- | --- | --- |
| Rsrp1 (a) Forward Sequence | 34 | AAGTACAGGCGCTACTCACG |
| Rsrp1 (b) Forward Sequence | 35 | AAGATCCAGAACCAGGTCGC |
| Rsrp1 (c) Forward Sequence | 36 | TCCTTGGACAGCTAGGGGAT |
| Rsrp1 (d) Forward Sequence | 37 | GAGGGGTTTGTGTCCAGCAT |
| Hist1h1d (a) Forward Sequence | 38 | AAGAAGGCAGCAAAGAGTCCA |
| Hist1h1d (b) Forward Sequence | 39 | AAGCCTAAGAAGGCGACTGG |
| ACTB Forward Sequence | 40 | GGCATGGGTCAGAAGGATT |
| DHX9 Forward Sequence | 41 | CCGATTCCTCCATGCGAGTT |
| ASXL1 (Pair 1) Forward Sequence | 42 | TCGGATGCTCCAATGACACC |
| ASXL1 (Pair 2) Forward Sequence | 43 | ACCAGGCCCCTTCATCTTAAT |
| ASXL1 (Pair 3) Forward Sequence | 44 | GAAGCCCCGGCTTGAAGAT |
| ASXL1 (Pair 4) Forward Sequence | 45 | ATCCTCACCGACTGATTGCC |
| ASXL1 (Pair 5) Forward Sequence | 46 | TGCATTGCCTGGGGATTTGA |
| Rsrp1 (a) Reverse Sequence | 47 | GACGGCGACTTGTAGTACCT |
| Rsrp1 (b) Reverse Sequence | 48 | GCAGTGGCTTTGCTACGGAA |
| Rsrp1 (c) Reverse Sequence | 49 | CACGAATACCCGACTCCTGT |
| Rsrp1 (d) Reverse Sequence | 50 | ACCTCAACCATGAACGTCCC |
| Hist1h1d (a) Reverse Sequence | 51 | AGATTTTCAAAGCAGGACGCA |
| Hist1h1d (b) Reverse Sequence | 52 | TCTACTTCTTGCGAGGGGCA |
| ACTB Reverse Sequence | 53 | CACACGCAGCTCATTGTAGA |
| DHX9 Reverse Sequence | 54 | TCTGGCCTTCTACCGAGACA |
| ASXL1 (Pair 1) Reverse Sequence | 55 | CCTTCTGCCTCTATGACCTGC |
| ASXL1 (Pair 2) Reverse Sequence | 56 | TCCCAAGCTTACAGCAGGTT |
| ASXL1 (Pair 3) Reverse Sequence | 57 | TGTGGCTTTTCGGTGTGAAC |
| ASXL1 (Pair 4) Reverse Sequence | 58 | CATGAGCCACCAAGCCCTAA |

TABLE 3-continued qPCR primer sequences

| Identifier | SEQ ID NO: | Sequence |
|---|---|---|
| ASXL1 (Pair 5) Reverse Sequence | 59 | CTCGAGATGGCACAGTCCAG |

Sequencing Alignment and Mutational Analysis

Reads were filtered for unique sequences using FastUniq (Xu et al., (2012) PLoS One, 7:e52249), trimmed using cutadapt (Martin, (2011) EMBnet.journal, 17:10-12) to remove illumine adaptor sequences filtering for reads greater than 20 nt (—minimum-length=20). Filtered reads were aligned to the mouse mm10genome, mouse GRCm38 or human GRCh38 genome and transcriptome annotations. Alignment to the mouse mm10 genome was performed using STAR 2.4.2a, using parameters adapted from the standard ENCODE pipeline (parameters: —genomeDir $GENOME_DIR, —runThreadN 20—outFilterType BySJout—outFilterMultimapNmax 5—alignSJoverhangMin 8—alignSJDBoverhangMin 1—outFilterMismatchNmax 999—outFilterMismatchNoverLmax 0.04—alignIntronMin 20—alignIntronMax 1000000—alignMatesGapMax 1000000—clip5pNbases 5). Only reads that aligned uniquely (flag: 83/163, 99/147), with MAPQ≥5, and without insertions (because of ambiguity in mutational analysis) were considered for further analysis. The statistics for the sequenced samples are provided in FIG. 29. Alignment to the mouse GRCm38 or human GRCh38 genome and transcriptome annotations using HISAT2 (Kim et al., (2015) Nat Methods, 12:357-360), using default parameters and -mp 4,2. Files were further processed with Picard tools including FixMateInformation, SortSam, and BuildBamIndex. The samtools (Li et al., (2009) Bioinformatics, 25:2078-2079) software was used to retain only reads that aligned uniquely (flag: 83/163, 99/147), with MAPQ≥2, and without insertions (because of ambiguity in mutational analysis) for further analysis.

Reads that uniquely map to UCSC transcripts (e.g., human GRCh38 version 26 (Ensembl 88) or mouse GRCm38 (p6)) were identified using HTSeq-count (Anders et al., 2015, Bioinformatics, 31:166-169) using union mode. Reads mapping to only mature isoforms or to anywhere in the gene body were determined separately and compared to identify intron-only reads. To determine the number of uridine residues inferred from each read, and the sites of T-to-C mutations, the aligned bam files were processed in R using Rsamtools and the sites and numbers of mutations were determined using a custom R script. Only mutations at positions with a base quality score of greater than 45 that were at least three nt from the end of the read were counted. Reads were excluded where there were greater than five T-to-C mutations, and these mutations did not account for at least one-third of the observed mutations (NM tag). Without adequate filtering, SNPs could interfere with TimeLapse analysis. To identify sites of SNPs (or RNA modifications that could be mis-identified as TimeLapse mutations), the following two strategies were used. First, T-to-C SNP sites were identified in control samples using bcftools and these sites were excluded from the subsequent analysis. Second, locations where T-to-C mutations were high in non-$s^4U$ treated controls were identified and excluded from the subsequent analysis. Once the putative SNPs were filtered, the total number of unique mutations in each read pair was counted. To examine the distribution of reads with each minimum number of T-to-C mutations, the bam files were filtered using Picard tools. To make genome-coverage tracks, STAR aligner (inputAlignmentsFromBam mode, outWigType bedGraph) was used and the tracks were normalized using values derived from RNA-seq analyses using values from DESeq2 (estimateSizeFactors) (Robinson et al., (2011) Nat Biotechnol, 29:24-26). Tracks were converted to binary format (toTDF, IGVtools) and visualized in IGV (Van Herreweghe et al., (2007) EMBO J, 26:3570-3580). Heatmaps were made using rlog transfored data (DESeq2) and the pheatmap package.

Secondary Structure Analysis.

Aligned reads from the 4 hour K562 TimeLapse-seq experiment overlapping the 5' stem loop of 7SK were extracted using samtools. A Python script developed for analyses of chemical probing data (RTEventsCounter; Sexton et al., (2017) Biochemistry, 56:4713-4721) was used to calculate the U-to-C mutation frequency for each uridine nucleotide. These frequencies were normalized by subtracting mutation frequencies of control samples that were not subjected to TimeLapse chemistry. The frequencies of mutations at each position were binned and mapped onto a conformational model of this region of human 7SK (Love et al., (2014) Genome Biol, 15:550). Each nucleotide was classified as either single stranded or basepaired. A two-sided Wilcoxon test was used to determine the significance of differences between mutation rates of the basepaired and single-stranded nucleotides.

Estimation of the Fraction of New Transcripts and Transcript Half-Lives

Two different models were used to examine the mutation distribution in TimeLapse-seq data set: a simpler Poisson model (which does not take into account the uridine content of different reads) and a binomial model that does take the number of uridines into account. Consistent results were obtained from both models. For the simpler Poisson model, for each sample ($s_j$), the distribution of T-to-C mutations ($Y_i$) was determined in each read, and the reads were grouped based on the transcripts to which they map. A negative control sample (no $s^4U$ treatment) was used to estimate the background rate of read pairs containing T-to-C mutations that map to each transcript. These frequencies depended on the cell line used (MEF samples required higher $s^4U$ treatment to obtain similar levels of mutations compared to K562 cells) as well as the sequencing experiment (different samples led to different background rates independent of chemistry or $s^4U$ treatment). The mutation rate and fraction of new transcripts was modeled as a two-component mixture of Poisson distributions with probability mass function:

$$f(y|\lambda_o, \lambda_n, \theta_n) = \theta_n \text{ Poisson } (y; \lambda_n) + (1-\theta_n) \text{ Poisson } (y; \lambda_o)$$

where $\theta_n$ is the fraction of new transcripts, $\lambda_O$ is the rate of background mutations (determined from $-s^4U$ controls), $\lambda_n$ is the rate of mutations found in new transcripts, and $y_i$ is the number of passing T-to-C mutations found in read i. Reasonable estimates of these values could be approximated by examining the mutation rates in fast turnover RNAs such as introns. To obtain more objective estimates of the global parameters $\lambda_O$ and $\lambda_n$ while allowing for low levels of transcript-to-transcript variability, a Bayesian hierarchical modeling approach was taken using RStan software (Version 2.16.2; Carpenter et al., (2017) J Stat Spftw, 76:1-32) that uses no-U-turn Markov Chain Monte Carlo (MCMC) sampling. To estimate a global mean and standard deviation (s.d.) for $\lambda_O$ and $\lambda_n$, weakly informative priors were used (see below). Gene-specific rates were estimated by drawing from the global mean and s.d., with a mixing rate with an uninformative prior ($\theta_n$~Uniform(0,1)) where the mixing rate ($\theta_n$) estimates the fraction of each transcript that was new:

Global parameters:

$$\lambda_{o,\mu} \sim \text{Normal}(\mu=0, \sigma=1)$$

$$\lambda_{n,\mu} \sim \text{Normal}(\mu=0, \sigma=10)$$

$$\lambda_{o,\sigma} \sim \text{Normal}(\mu=0, \sigma=10)$$

$$\lambda_{n,\sigma} \sim \text{Normal}(\mu=0, \sigma=10)$$

$$\lambda \sim \text{Normal}(\mu=\lambda_{o,\mu}, \sigma=\lambda_{o,\sigma})$$

$$I_s = \begin{cases} 0 & s \in \text{controls} \\ 1 & \text{otherwise} \end{cases}$$

$$g \in \{1, 2, \ldots, n_{genes}\}$$

Priors:

$$\lambda_{n,g} \sim \text{Normal}(\mu=\lambda_{n,\mu}, \sigma=\lambda_{n,\sigma})$$

$$\lambda_{o,g} \sim \text{Normal}(\mu=\lambda_{o,\sigma}, \sigma=\lambda_{o,\sigma})$$

for read $i \in \{1, 2, \ldots n_g\}$:

$$f_g(y_g \mid \theta_{ng}, \lambda_{og}, \lambda_{ng}) = \prod_{i=1}^{n_g}(Is\theta_{ng} \text{ Poisson}(y_i \mid \lambda_{ng}) + (1 - Is\theta_n)\text{Poisson}(y_i \mid \lambda_{og}))$$

Attempts to model entire TimeLapse-seq data sets using this approach were computationally challenging, but it was found that consistent results were obtained using 20 representative transcripts from each sample. The majority of these transcripts were chosen randomly from all reasonably expressed transcripts (>200 reads), but a few transcripts that were hand chosen to ensure the modeling included both fast and slow turnover RNAs such as $M_{yc}$ and Actb were included. The results using 20 transcripts were consistent with results from 200 transcripts. In the case of the MEF samples shown in FIG. 13, the $\lambda_o$ was estimated as 0.07 mutations/read (50% credible interval 0.062-0.074), and $\lambda_n$ was estimated as 2.3 mutations/read (2.298 mutation/read, 50% CI 2.10-2.30 for heat shock; 2.288 mutation/read, 50% CI 1.90-2.29 for untreated).

Once these global parameters were determined, they were used to estimate the fraction of new transcripts ($\theta_{new}$), using expectation maximization by minimizing the log likelihood using the nlm function in the MASS package in R:

$$-\sum_{i=1}^{n_g} \log(f(y; \theta_n, \lambda_o, \lambda_n))$$

The 95% Wald confidence interval was calculated using the Hessian (nlm option hessian=TRUE), to calculate:

$$\hat{\theta}_{new} \pm z_{0.975} \times \text{std eer}(\hat{\theta}_{new})$$

Figures 11A, 11B, 11C, 11D, 11E, 11F:
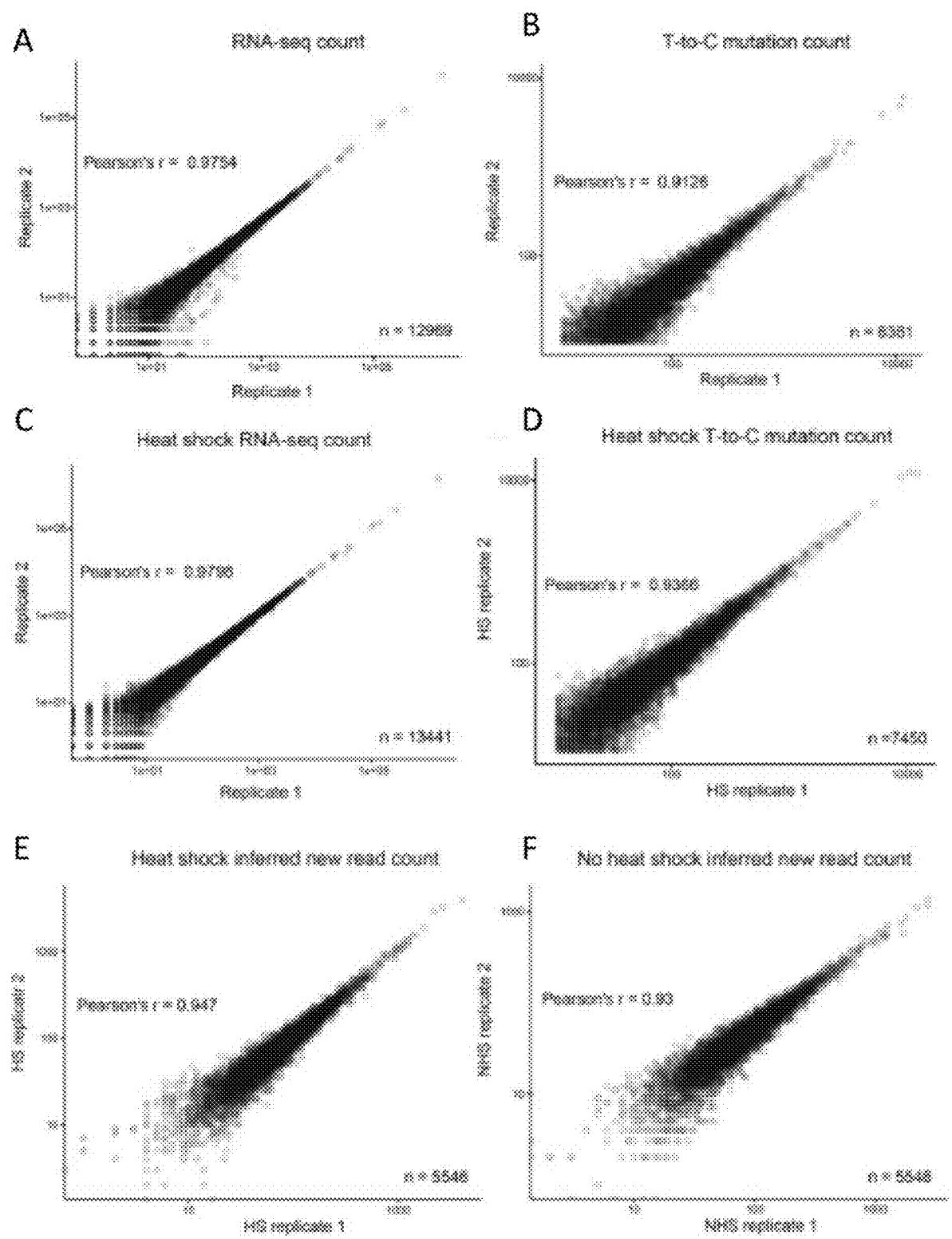
FIG. 11A through FIG. 11F, depicts the results of example experiments demonstrating a correlation analysis of TimeLapse-seq replicate reads and mutations.

To ensure the mutations were both s$^4$U-treatment and TimeLapse-chemistry dependent, only included transcripts where there was sufficient data (reads>100 counts in at least two samples), and where the fit converged ($-0.05<\theta_n<1.05$; hessian>1,000) were included. The inferred new read counts were determined by multiplying the estimated fraction of new transcripts by the total RNA-seq transcript count. Correlations between replicates were determined using the log10-transformed counts (FIG. 11). While the reproducibility of the data was generally high when all converged transcripts were included (Pearson's r>0.91), filtering for transcripts with at least 75 inferred new reads provided slightly more reproducible results (n=3,603, r=0.934), and this filter was used for further analysis.

To account for differences in the number of uridine residues in each read pair, an alternative model was used based on the binomial distribution. Specifically, the data were modeled as mixture of two binomial distributions:

$$f(y \mid \theta_n, p_o, p_n) = \theta_n \text{Binom}(y; p_n, n_{u,i}) + (1-\theta_n)\text{Binom}(y; p_o, n_{u,i})$$

where $p_o$, $p_n$ are the probabilities of mutation at each uridine nucleotide for old and new transcripts, and $n_u$ is the number of uridines observed for read i. To determine the global mutation rate, Bayesian hierarchical modeling was used as described above for the Poisson model but using a mixture of binomial distributions. From this analysis, the background mutation rate ($p_o$) was estimated to be 0.0012 mutations/uridine (50% CI 0.00121, 0.00123) and the mutation rate for new reads ($p_n$) to be 0.0332 mutations/uridine (50% CI 0.0329, 0.0335). In other words, ~0.1% of Us are mutated to C in pre-existing reads, and in new reads ~3% of Us are mutated to C. Using these global parameters, the distributions of individual genes were fit with nlm similarly to what is described above, except by minimizing the log likelihood of the binomial model instead:

$$-\sum_{i=1}^{n_g} \log(f(y; \theta_n, p_o, p_n, n_{u,i}))$$

Figures 13A, 13B, 13C, 13D, 13E, 13F, 13G, 13H:
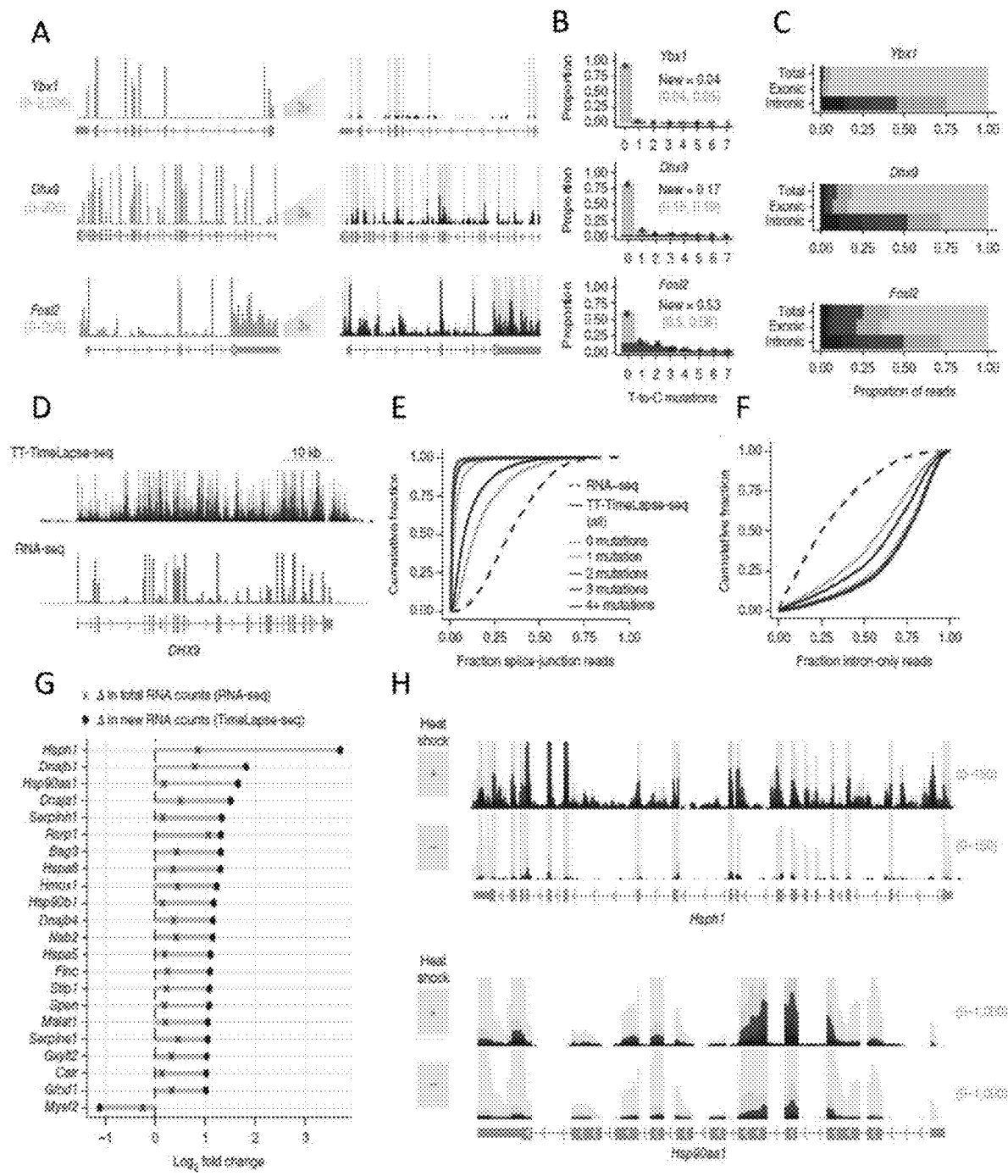
FIG. 13A through FIG. 13H, depicts the results of example experiments demonstrating a global analysis of steady-state and transient RNA dynamics using TimeLapse-seq.

In addition to computing the confidence interval using the hessian, the quality of the fit was examined by plotting the observed frequency of mutations in each replicate in the TimeLapse data (gray points in distribution plots) to a simulated distribution of the expected new and old reads based on the binomial model (FIG. 13B). Estimates of the fraction new were highly similar between those determined using the binomial model and the Poisson model.

To account for any specific loss of transcripts that might arise from biased loss of s$^4$U-RNA transcripts independent of TimeLapse chemistry, or TimeLapse-depended loss due to reverse-transcription termination, a means of estimating the loss of fast-turnover transcripts in the data was developed. This correction was only used when estimating transcript half-lives after observing a modest, but statistically significant loss of reads from high turnover RNAs (FIG. 11) estimate the fraction of new reads missing, the R package nlm was used to fit the equation:

$$s_y N_y \left(1 + \theta_n \left(\frac{x}{1-x}\right)\right) = s_o N_o$$

where $s_y$ and $s_o$ are scale factors that adjust for library sizes determined using DESeq2 with the total (RNA-seq) transcript counts for the experimental sample and control, respectively; $N_y$ and $N_o$ are the counts for each transcript; and $\theta_n$ is the unadjusted fraction new of each transcript. This equation was fit using transcripts where $0.8<\theta_n$ for K562 RNA, but $0.5<\theta_n$ in the case of MEF RNA (the shorter $s^4U$ treatment lead to fewer transcripts with high $\theta_n$, so the threshold was lowered to increase the number of transcripts). In the case of the comparison shown in FIG. 1H, the adjustment factor determined for chemistry-induced dropout was ~5% (i.e., x=0.05 in the equation above, which leads a transcript with 75% new reads to be adjusted to 79% and a transcript with 25% new reads would be adjusted to 26% new reads).

The transcript half-lives were determined using the adjusted fraction of new RNA assuming a simple exponential model of their kinetics. The half-life values were compared to similar reports and the $r^2$ determined using the lm function in R.

Gene Ontology Analysis.

GO analysis from the PANTHER database (version 12.0) (Thomas et al., (2003) Genome Res, 13:2129-2141) was performed using a statistical over-representation test (default parameters) on the complete biological process annotation set using the top 10% slow or top 10% fast turnovers RNAs in the 1 hour MEF TimeLapse-seq data as determined by the half-life analyses described above.

Differential Expression Analysis

Differential expression analysis was performed using DESeq2. To examine the inferred differences in the new transcript pool based on TimeLapse mutations, the unadjusted estimates of the fraction of new RNA were used to infer the number of counts resulting from new transcripts as described above. As TimeLaspse-seq data are internally controlled, the size factors determined from total counts were used to scale each data set (i.e., DESeq2 was run on the total RNA-seq data and the sizeFactors function was used to scale the inferred new RNA counts to the RNA-seq-determined values) with default conditions including the Benjamini-Hochberg (Benjamini and Hochberg, (1995) J. R. Stat. Soc. B Stat. Methodol, 57:289-300) adjusted P value ($p_{adj}$ in text). RNA-seq analysis was performed on all reads (i.e., reads that had zero or more T-to-C mutations) using DESeq2 with default parameters.

Estimation of Contaminating Reads in TT-TimeLapse-seq

Reads from TT-TimeLapse-seq were processed and analyzed as for TimeLapse-seq. Junction-containing reads were determined from the presence of "N" characters in the CIGAR string in the aligned bam file using bamtools (version 2.3). The levels of contaminating reads were estimated by assuming the contaminating reads have the same ratios as RNA-seq data, and that reads with three or more mutations constitute the true ratio of reads. Reads with three or more mutations were used as true positives, because the probability of a read containing three or more mutations without $s^4U$ is $<10^{-5}$. The fraction of intron- or junction-containing reads was used for the RNA-seq data ($r_o$), the total in the true positive population ($r_{tp}$), and the total for each population ($r_x$). In each analysis, only reads that had nonzero ratios and ratios that were less than one were considered. The fraction of reads from contamination ($c_x$) was then estimated:

$$c_x = \frac{r_{tp} - r_o}{r_x - r_o}$$

For comparisons with the TT-TimeLapse-seq data presented here, the data from Schwalb et al. ((2016) Science, 352:1225-1228; SRR4000390, SRR4000391 and SRR4000397) were aligned and processed using the same pipeline described for TimeLapse-seq. For this comparison, TT-TimeLapse-seq data was reprocessed using only 75 nt of each read, and this trimming was performed on fastq files before alignment. This step was performed because the probability of a sequencing read containing a splice junction or being an intron-only read is dependent on the read length. Otherwise, all processing was handled equally between data sets.

The experimental results are now described

To track RNA dynamics directly in a sequencing experiment, TimeLapse-seq (FIG. 1A) was developed, a method in which cells are exposed to a non-canonical nucleoside that becomes incorporated only into new transcripts. Rather than enriching the metabolically labeled RNAs, this approach chemically converts the metabolic label into a base analogue that causes mutations in a sequencing experiment. This approach is akin to convertible-nucleoside chemistry (Allerson et al., 1997, J Am Chem Soc, 119:7423-7433; Harris et al., 1991, J Am Chem Soc, 113:4328-4329; MacMillan and Verdine, 1990, J Org Chem, 55:5931-5933) that was developed to post-synthetically modify oligonucleotides after they have been made by solid-phase oligonucleotide synthesis. In TimeLapse-seq, the RNA is synthesized by the cell rather than on an oligonucleotide synthesizer. The mutations introduced using this chemistry distinguish which RNAs were transcribed during the time of the experiment. TimeLapse-seq does not require biochemical enrichment of the labeled RNA; instead, it relies on a mutational mapping strategy to monitor RNA dynamics.

Figure 1B:
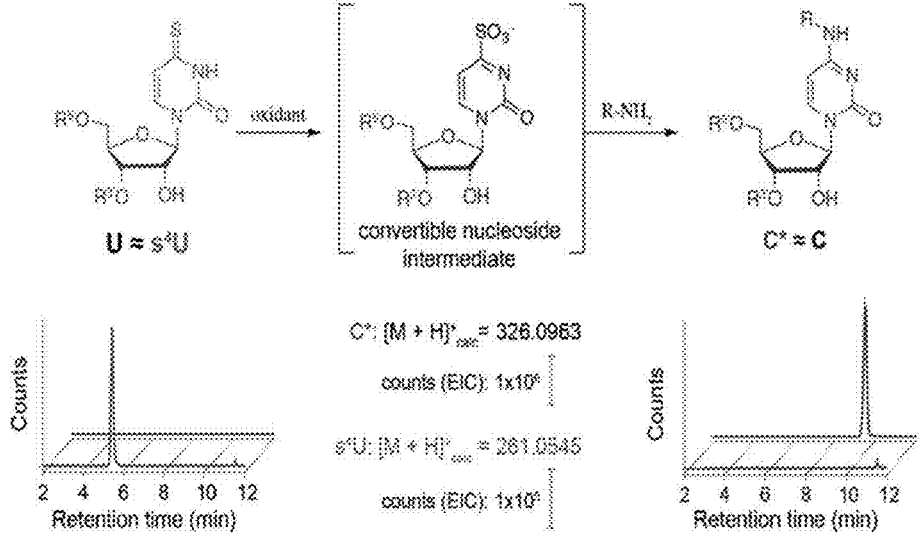
Figure 1C:
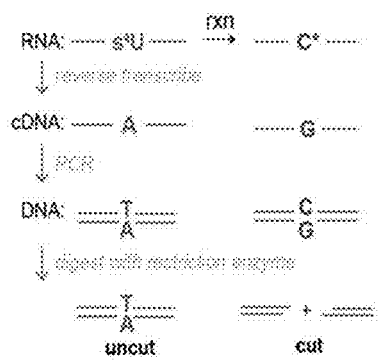

For the development of TimeLapse-seq, $s^4U$ was focused on based on its demonstrated utility in RNA metabolic labeling experiments (Rabani et al., 2011, Nat Biotechnol, 29:436-442; Duffy et al., 2015, Mol Cell, 59:858-866) and the orthogonal reactivity of its thione relative to other functional groups found in RNA. The $s^4U$ base itself leads to low levels of U-to-C transitions upon reverse transcription (Hafner et al., 2010, Cell, 141:129-141), but does so at levels too low to robustly identify new transcripts. While recent applications of $s^4U$ have mostly focused on the thione as a nucleophile, or exploited the photochemistry of this nucleoside to induce UV crosslinks (Mishima and Steitz, 1995, Embo J, 14:2679-2687; Moore and Sharp, 1992, Science, 256:992-997), the focus of this study is on transforming $s^4U$ into other bases using oxidative-nucleophilic-aromatic substitution (Yano and Hayatsu, 1970, Biochim Biophys Acta, 199:303-315; Saladino et al., 1996, Tetrahedron, 52:6759-6780). Without being bound to a particular theory, it was reasoned that oxidation of $s^4U$ would effectively transform it into a convertible nucleoside, providing an activated intermediate that could be transformed into an analogue of cytosine by aminolysis (FIG. 1B). The $s^4U$ base retains uridine's Watson-Crick hydrogen-bonding pattern, and while other chemical conditions used to modify $s^4U$ (e.g., alkylation) change the base's hydrogen bonding pattern, they do not recode the base to match C's native hydrogen-bonding pattern. While not widely explored, the oxidative reactivity of $s^4U$ has precedent in UV-cross-linking studies, where sites of $s^4U$-protein crosslinks are enriched for T-to-C mutations, or in mapping the locations of $s^4U$ bases in Escherichia coli tRNA (Rabani et al., 2014, Cell, 159:1698-1710; Ziff and Fresco, 1969, Biochemistry, 8:3242-3248). If conducted before an RNA-seq analysis, this reaction could be used to reveal sites of $s^4U$ incorporation as identified by T-to-C mutations stably introduced in the cDNA. Conditions that efficiently convert $s^4U$ to cytosine analogues while remaining RNA-friendly are identified herein.

Figures 1F, 1G, 1H, 1I:
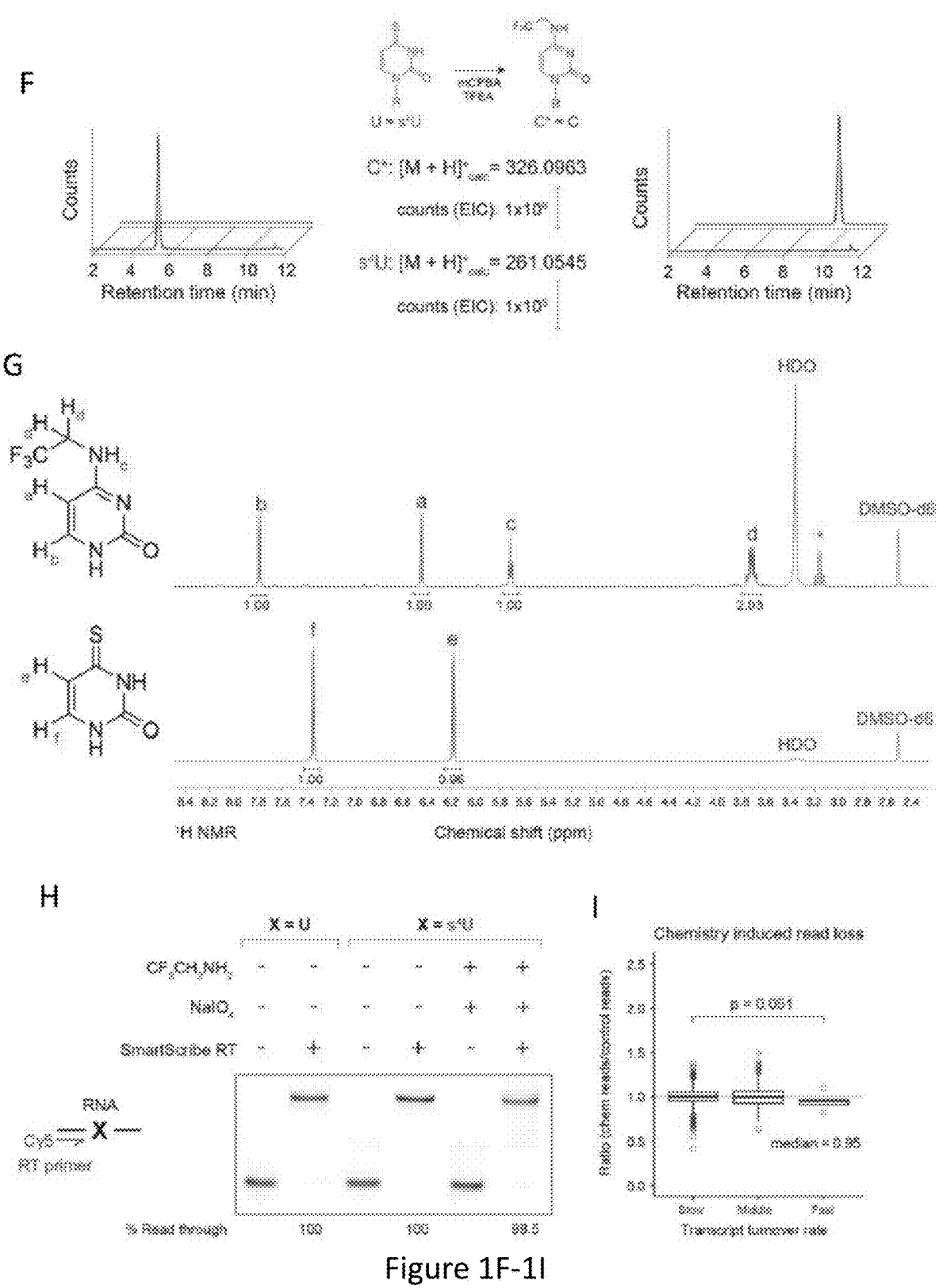
Figure 3A:
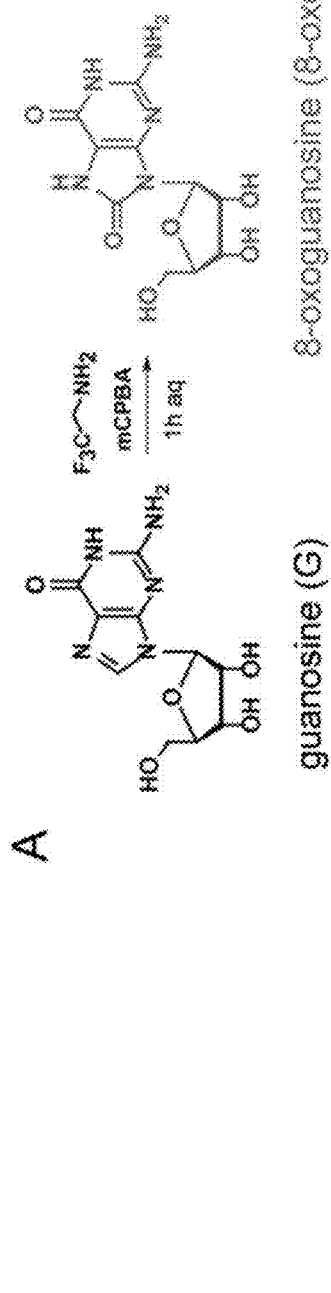
FIG. 3A through FIG. 3F, depicts the results of example experiments demonstrating that oxidative nucleophilic aromatic substitution can be effective with minimal oxidation of guanosine to 8-oxoG.
Figure 3B:
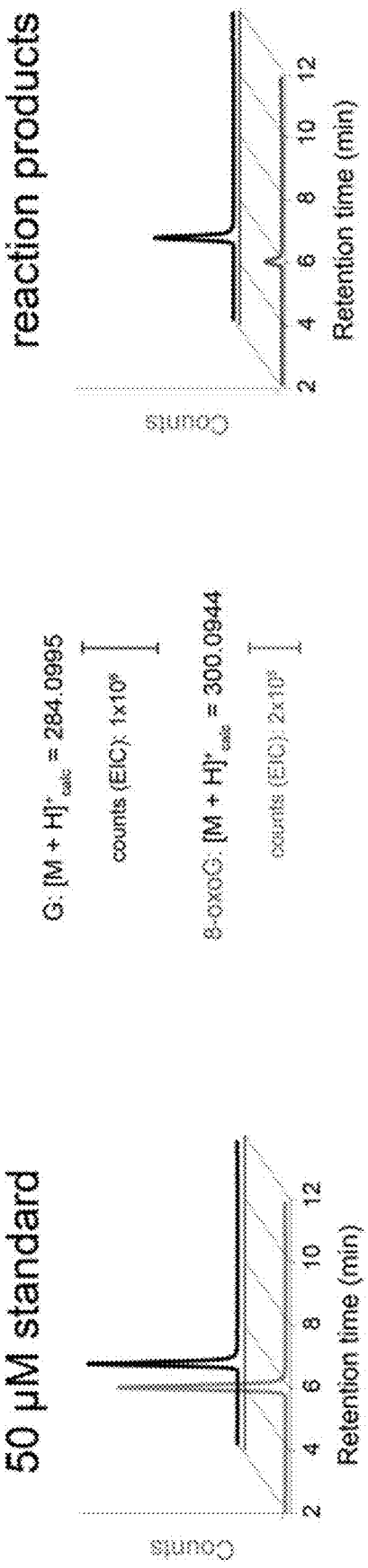

Chemistry to convert the free nucleoside (s⁴U) to cytosine derivatives was explored using an LC-MS assay to test a range of oxidants and amines (FIG. 1B and FIG. 2) was explored. Oxidants were chosen that would efficiently activate s⁴U, but not lead to oxidation of guanosine to 8-oxoguanosine (FIG. 3A). Amines and related nucleophiles with low pKa values were used so that they would remain largely deprotonated under the reaction conditions, ensuring an RNA-friendly environment. From this screen, it was found that treating s⁴U with 2,2,2-trifluoroethylamine (TFEA) and meta-chloroperoxybenzoic acid (mCPBA) results in near-complete consumption of s⁴U, producing only small amounts of the hydrolysis product uridine, and mostly converting s⁴U to the desired trifluoroethylated cytidine (C*, FIG. 1B; FIG. 1F).

Figures 4A, 4B, 4C, 4D:
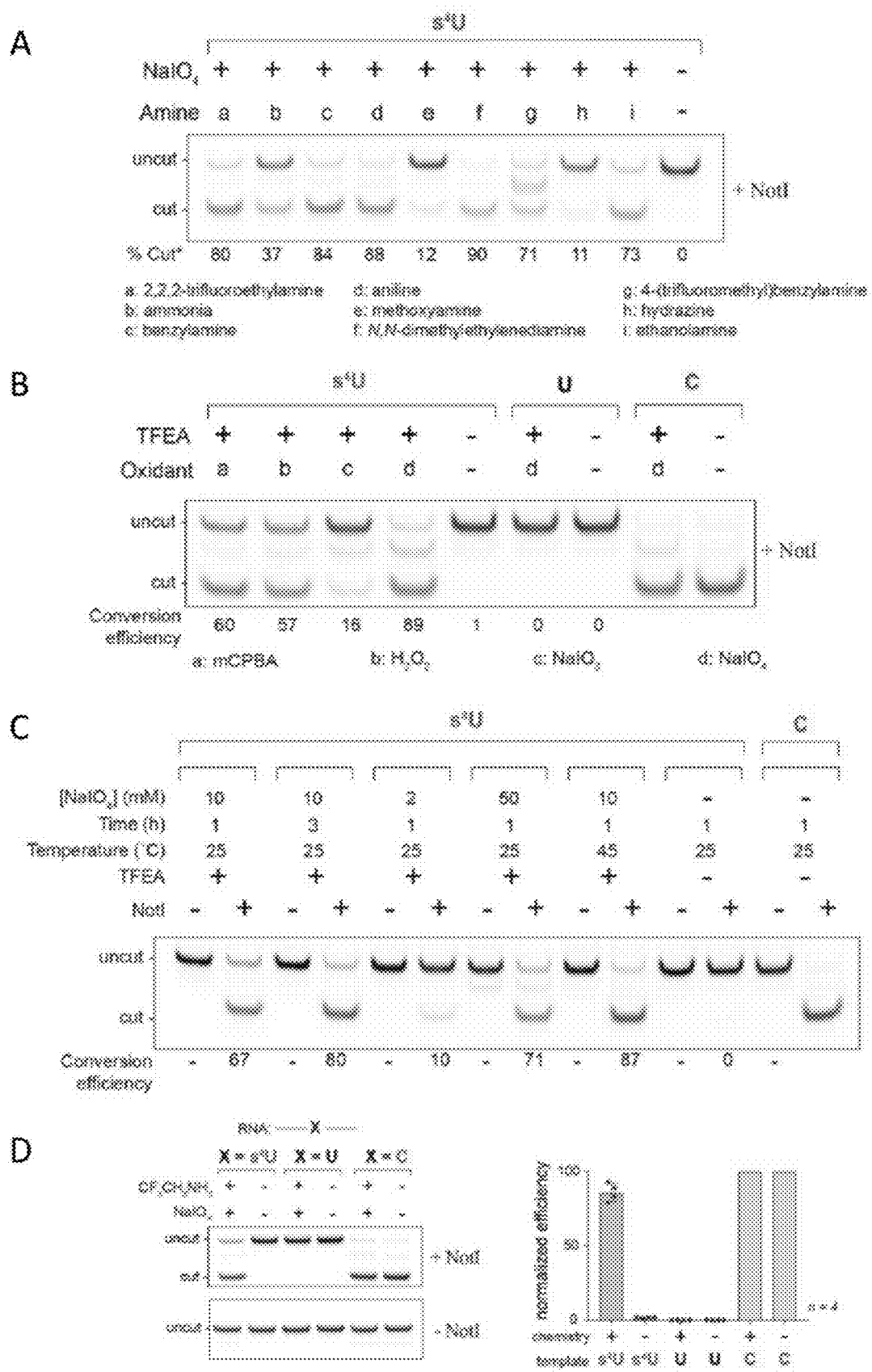
FIG. 4A through FIG. 4D, depicts the results of example experiments from a series of NotI restriction digestion assays used in the optimization of TimeLapse-seq chemistry.

These reaction conditions were found to convert s⁴U to C analogues in the context of an oligoribonucleotide. This was accomplished using an RNA substrate containing a single s⁴U (introduced by in vitro transcription of a template with one adenosine and s⁴UTP) and a mutation-dependent restriction digestion assay to reveal T-to-C mutations after chemical treatment and reverse transcription (FIG. 1C; FIG. 4A-FIG. 4C). Using this assay, the nucleophile, oxidant, temperature, and time were all optimized. When s⁴U RNA was treated with TFEA and sodium periodate at 45° C. (FIG. 1D, FIG. 1G and FIG. 2), reverse transcriptase could efficiently transcribe the product, and the majority of the resulting DNA (~80%) had the desired T-to-C mutation (FIG. 1E, FIG. 1H, FIG. 1I and FIG. 4D).

NaIO₄ is an oxidant commonly used in RNA biology to oxidize the 3'-end vicinal diol of RNAs with minimal effects on other functional groups, even through multiple rounds of oxidation (Dai et al., (2017) Nat. Methods, 14:695-698). To test NaIO₄ and TFEA with cellular s⁴U-RNA, mouse and human cells were exposed to a range of concentrations of s⁴U. After RNA isolation and chemical treatment, the apparent U-to-C conversion rates were examined (inferred from T-to-C mutations in the cDNA, hereafter referred to as T-to-C) by targeted RT-PCR coupled to paired-end sequencing. A notable and specific increase in T-to-C transitions was observed in chemically treated samples FIG. 5.

Figures 5A, 5B, 5C, 5D, 5E:
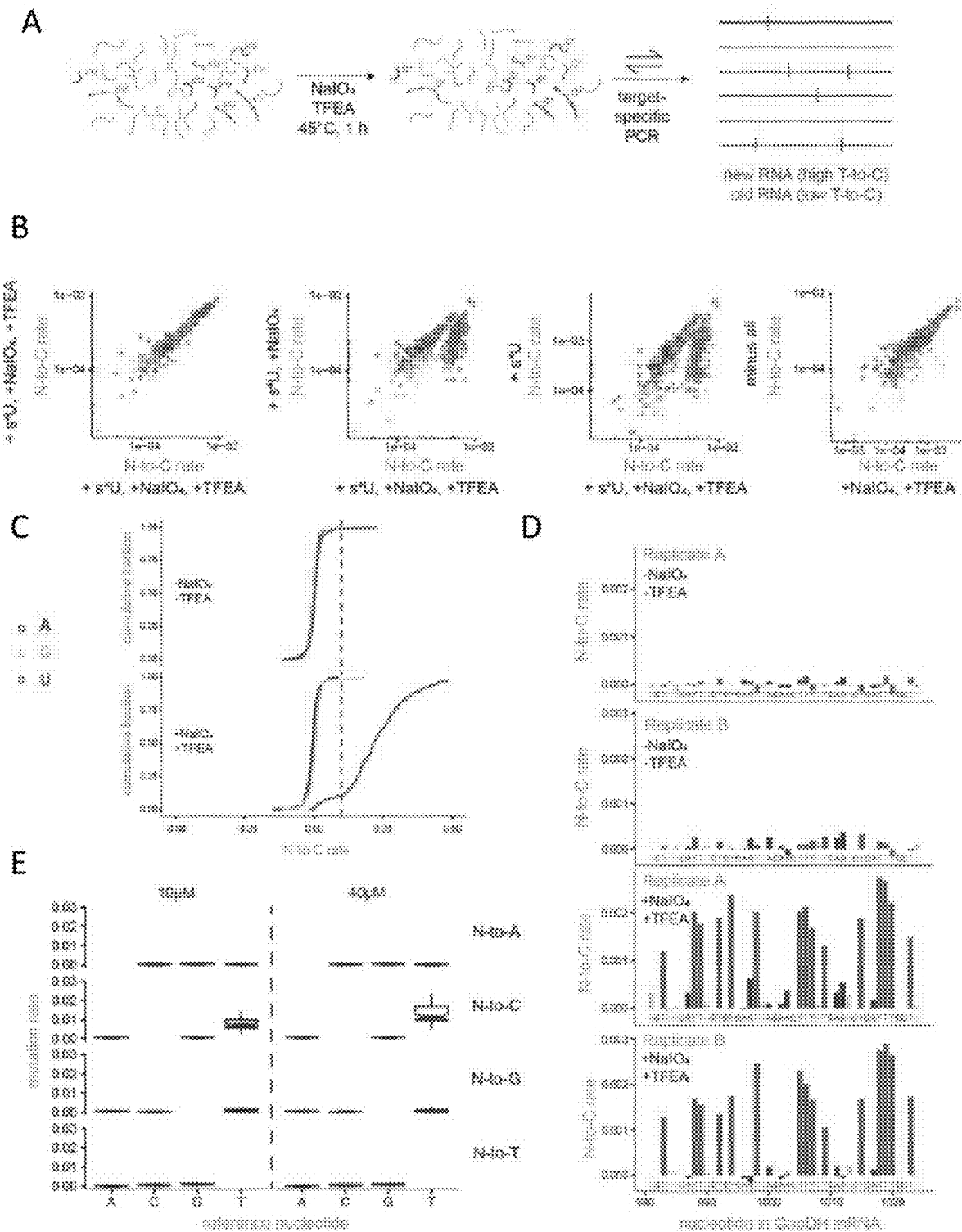
FIG. 5A through FIG. 5E, depicts the results of example experiments demonstrating that targeted TimeLapse-seq reveals enrichment of T-to-C mutations in chemically treated RNA isolated from metabolically labeled cells.
Figure 6:
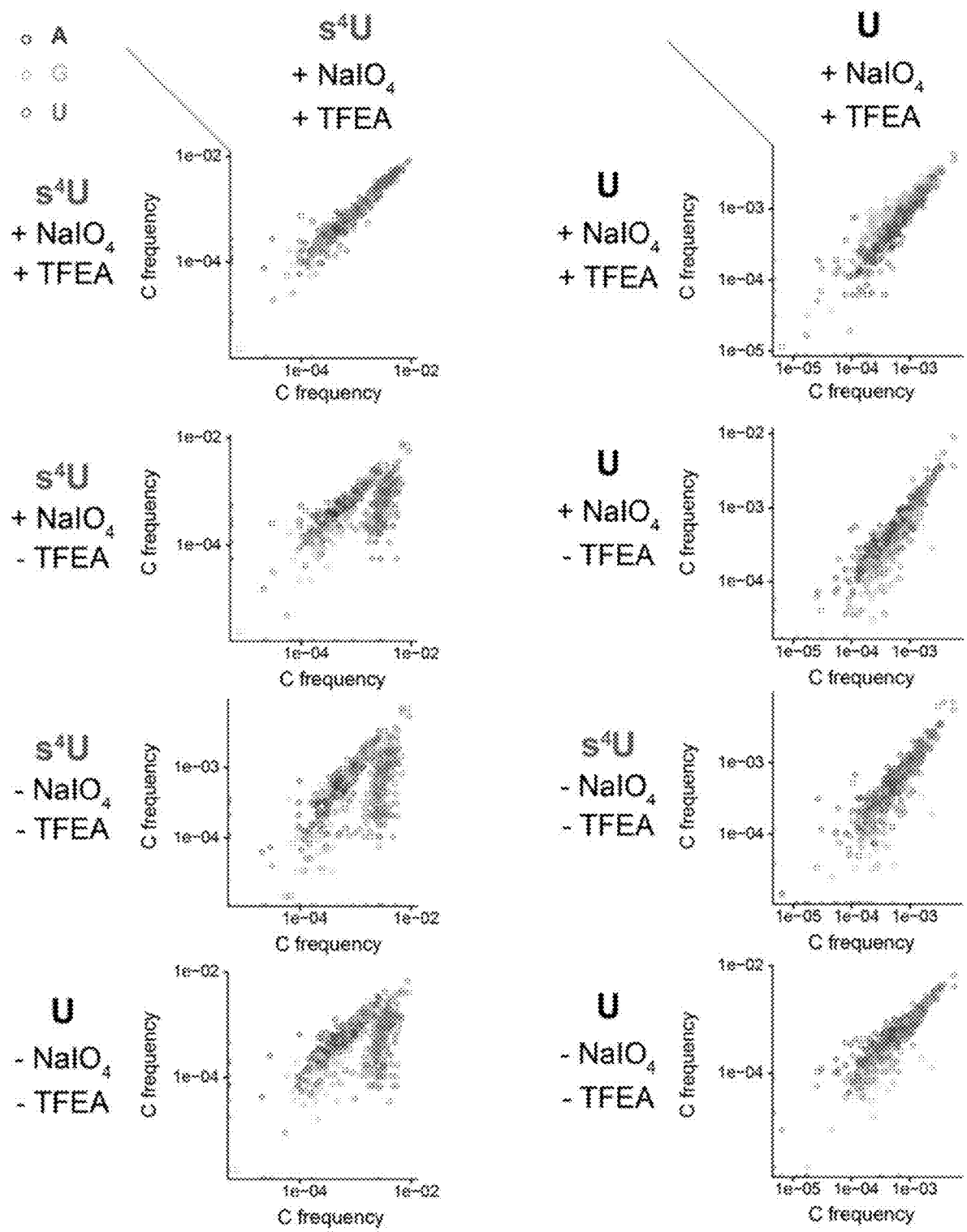
FIG. 6 depicts example correlation plots of raw N-to-C mutation frequencies in targeted TimeLapse-seq using either $s^4U$ treated (left) or untreated (right) samples.
Figure 7:
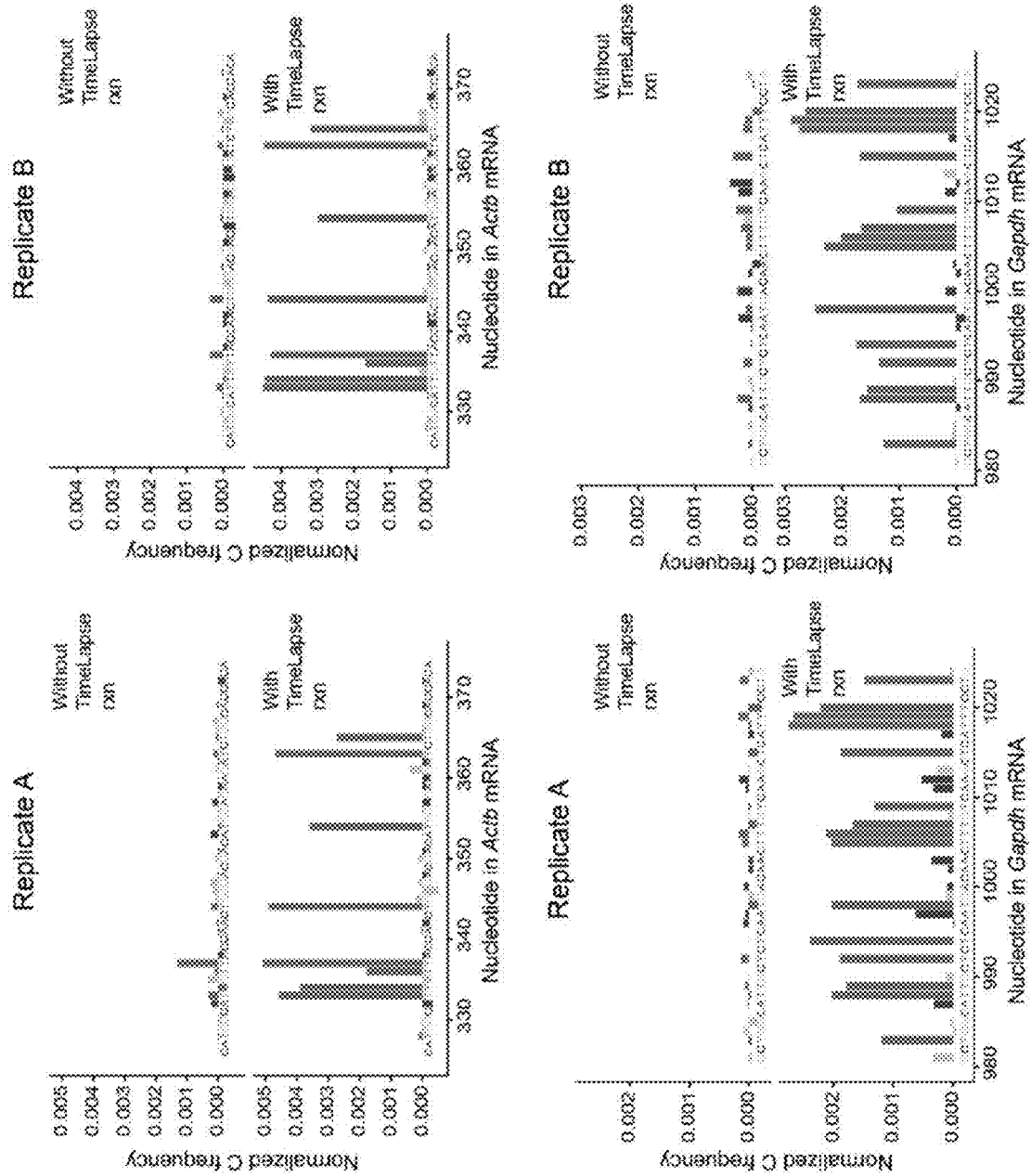
FIG. 7 depicts example replicate barplots of normalized N-to-C mutation frequencies for selected regions of Actb and Gapdh mRNAs from $s^4U$ treated cells with and without TimeLapse chemistry treatment. Annotated U nucleotides generally display higher T-to-C mutation frequencies in a TimeLapse chemistry-dependent treatment. Biological replicates display a high degree of similarity in T-to-C mutation frequencies.
Figure 8:
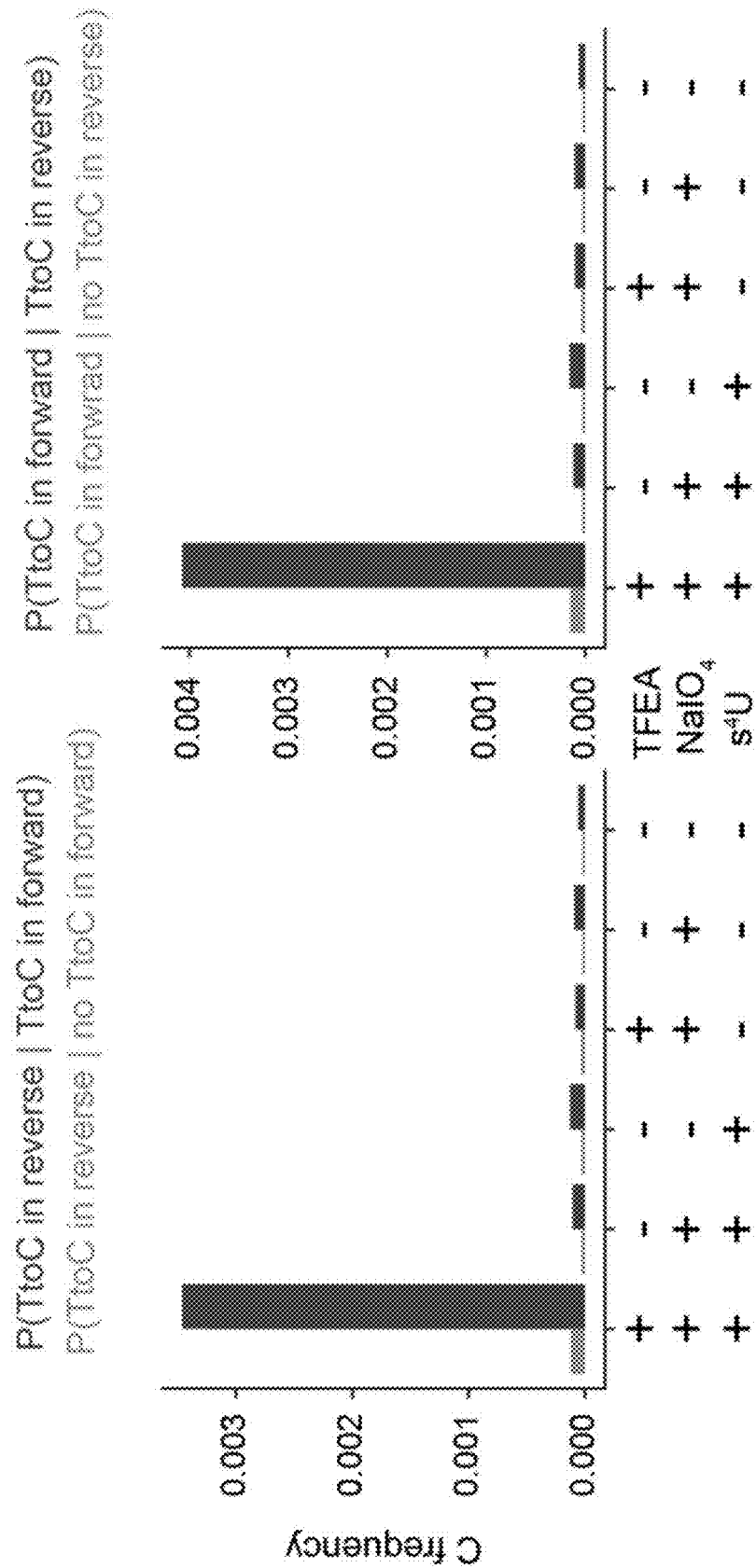
FIG. 8 depicts an example barplot analysis demonstrating the non-random dependence of T-to-C mutation content in mate-pairs. A random distribution of T-to-C mutations would result in the pairs of bars being the same height. While low levels of low quality reads lead to a slight correlated increase in T-to-C mutations in negative controls, only $s^4U$ treatment and TimeLapse chemistry leads to a large increase in T-to-C mutations.

To test whether this chemistry could reveal newly transcribed RNAs for TimeLapse-seq, MEF cells were exposed to s⁴U for two hours, and the total RNA was isolated (s⁴U2A). A dramatic increase in T-to-C transitions in samples that were chemically treated (FIG. 5) was observed, but a similar increase was not observed for A-to-C and G-to-C transversions (FIG. 5 and FIG. 6). The relative increase in rates of mutations compared to untreated samples were determined, and it was found that the majority of U positions (88%) exceeded a threshold of 0.1% increase in mutations (FIG. 5). Few U positions (<2%) in samples that lacked s⁴U treatment, oxidant or amine exceeded this same threshold (FIG. 5, FIG. 7). Further, sequencing reads were dramatically more likely to have mutations if the mate-pair from the same read had a T-to-C mutation (FIG. 8). Thus, the T-to-C mutations in this targeted TimeLapse-seq are not randomly distributed, but rather are specifically induced in a subpopulation of s⁴U metabolically labeled RNAs when they are subjected to TimeLapse-seq chemistry. These results demonstrate that TimeLapse chemistry is specific for inducing T-to-C mutations at sites of s⁴U, and can be used in RNA-sequencing experiments.

Figure 3C:
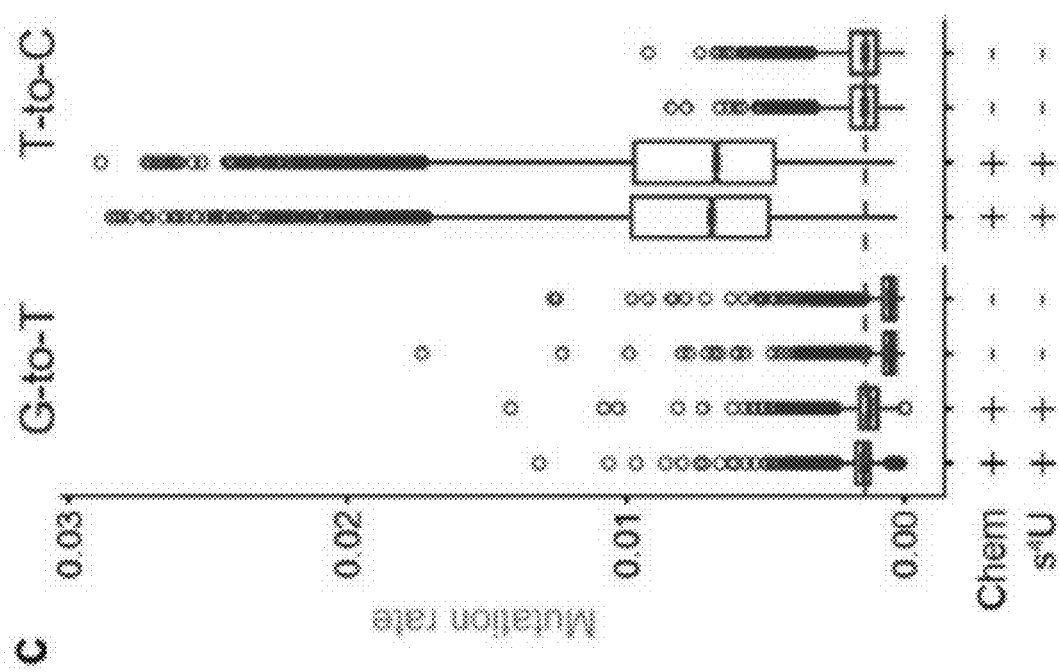
Figure 3D:
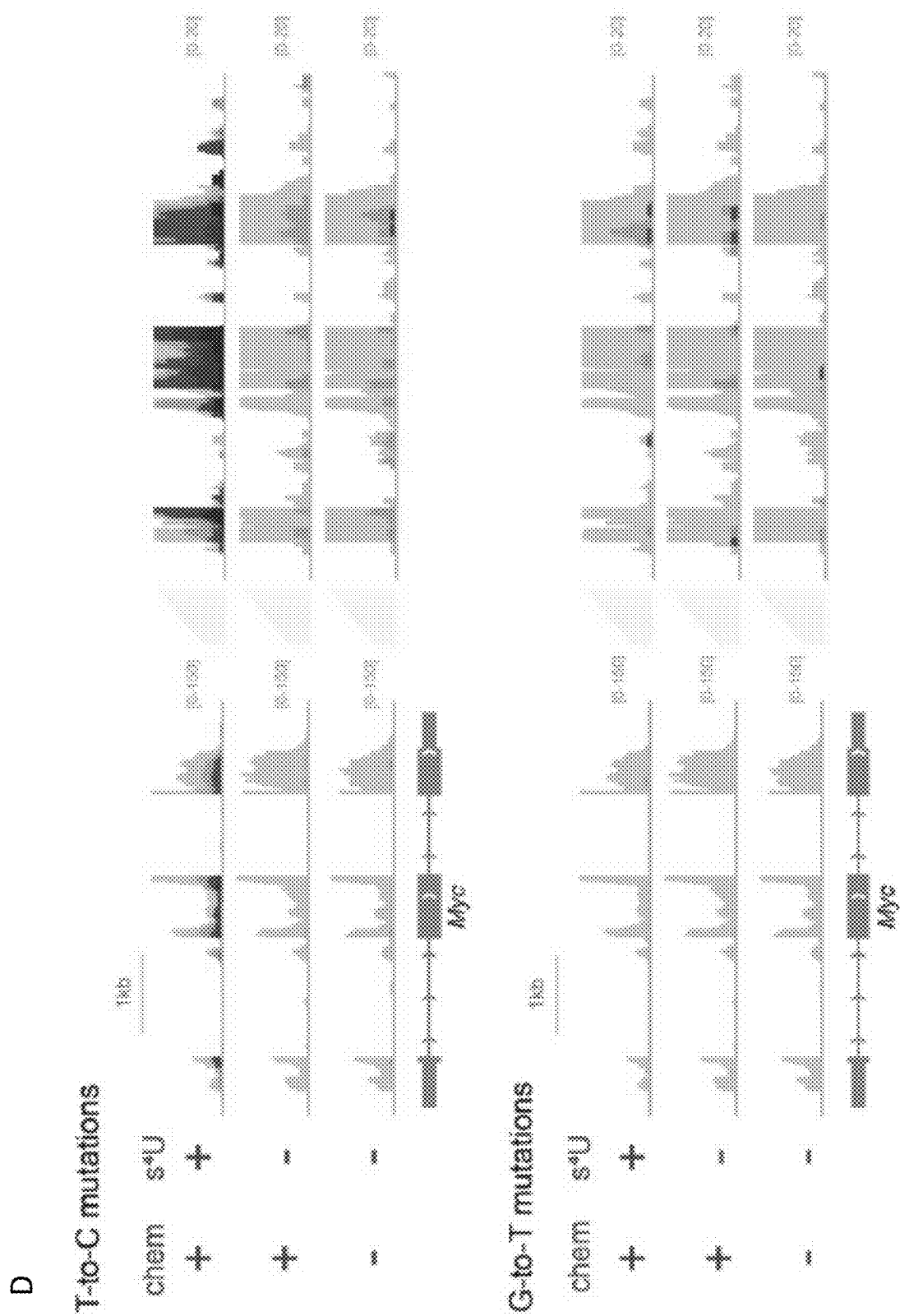
Figures 3E, 3F:
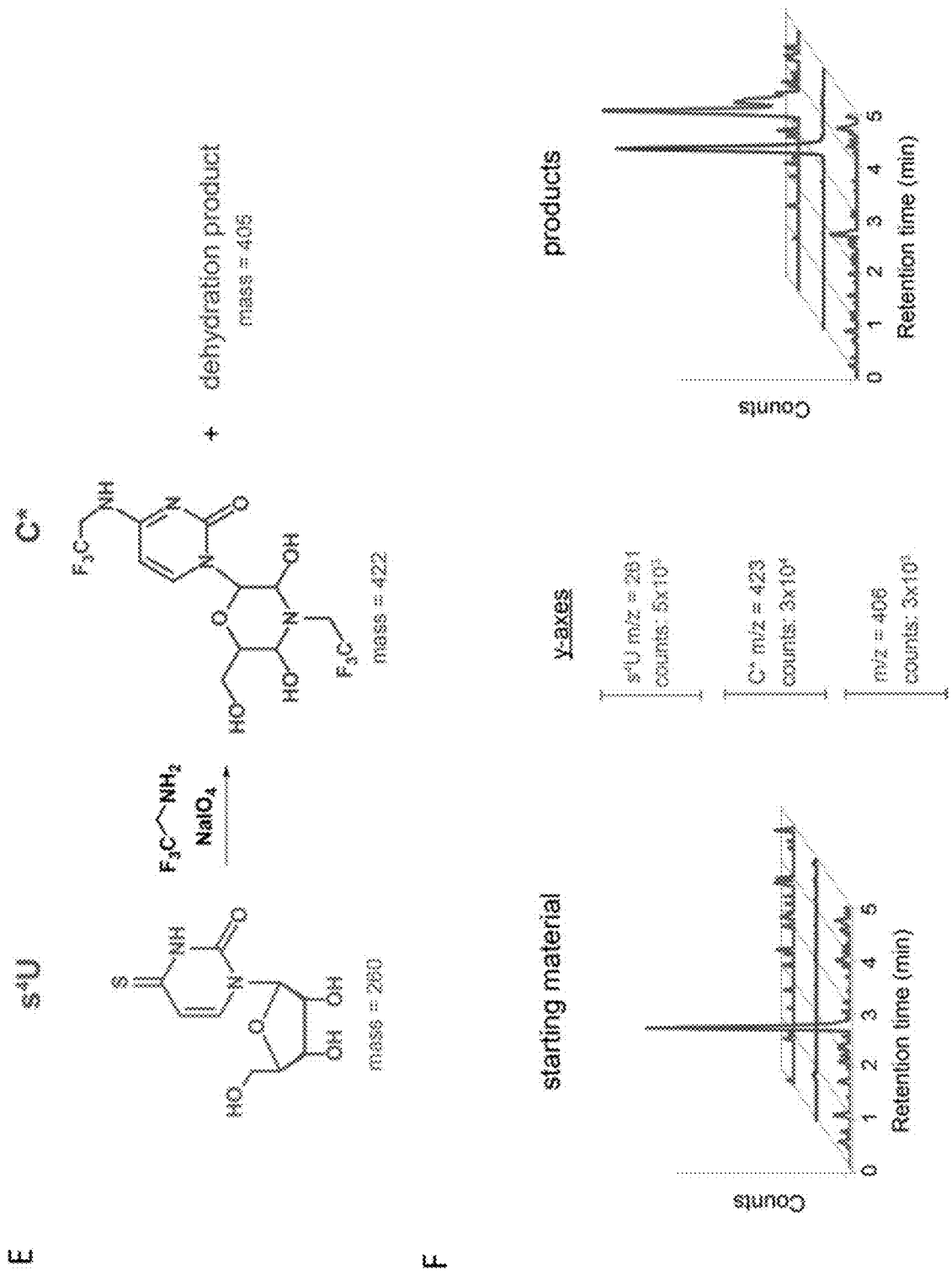
Figures 9A, 9B, 9C, 9D:
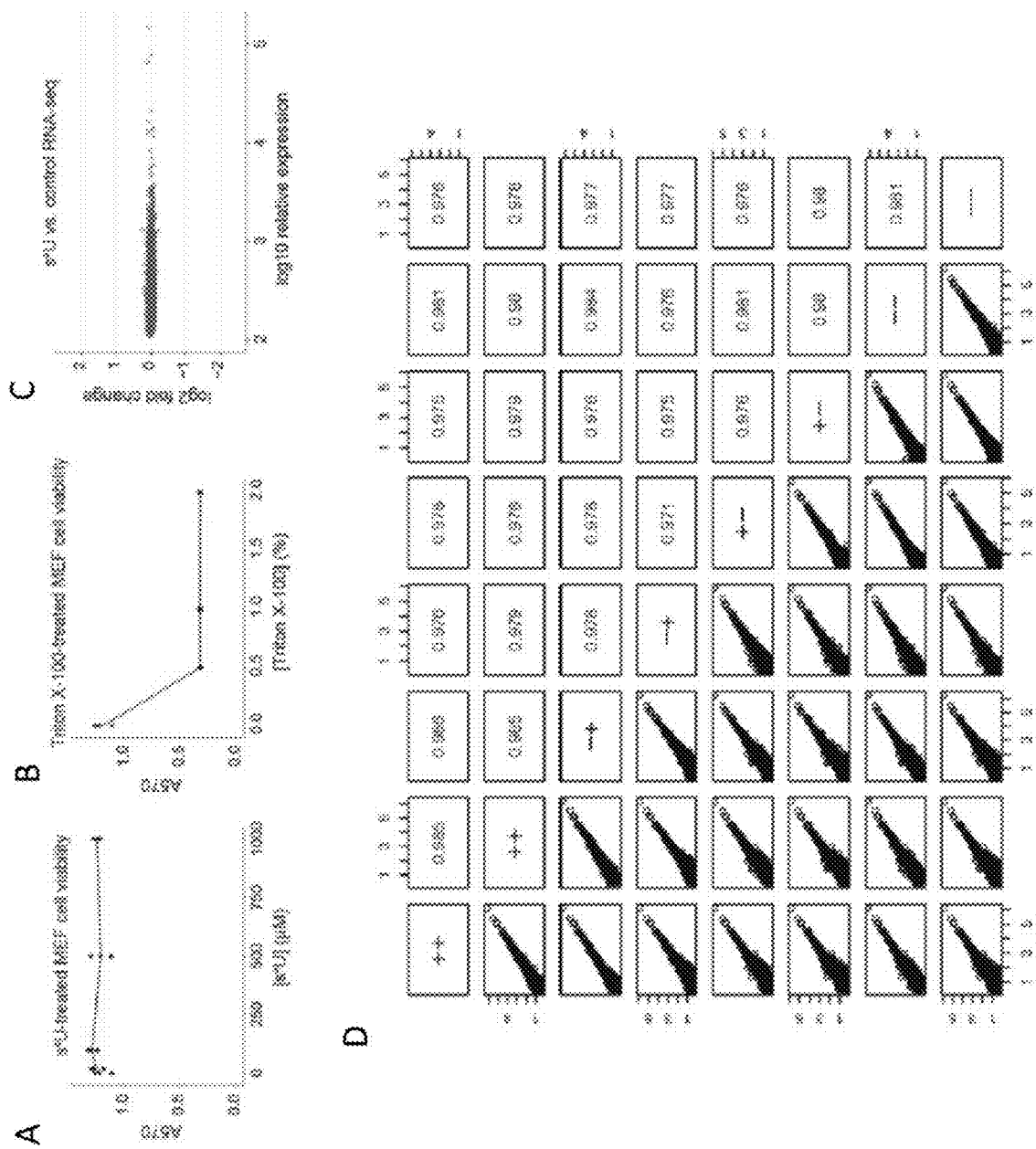
FIG. 9A through FIG. 9D, depicts the results of example experiments demonstrating TimeLapse and $s^4U$ treatment do not significantly perturb cells or cellular RNAs. $s^4U$ and TimeLapse treatment do not significantly perturb cells or cellular RNAs.
Figure 10:
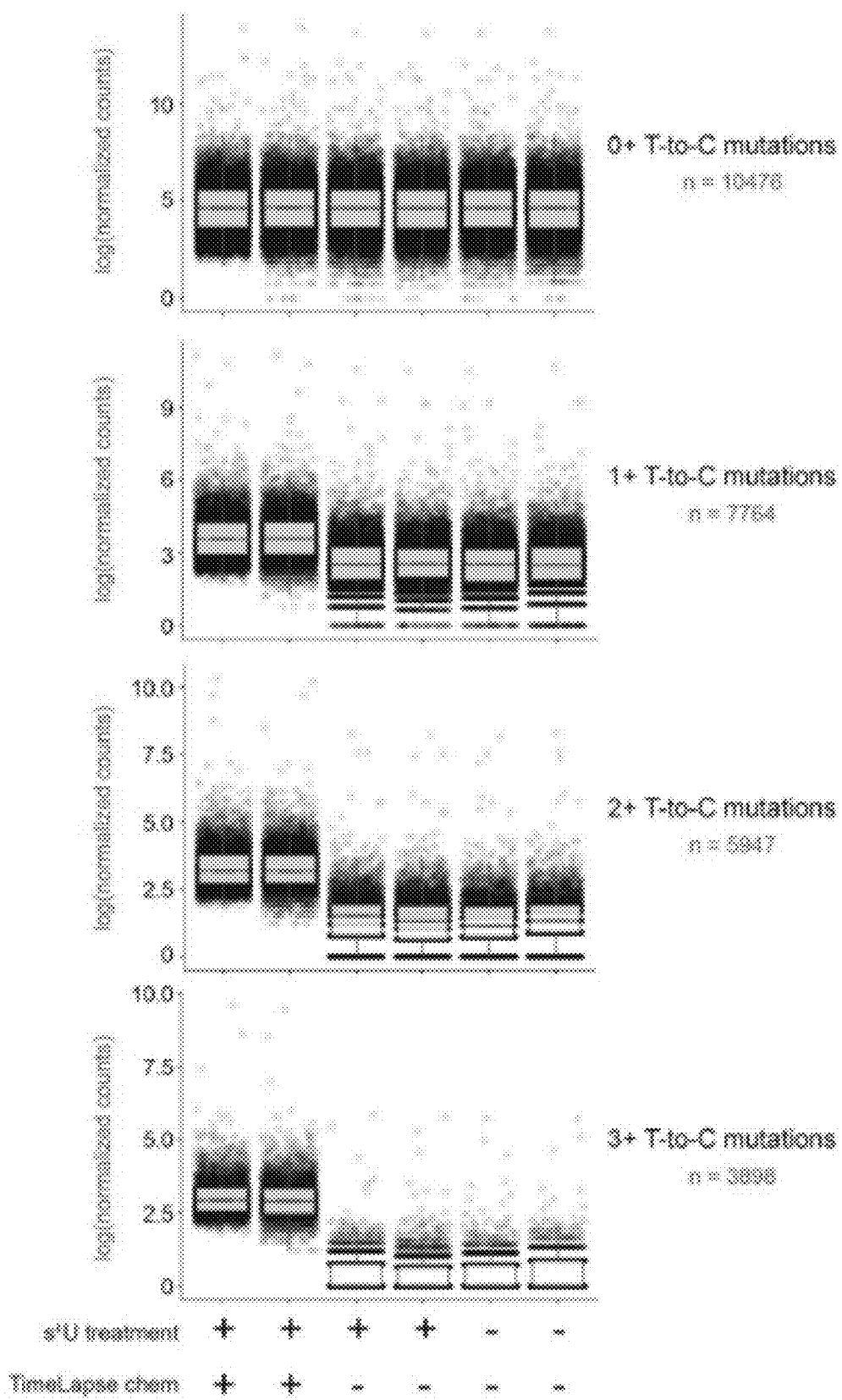
FIG. 10 depicts the results of example experiments demonstrating TimeLapse-seq reads display an enrichment of T-to-C mutations in the transcriptome. Analysis of the distribution of reads in each sample including either all reads (top) or reads with increasing numbers of T-to-C mutations. Read counts were normalized to the total RNA-seq analysis (top) and log transformed after adding a pseudocount of one to each transcript. Data for individual transcripts are overlaid with box and whiskers plots using default parameters from ggplot2. Transcripts were only included if at least two samples had more than 20 counts. The number of transcripts in each analysis are indicated next to each graph.
Figures 12A, 12B:
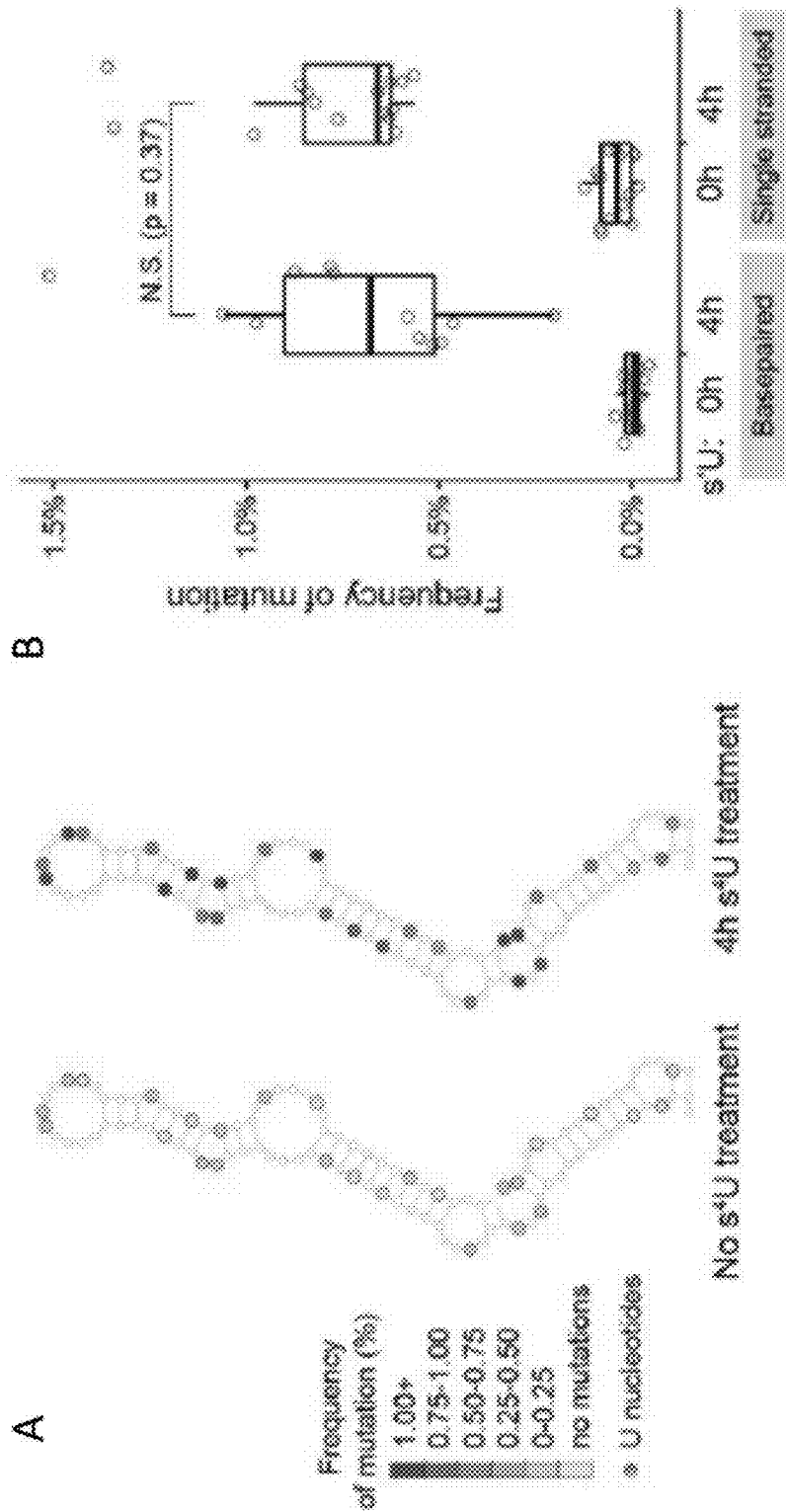
FIG. 12A through FIG. 12B, depicts the results of example experiments demonstrating TimeLapse-seq mutation rates in structured regions of the 7SK RNA transcript. TimeLapse-seq mutation rates in structured regions of the 7SK RNA transcript. U-to-C mutation rates were calculated as described in Methods.
Figure 14:
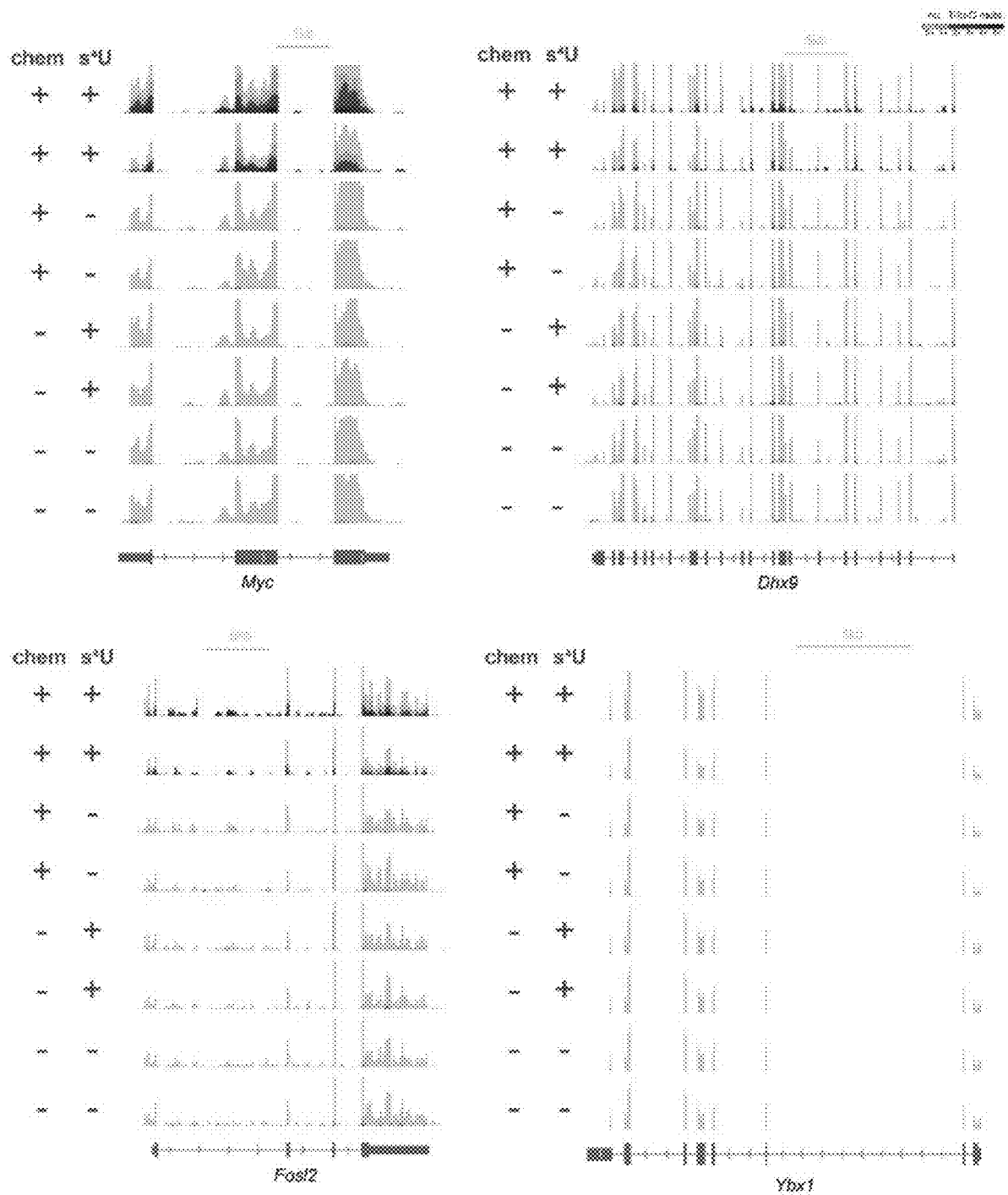
FIG. 14 depicts exemplary browser shots of TimeLapse-seq coverage of transcripts with different rates of turnover. Browser shots of TimeLapse-seq coverage of the transcripts Myc, Dhx9, Fos12, and Ybx1. Replicates with or without $s^4U$ and TimeLapse chemistry are shown.
Figures 15A, 15B, 15C, 15D, 15E, 15F:
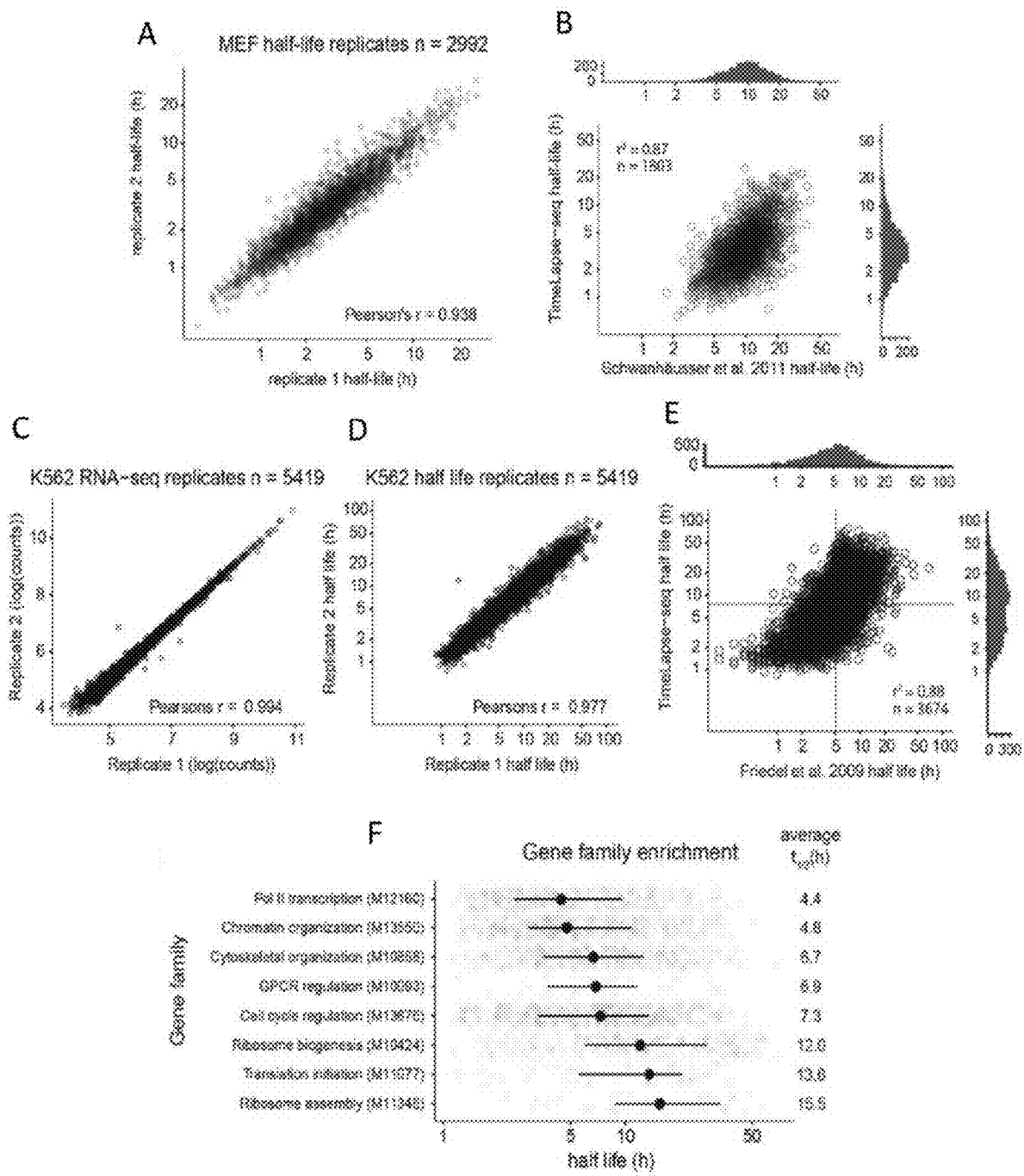
FIG. 15A through FIG. 15F, depicts the results of example experiments demonstrating correlations of TimeLapse-seq and estimated half-lives for transcriptome wide MEF and K562 data.
Figures 16A, 16B, 16C, 16D, 16E, 16F:
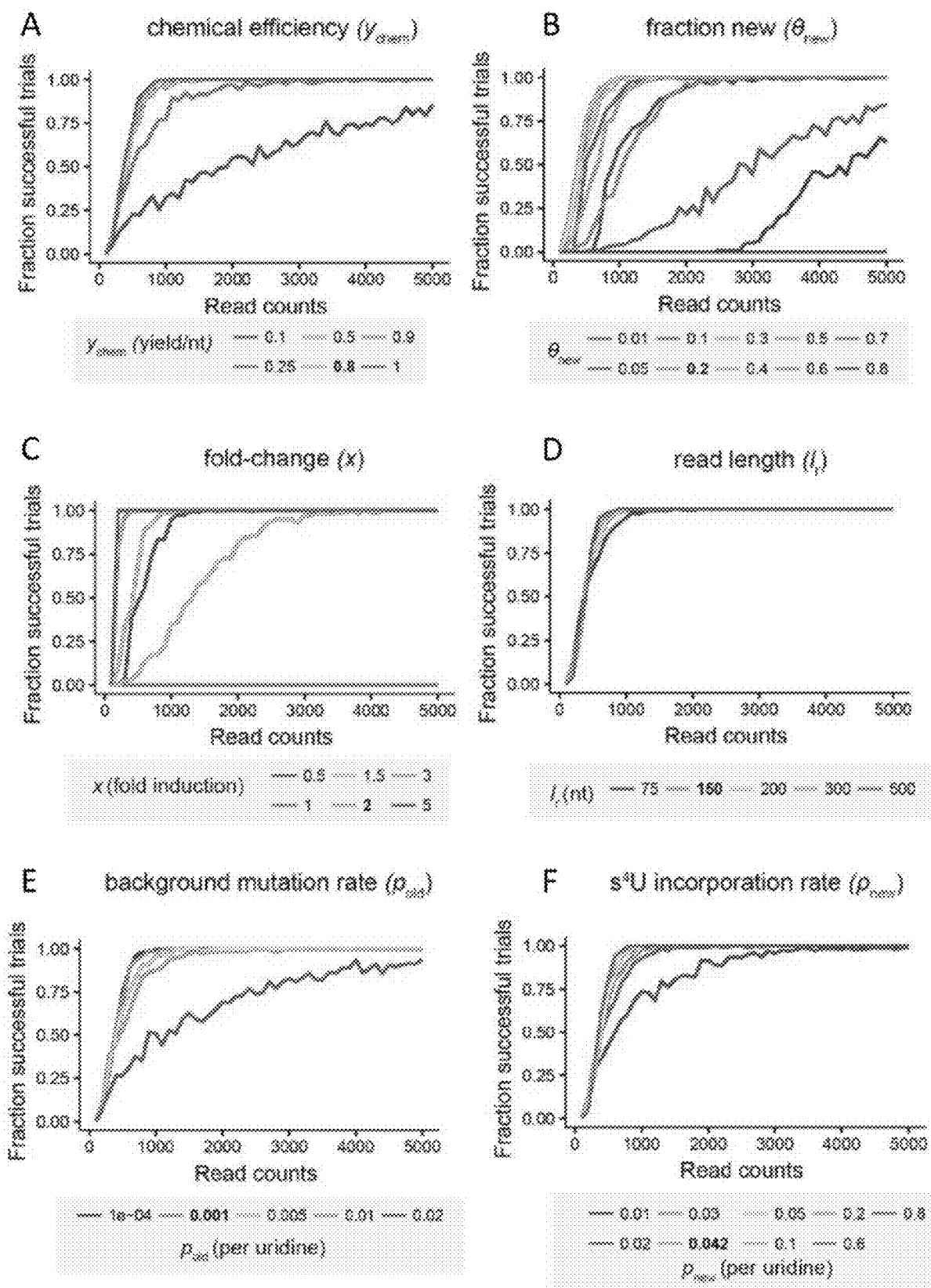
FIG. 16A through FIG. 16F, depicts exemplary experimental results of simulations exploring necessary read depth required to confidently identify changes in new transcripts by TimeLapse-seq. Plots displaying the results from simulations exploring the necessary read depth required to confidently identify changes in new transcripts by TimeLapse-seq. Each graph displays the probability of successfully detecting changes in the new read pool as a function of read depth from simulated TimeLapse-seq data. The following parameters relevant to TimeLapse-seq were systematically varied or held constant at the indicated value (bolded values)

To examine the dynamics of cellular RNAs, MEF cells were treated with s⁴U for 1 hour (where no s⁴U toxicity was observed; FIG. 9A-FIG. 9C) and performed TimeLapse chemistry before sequencing. The total transcript counts from each sample were highly correlated irrespective of s⁴U exposure or chemical treatment (Pearson's r≥0.97, FIG. 9D), demonstrating that TimeLapse-seq retains information from a traditional RNA-seq experiment. By counting the mutations in each aligned read pair, a specific and reproducible increase in T-to-C mutations was found, dependent on both metabolic labeling with s⁴U and chemical treatment (FIG. 10 and FIG. 11). Other mutation rates remained below background levels of T-to- C mutations in untreated samples (e.g., the small increase in G-to-T mutations, FIG. 3C). Additionally, the reaction was efficient even in regions of RNA secondary structure (FIG. 12). The T-to-C mutation counts were dramatically higher in fast-turnover transcripts (e.g., Myc and Fos12), compared to more stable transcripts (e.g., Dhx9 and Ybx1) (FIG. 13A, FIG. 13B and FIG. 14). An enrichment of T-to-C mutations was observed in intronic reads (FIG. 13C) consistent with the fast turnover of intronic RNA. To quantify these results, reads were modeled as arising from two populations: pre-existing RNAs (background mutation rate) and new RNAs (high T-to-C mutation rate; FIG. 13B). Reads from newly synthesized RNAs had an average of 2.2 mutations per read, corresponding to an ~3% mutation rate per uridine (compared to ~0.1% T-to-C mutation rates in controls and for pre-existing RNAs). From each gene, the fraction of newly made transcripts was determined (r≥0.94; 2,992 genes) and transcript half-lives were estimated, which correlated with those reported previously (Schwanhausser et al., (2011) Nature 473, 337-342) (FIG. 15). As expected, the fast-turnover RNAs (top 10%, n=360) were enriched for transcripts such as transcription factors (DNA-templated transcription, P<10-20), while the slow-turnover RNAs (top 10%, n=361) were enriched for those that are involved in translation (ribosomal biogenesis, P<10-6; translation, P<10⁻²⁷). Estimates of the fraction of newly synthesized RNA were particularly robust when the new transcripts represented ~200 reads in the experiment (FIG. 16).

Distinguishing Transient Transcripts from Contaminating Reads

Figures 17A, 17B, 17C, 17D, 17E, 17F, 17G, 17H, 17I:
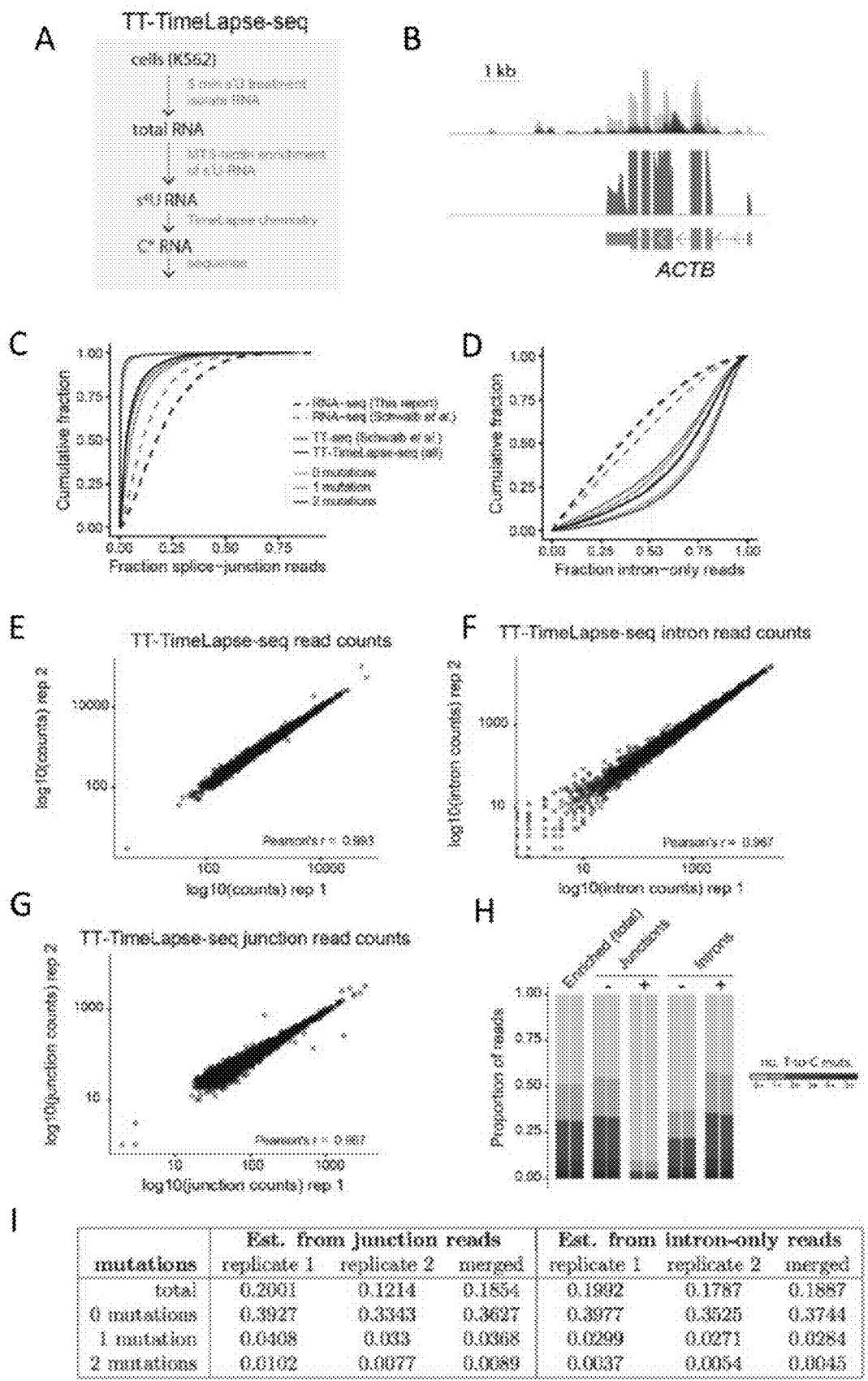
FIG. 17A through FIG. 17I, depicts exemplary experimental results demonstrating that TimeLapse chemistry can be extended for use with TT-seq to identify bona fide new rare transcripts.

Very transient RNA species, such as reads beyond the poly-A termination signal in a gene body, provide insight into transcriptome dynamics but are generally too rare to be observed at high levels by RNA-seq. While these dynamics can be studied through biochemical enrichment of very recently made RNAs after short (5 min) s⁴U treatments through transient transcriptome sequencing (TT-seq; Schwalb et al., (2016) Science, 352:1225-1228), biochemically enriched s⁴U-RNA always contains contaminating reads from unlabeled RNAs (estimated to be up to 30% in some experiments; Hafner et al., (2010) Cell, 141:129-141). This contaminating background can limit analyses; for example, abundant spliced transcripts observed in RNA enriched after short s⁴U pulses have been interpreted as fast splicing (Mukherjee et al., (2017) Nat. Struct. Mol. Biol. 24:86-96), but these results could also be explained by contaminating background (e.g., from fully spliced mature RNAs). To test if TimeLapse chemistry could be used in conjunction with TT-seq to distinguish bona fide new RNAs from contaminating background, K562 cells were labeled for 5 minutes with s⁴U, and biochemical enrichment was performed as in TT-seq (Schwalb et al., (2016) Science, 352:1225-1228), except with more efficient MTS chemistry to biotinylate the s⁴U-RNA (Duffy et al., (2015) Mol. Cell, 59:858-866; FIG. 17A). After enrichment and before sequencing, TimeLapse chemistry was performed. As expected, transient RNA species were enriched for introns (two-sample Kolmogorove-Smirnov test, P<10-15; FIG.

13D-FIG. 13F and FIG. 17) but depleted for splice junctions (P<10-15). Both enrichment of introns and depletion of splice junctions were slightly greater than previously observed? (FIG. 17C-FIG. 17D), which was likely due to the efficiency of MTS chemistry. Even with only 5 min of s$^4$U treatment, the majority of the biochemically enriched reads contained TimeLapse-induced mutations (FIG. 13D). Mutation-containing reads represented a subpopulation that was further enriched for introns and depleted for splice junctions (FIG. 13E-FIG. 13F and FIG. 17C-FIG. 17D). This suggests that mutated reads effectively capture the profile of new RNAs, while the reads without mutations represent a subpopulation that is contaminated by unlabeled reads. It was estimated that 15-20% of total TT-seq reads arise from contaminating RNA (estimate from splice-junction content, 17-20%; from intronic content, 18-20%), similar to estimates from previous s$^4$U experiments (Hafner et al., (2010) Cell, 141:129-141). Reads without mutations were enriched for contaminating reads (estimate from splice junctions, 33-39%; estimate from introns, 35-40%), while reads containing mutations are depleted in contamination. For reads with a single mutation, contaminating reads make up <5% of the signal; for reads with two mutations, the contamination is <1%. Taken together, RNA contamination contributes to the signal at the level of RNA-seq, but TimeLapse-chemistry-induced mutations can be used to discriminate between signal from new RNAs and contaminating reads. These results demonstrate transcripts including ACTB (FIG. 17B) are not highly spliced on this timescale (5 minutes) and highlight how TimeLapse chemistry can provide an extra specificity filter when analyzing rare, transient RNAs.

Identifying Acute Transcriptional Changes with TimeLapse-seq

TimeLapse-seq was next used to study global RNA dynamics upon heat shock. The TimeLapse was started by adding s$^4$U and tracking the dynamics in cells with and without relatively mild heat shock (42° C.), where only modest changes in total RNA levels are apparent (Trinklein et al., 2004, Mol Biol Cell, 15:1254-1261; Mahat et al., 2016, Mol Cell, 62:63-78). After allowing the RNA populations to evolve for 1 hour under these two conditions, total RNA was isolated from the cells. Then TimeLapse-seq was performed by treating the RNA with TFEA and sodium periodate prior to reverse transcription and paired-end sequencing. After sequencing, the reads were aligned to the genome, filtered for high quality alignments, and the number of T-to-C mutations in each read were counted.

Figure 18:
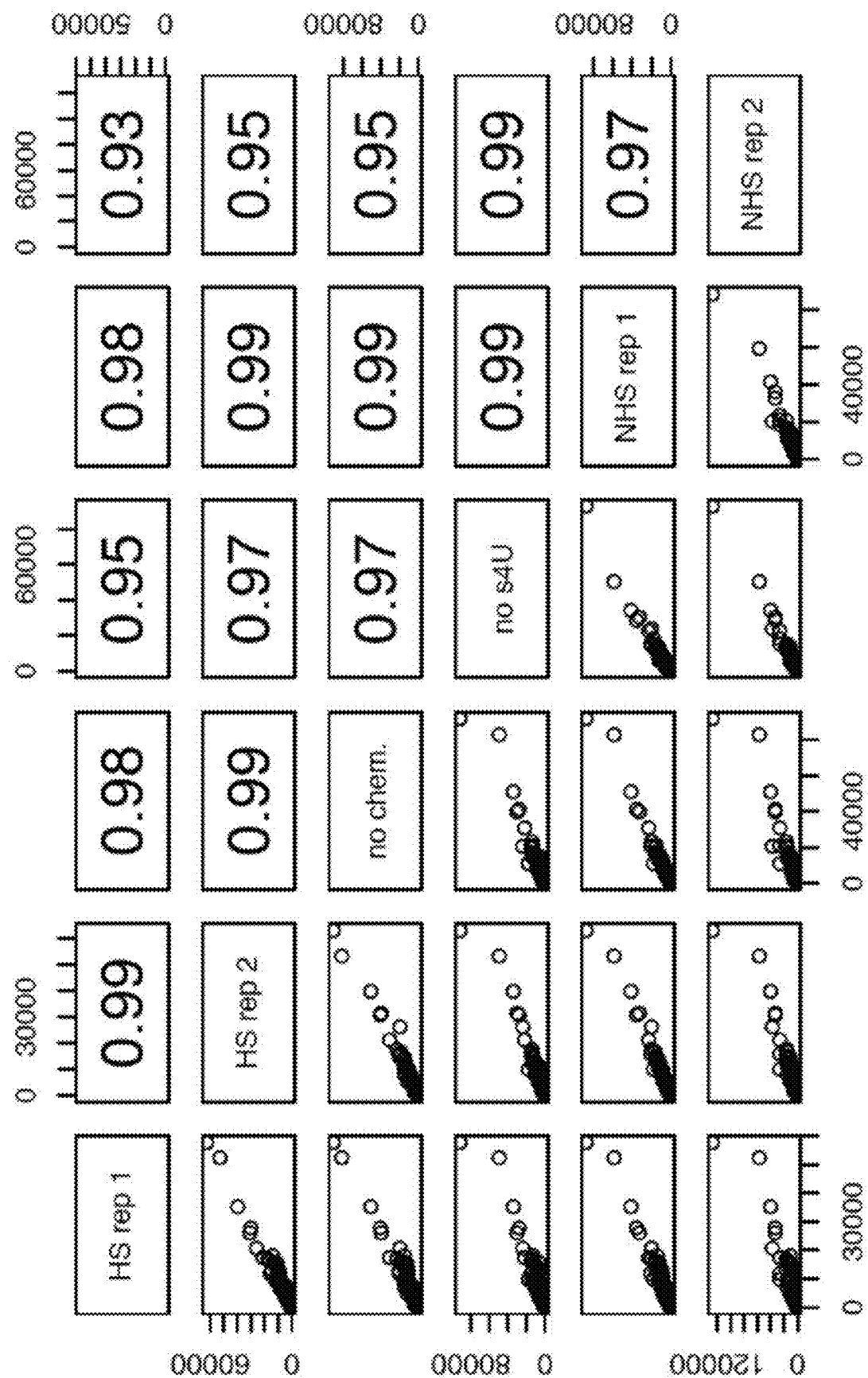
FIG. 18 depicts example correlation plots demonstrating high correspondence between the transcript-level read counts for all samples analyzed. Using HTSeq-count, aligned reads were counted from each of the samples. HS, heat shock samples; no chem, same RNA as HS samples, but without TimeLapse chemical treatment prior to library preparation; no s⁴U, samples that are treated as in the HS samples, except that the cells were never exposed to s⁴U; NHS, sample from cells that were not subjected to heat shock. The top right of the grid shows Pearson's r values for each correlation. Reads for ribosomal RNA were omitted from this analysis.
Figures 19A, 19B, 19C, 19D:
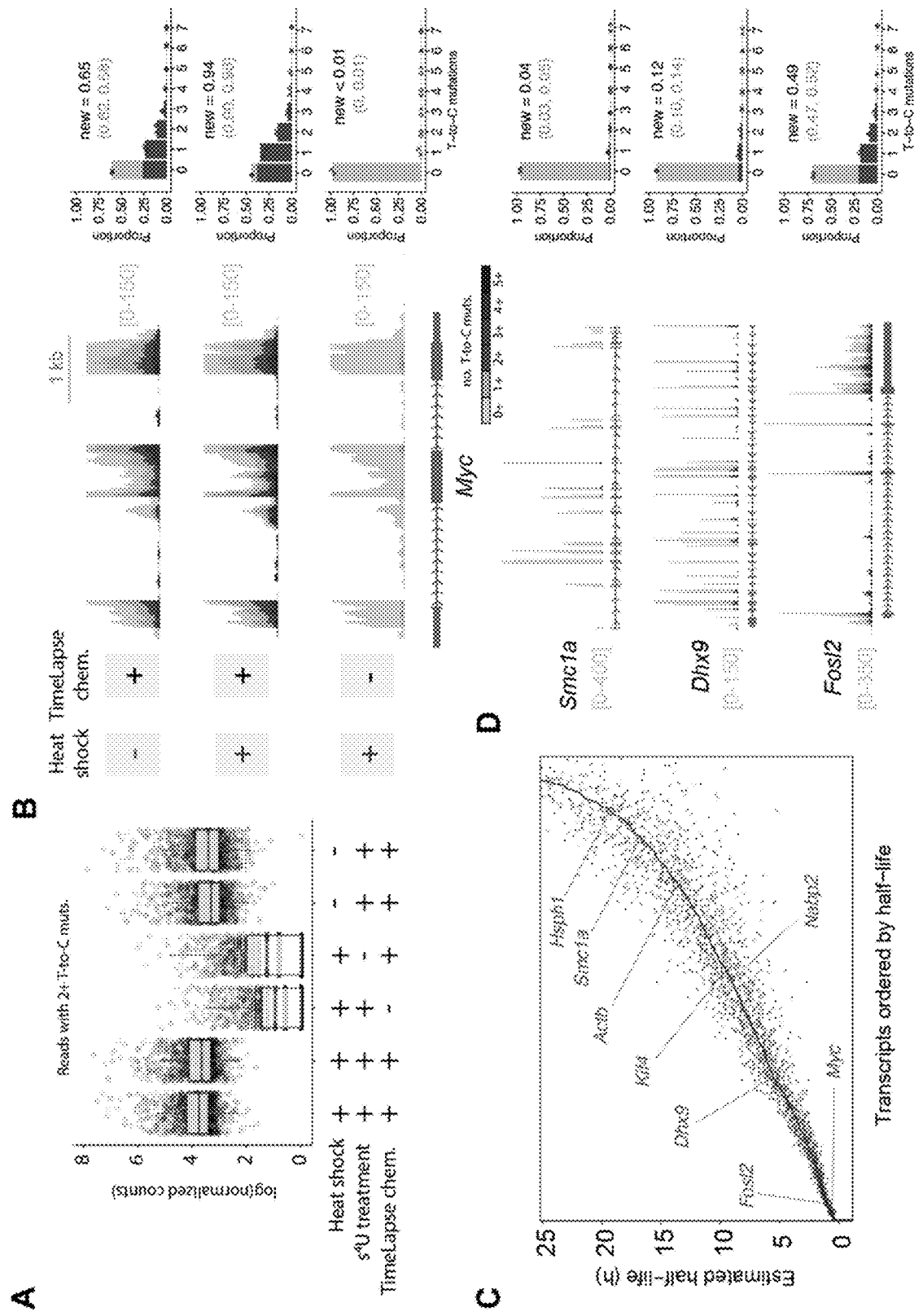
FIG. 19A through FIG. 19D, depicts the results of example experiments demonstrating a global analysis of RNA dynamics using TimeLapse-Seq.
Figure 20:
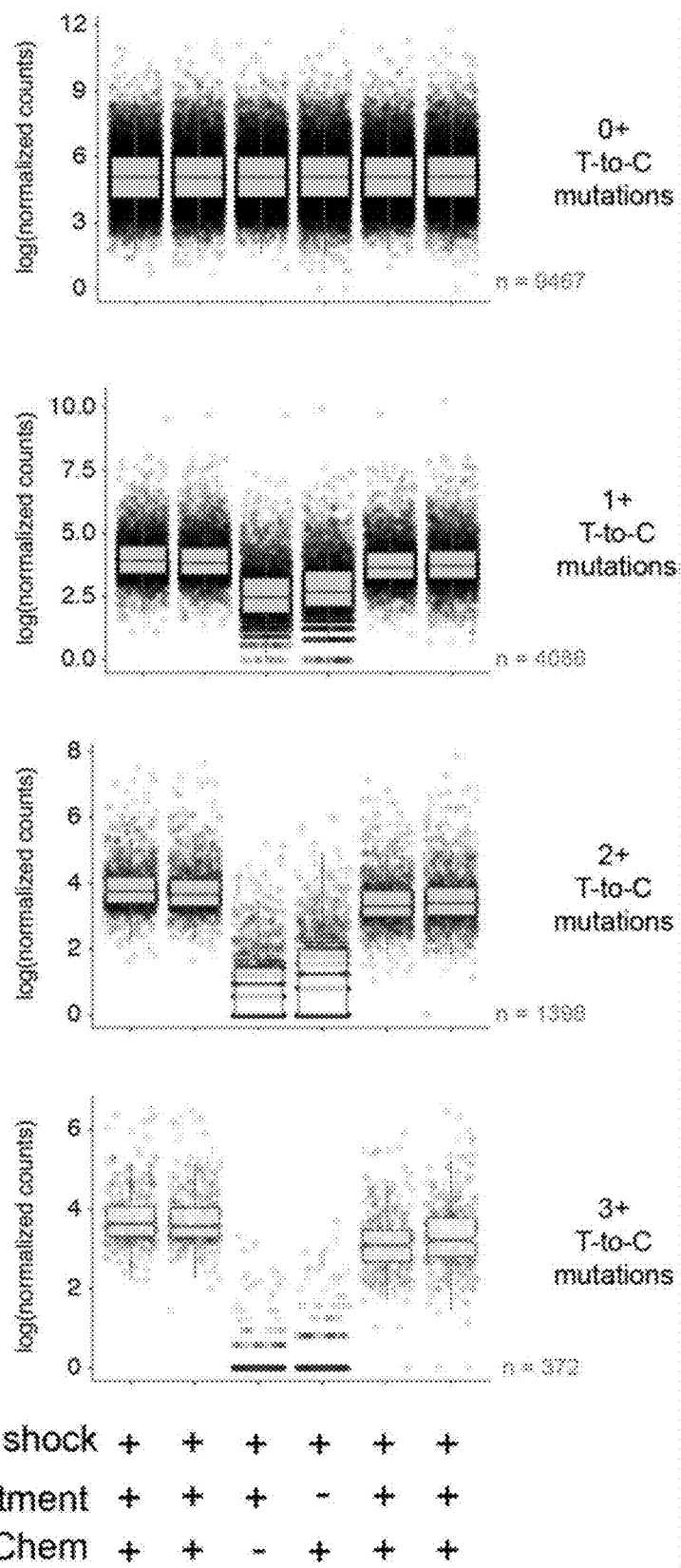
FIG. 20 depicts the results of example experiments demonstrating an analysis of the distribution of reads in each sample including either all reads (top) or reads with increasing numbers of T-to-C mutations. Read counts were normalized to the total RNA-seq analysis (top) and log transformed after adding a pseudocount of one to each transcript. Data for individual transcripts are overlaid with box and whiskers plots. Transcripts were only included if at least two samples had more than 20 counts. The number of transcripts in each analysis are indicated next to each graph.
Figure 21:
FIG. 21 depicts an example correlation analysis of the number of T-to-C mutations found in each transcript between replicates. Left, analysis of samples from cell subjected to heat shock; right, analysis of samples from cells that were not subjected to heat shock.
Figure 22:
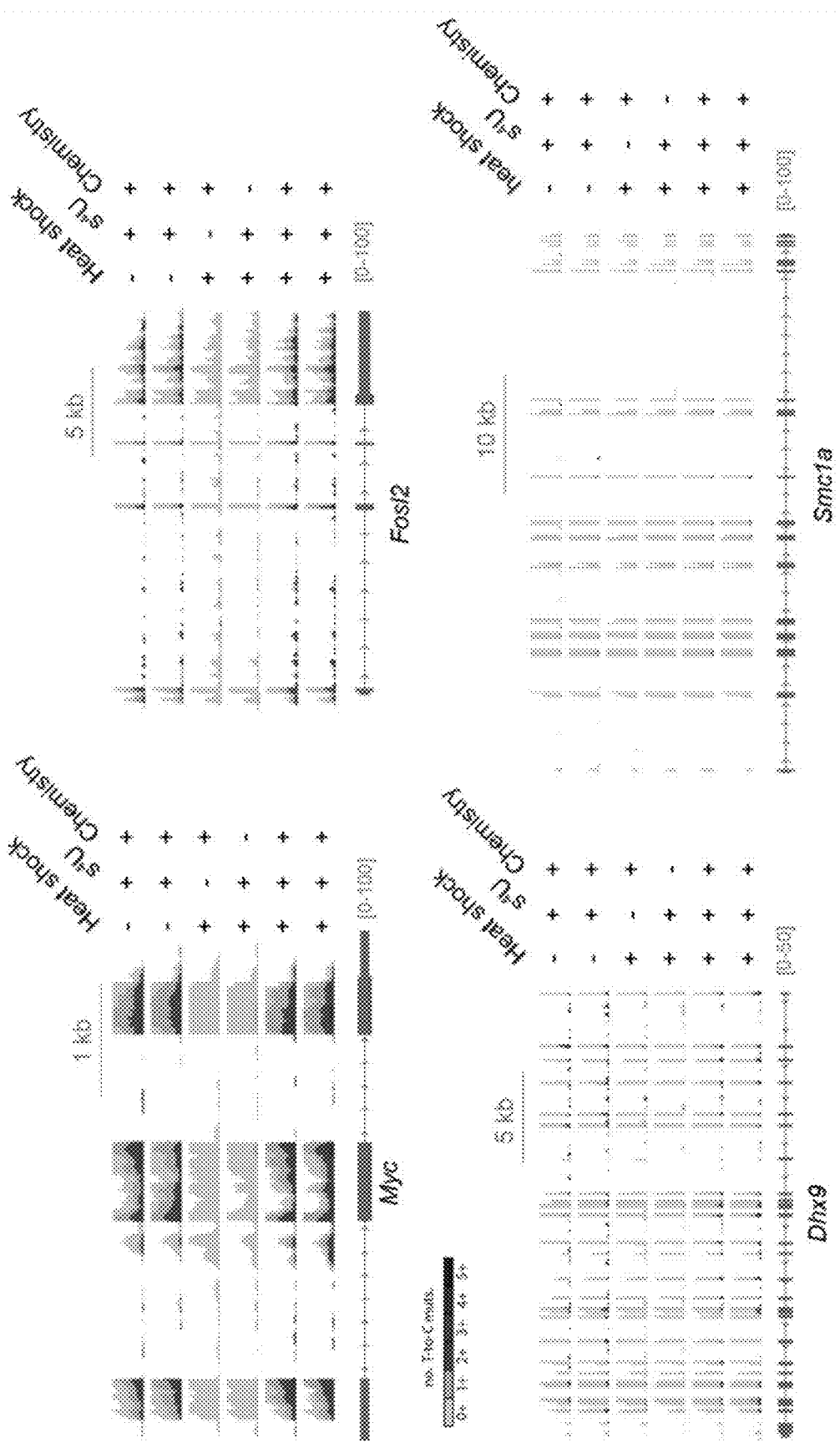
FIG. 22 depicts representative browser shots of Time-Lapse-seq coverage of transcripts shown in FIG. 19. Replicate heat shock and non-heat shock samples, as well as negative controls of heat shock samples without s⁴U or without TimeLapse chemistry are shown.

Analysis of the total RNA reads that cover each transcript from these samples revealed that all RNA-seq samples were highly correlated irrespective of heat shock, treatment with s$^4$U, or chemical treatment (Pearson's r≥0.93, FIG. 18), consistent with previous work using mild heat shock (Trinklein et al. 2004, Mol Biol Cell, 15:1254-1261; Mahat et al., 2016, Mol Cell, 62:63-78). This also demonstrates that TimeLapse-seq retains information from a traditional RNA-seq experiment. The counts of T-to-C mutations were then determined. Consistent with the targeted analysis, it was found that the increase in T-to-C mutations was dependent on both metabolic labeling with s$^4$U and on chemical treatment (FIG. 19A and FIG. 20). These counts were reproducible between replicates (FIG. 21, Pearson's r≥0.98).

Figure 23:
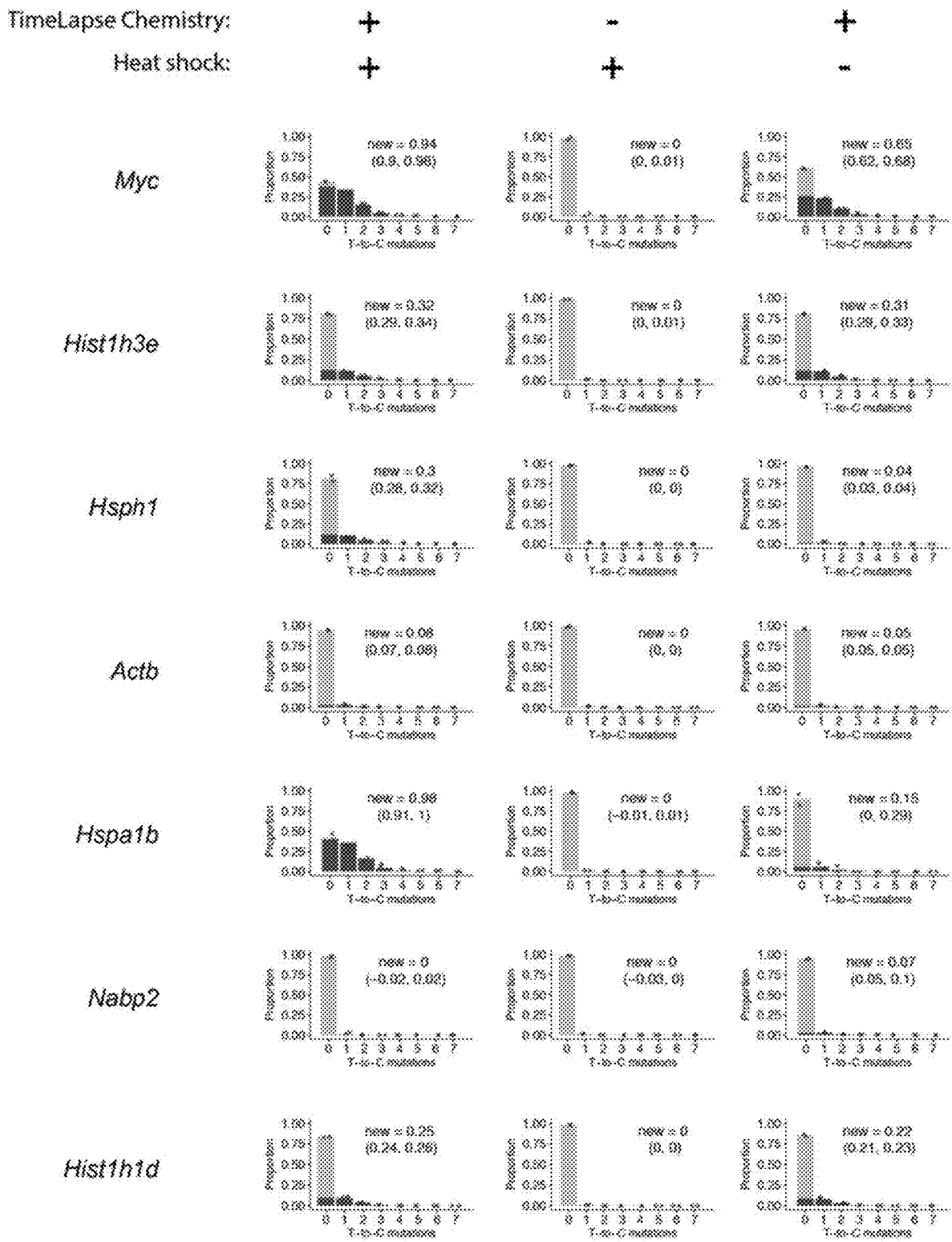
FIG. 23 depicts the results of example experiments demonstrating distributions of the number of T-to-C mutations found in reads that align to each transcript. Distribution of reads with each number of T-to-C mutations (points) overlaid on a model based on a two-component mixture of Poisson distributions to determine the proportion of reads from new transcripts and pre-existing transcripts (gray). The estimated fraction of new reads is indicated for each plot, with the Wald 95% confidence interval shown below in parentheses. The center column depicts the analysis of negative controls from samples that were not treated with s⁴U or where not subjected to chemistry.

By providing simultaneous information about total RNA and the new RNA that was made during the time cells were exposed to s$^4$U, TimeLapse-seq provides information about RNA turnover. Indeed, TimeLapse-seq revealed much higher ratios of reads with T-to-C mutations in transcripts with high turnover rates such as Myc and Fosl2 (FIG. 19B-FIG. 19C, FIG. 22, and FIG. 23) compared with stable transcripts such as Smc1a (FIG. 19C-FIG. 19D). The reads were modeled as arising from populations with two different mutation rates: pre-existing RNAs with a low mutation rate (determined by the no-s$^4$U controls), and new RNAs with a high T-to-C mutation rate (FIG. 19B, FIG. 19D, and FIG. 23). This analysis afforded a reproducible estimate of the fraction of new RNA from each gene and allows the estimation of transcript half-lives (FIG. 19C).

Figures 24A, 24B, 24C, 24D, 24E, 24F, 24G, 24H:
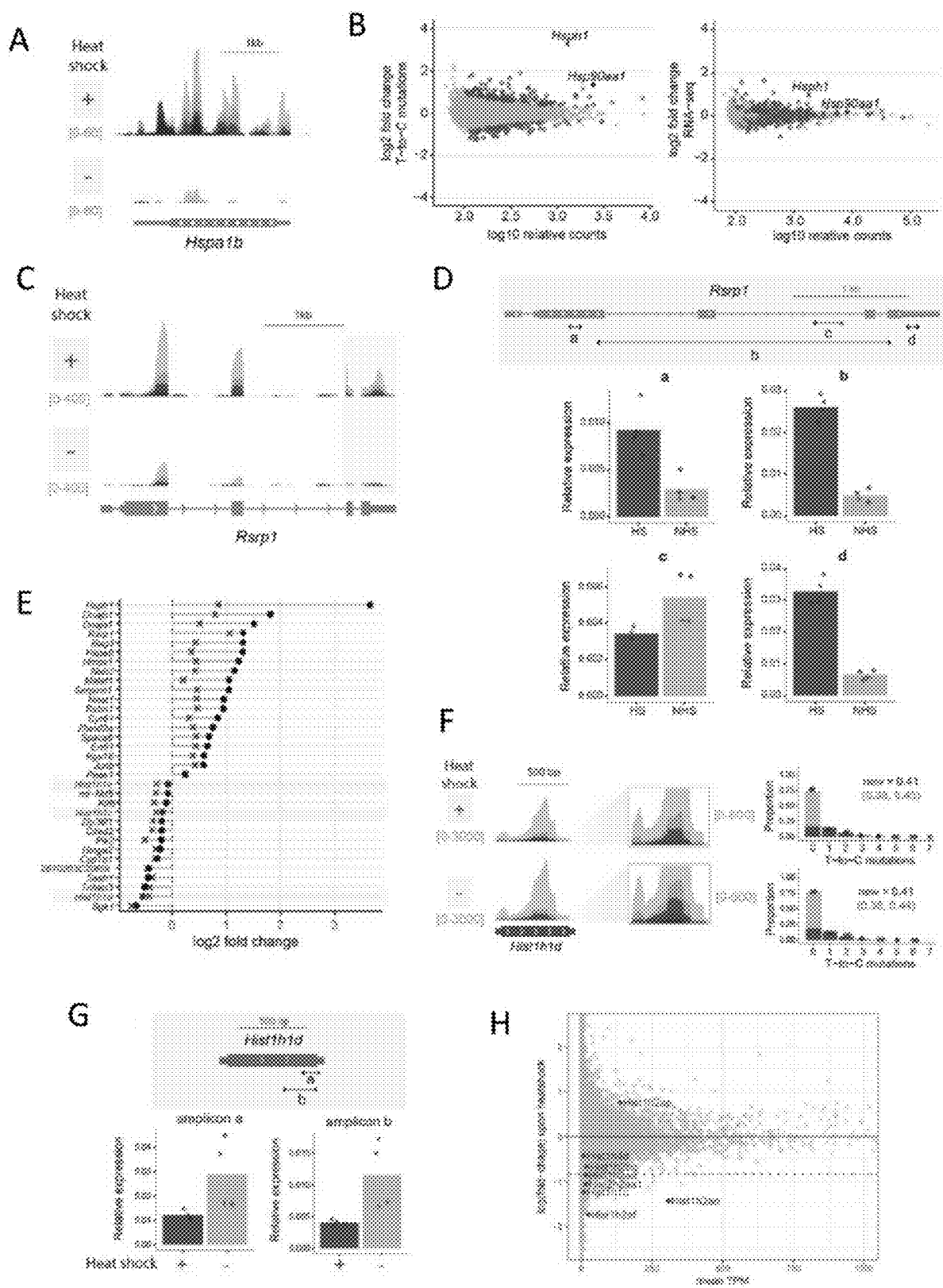
FIG. 24A through FIG. 24H, depicts the results of exemplary experiments demonstrating changes in RNA populations and differential RNA processing due to heat shock in MEF cells observed by TimeLapse-seq.

Induction of a few transcripts such as Hspa1b by RNA-seq was observed (FIG. 24A and FIG. 25B-FIG. 25C), but TimeLapseseq revealed the induction of many transcripts encoding heat shock proteins in the new transcript pool that are not apparent by RNA-seq alone (FIG. 13G and FIG. 24). For example, whereas RNA-seq is less sensitive to the small absolute changes in Hsph1 and Hsp90aa1 (as they are already abundant before heat shock; RNA-seq fold-change, Hsph1=1.8-fold, Hsp90aa1=1.1-fold, DEseq2), TimeLapse-seq reveals substantial induction of both transcripts in the new transcript pool (TimeLapse-seq fold change, Hsph1=12.7-fold; Hsp90aa1=3.1-fold, DEseq2) (FIG. 13H). Unlike PRO-seq and NET-seq, however, which are not sensitive to changes in RNA populations after transcription has completed, TimeLapse-seq captures changes in RNA processing—we observed the induction of a new terminal exon in Rsrp1 upon heat shock (FIG. 24D and FIG. 24D) as well as post-transcriptional down-regulation of histone mRNAs upon heat shock (FIG. 24F and FIG. 24G), neither of which would be apparent from analysis of nascent RNA.

Figures 25A, 25B, 25C, 25D, 25E, 25F:
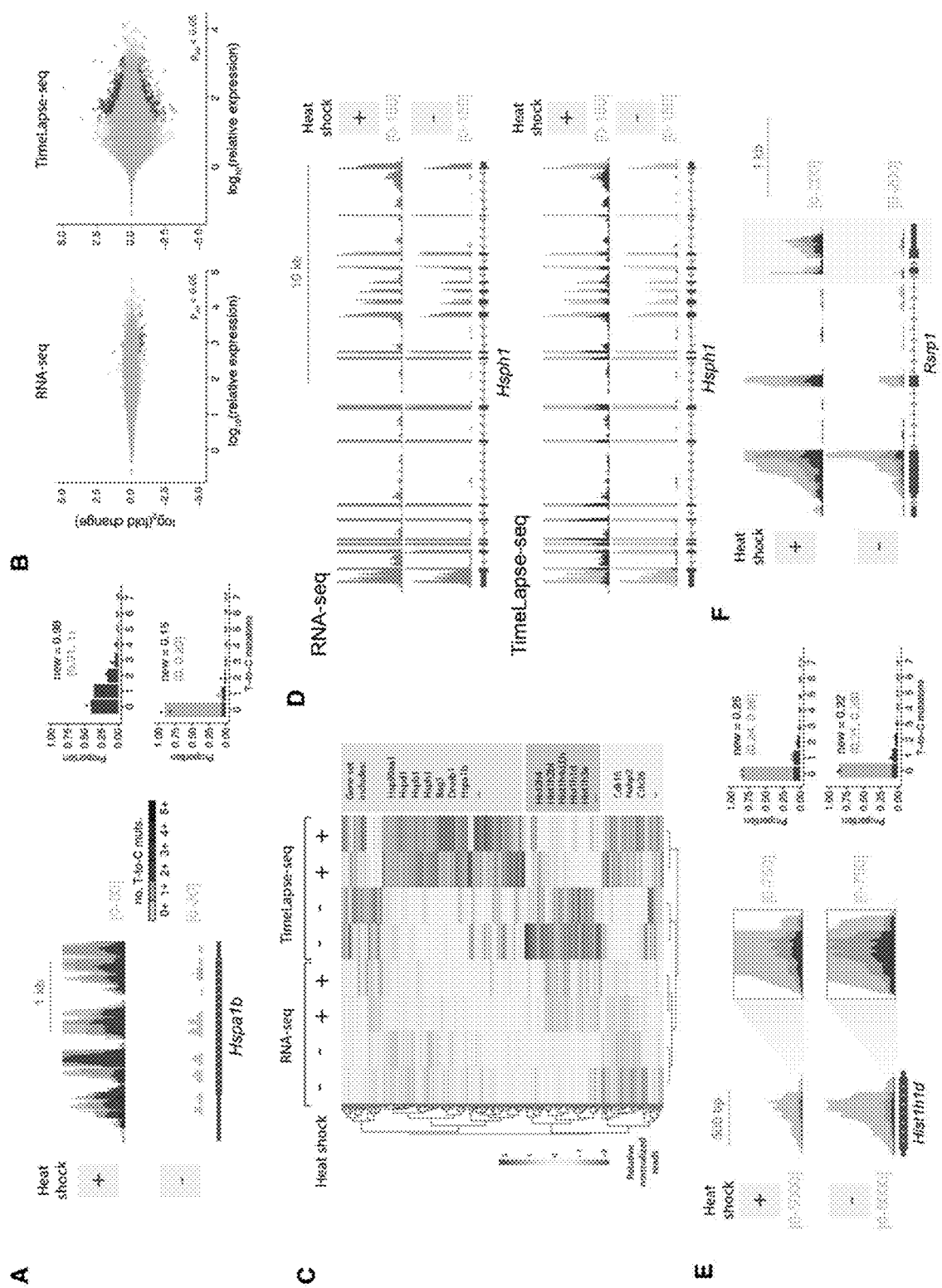
FIG. 25A through FIG. 25F, depicts the results of example experiments demonstrating that Time-Lapse-seq reveals heat shock induced changes that are not apparent by RNA-seq.
Figure 26A:
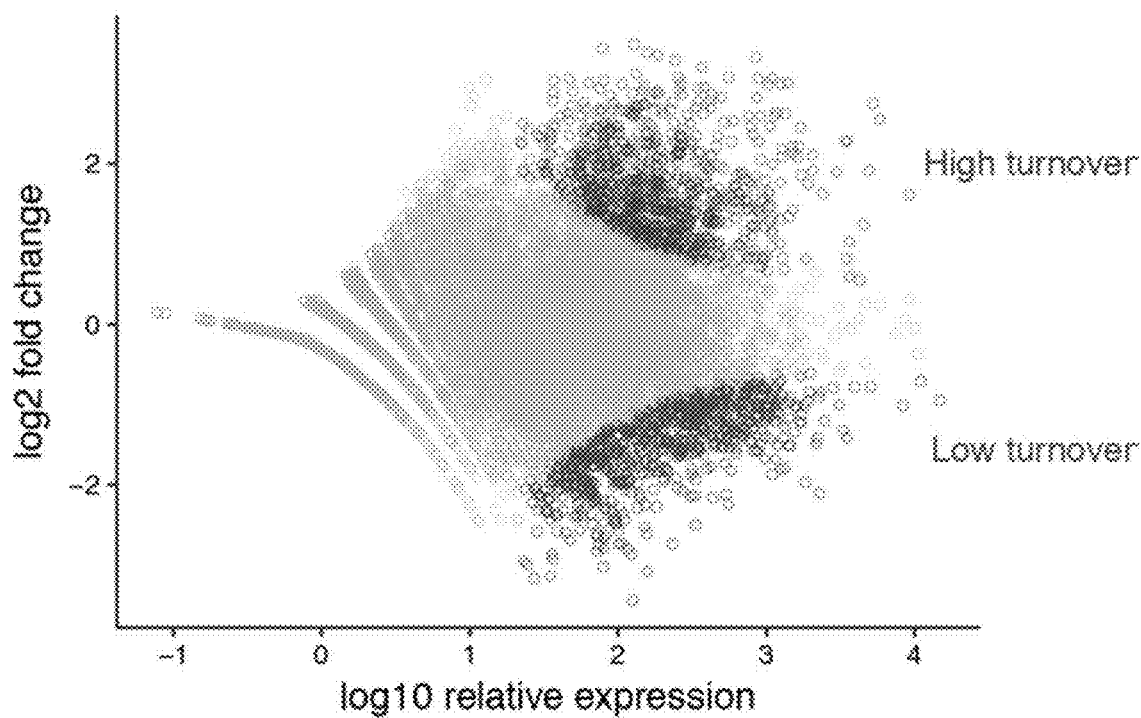
FIG. 26A through FIG. 26B, depicts the results of example experiments demonstrating an analysis of transcripts with high and low turnover rates.
Figure 26B:
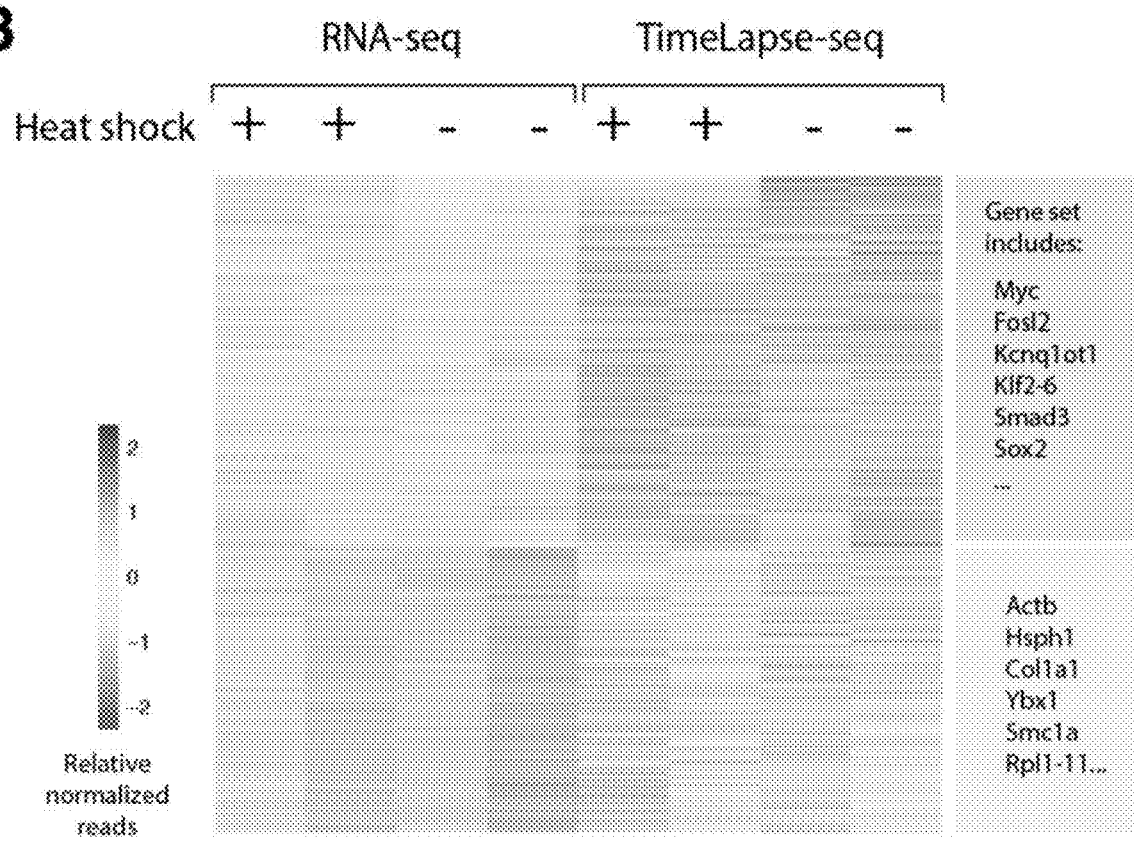

Similarly, as described above, this analyses showed that global transcript levels are highly correlated with and without heat shock. This high correlation, driven by abundant pre-existing transcripts, masks extensive transcriptional changes, as has been demonstrated with PRO-seq analysis under similar heat shock conditions (Mahat et al., 2016, Mol Cell, 62:63-78). TimeLapse-seq was also able to reveal the greater dynamics of the new transcript pool (FIG. 25B); many more RNAs were significantly changed ($p_{adj}$<0.05, RNA-seq n=45, TimeLapse-seq n=424) and this set was enriched for stress-response genes (p<2×10$^{-5}$). For example, Hsph1 is already abundant prior to heat shock, so RNA-seq is not sensitive to the small absolute change in Hsph1 transcript levels (FIG. 25D). In contrast, TimeLapse-seq reveals dramatic induction of this heat shock gene during the short 1 hour period (FIG. 25D). A similar analysis showed significant induction of many known heat shock genes, and also identified RNAs that are underrepresented in the new transcript pool (e.g., Nabp2; FIG. 25C). Some of the corresponding underrepresented genes are involved in cell cycle progression (e.g., Cdk16, FIG. 25C), consistent with PRO-seq analyses (Mahat et al., 2016, Mol Cell, 62:63-78). These results demonstrate that TimeLapse-seq can reveal changes in regulated transcription during an experiment.

Although most heat-shock-induced differences were dominated by changes in the pool of new RNAs (consistent with regulation at the level of transcription), surprisingly, some changes were driven instead by changes in pre-existing RNAs. It was found that many histone mRNAs were depleted (27 of top 57 transcripts that are depleted upon heat shock in RNA-seq analysis), and this depletion was driven by loss of the pre-existing RNA population, consistent with induced degradation of histone mRNAs rather than transcriptional shutdown (e.g., Hist1h1d, FIG. 23 and FIG. 25C and FIG. 25E). Although the total amount of this RNA was significantly depleted after heat shock (padj<0.006, DESeq2), the fraction of new RNA was essentially unchanged (0.22 vs 0.25, FIG. 25E), ruling out transcriptional shut-off as the mechanism of down regulation. Replication-dependent histone mRNAs are not polyadenylated, but rather have a distinct stem-loop structure that is important for their targeted degradation during the mammalian cell cycle, providing precedent for induced post-transcriptional down regulation (Pandey and Marzluff, 1987, Cell Biol, 7:4557-4559; Sitrtman et al., 1983, Proc Natl Acad Sci U.S.A., 80:1849-1853). While unexpected, this finding is consistent with previous RNA-seq experiments that showed a relative loss of some histone mRNAs, including Hist1h1d, upon mild or severe heat shock in mouse cells (FIG. 24H, (Shalgi et al., 2014, Cell Rep, 7:1362-1370)). These results provide one example of how TimeLapse-seq can illuminate different levels of regulation in RNA dynamics.

Discovering Isoform-Specific Transcript Dynamics

Figures 27A, 27B:
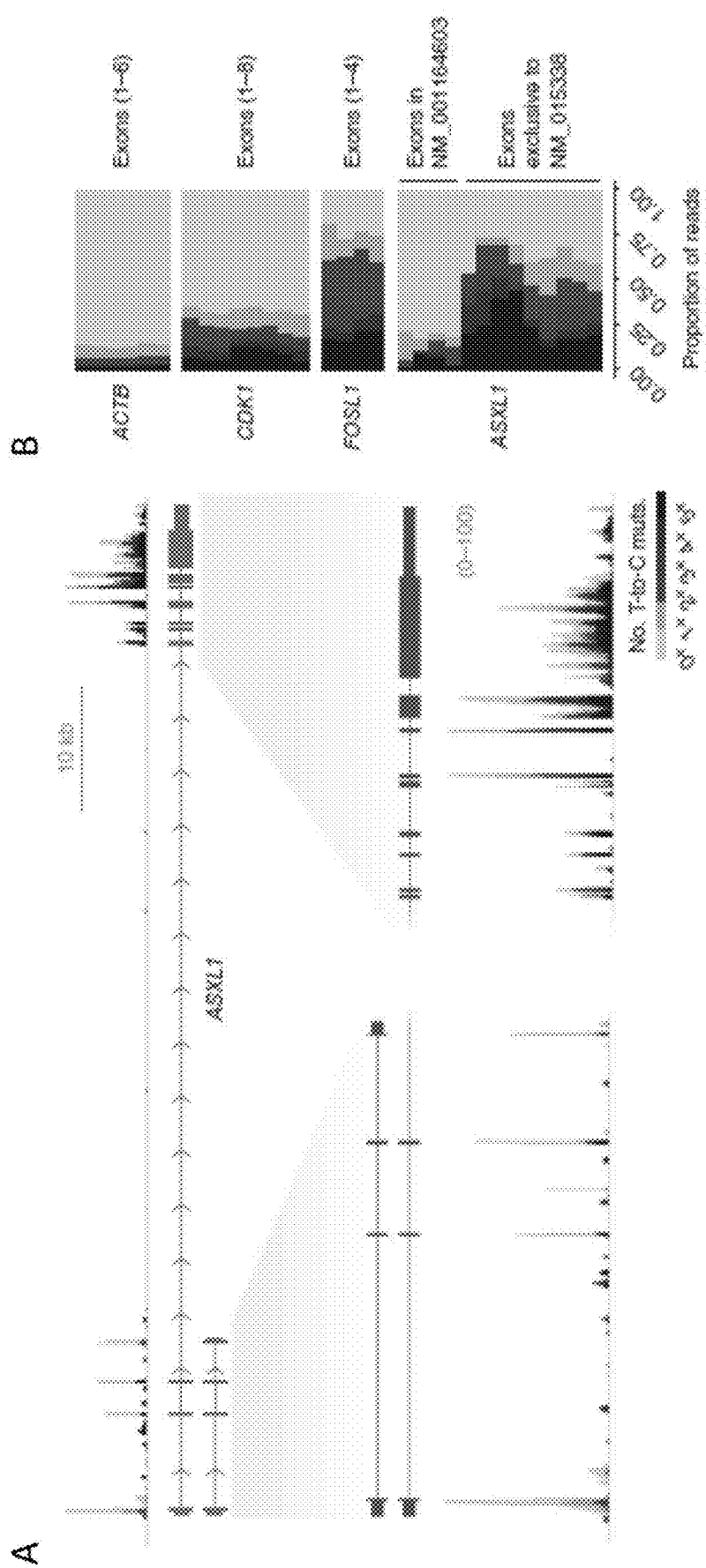
FIG. 27A through FIG. 27B, depicts the results of example experiments demonstrating TimeLapse-seq reveals differential transcript isoform stability of the ASXL1 transcript.
Figures 28A, 28B, 28C:
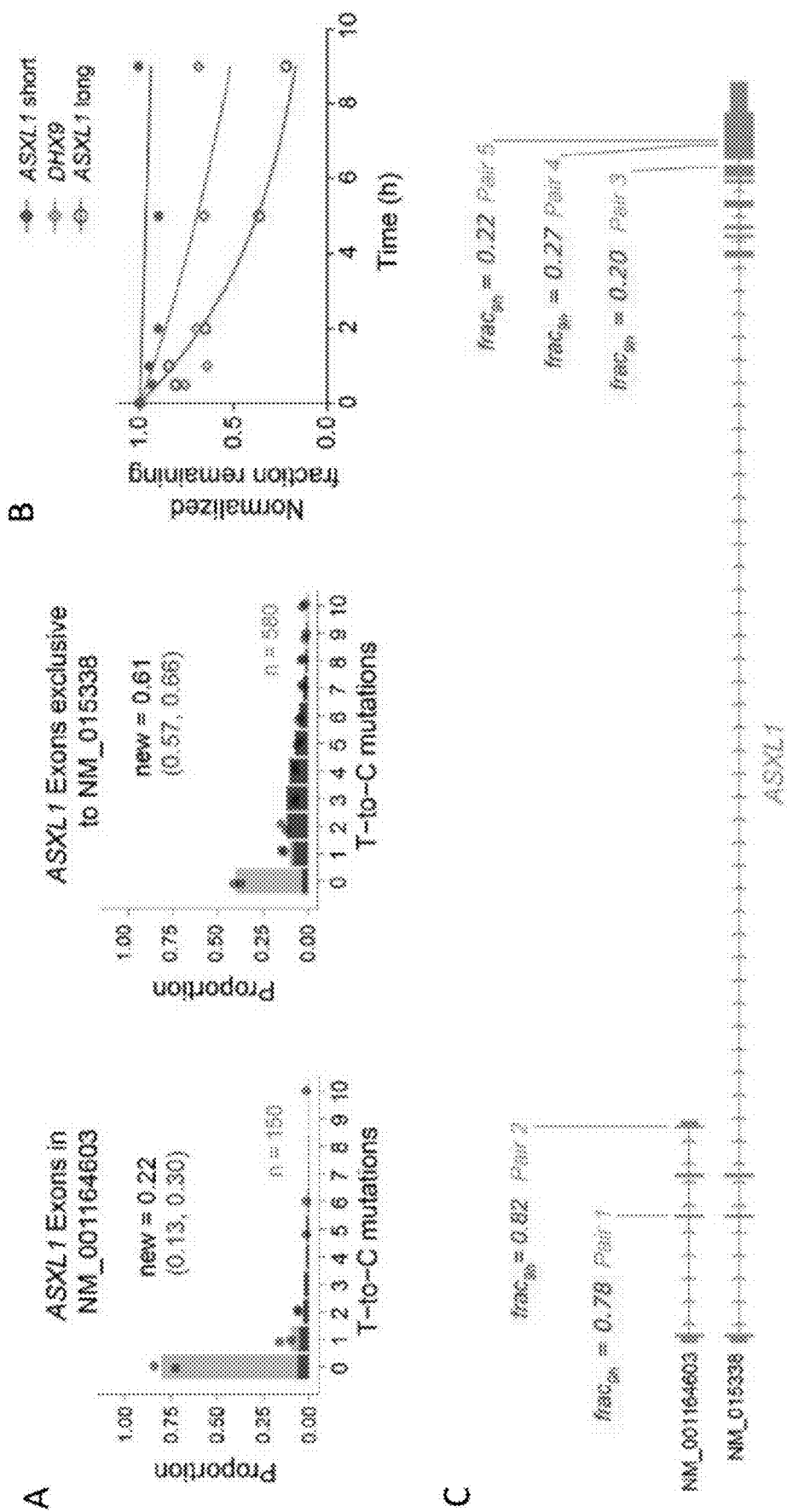
FIG. 28A through FIG. 28C, depicts the results of example experiments demonstrating ASXL1 transcript isoforms display differential stability.

TimeLapse-seq was applied using treatment conditions optimized for studying mRNA turnover (4 hour $s^4U$) (Russo et al., (2017) Methods, 120:39-48) in a chronic myelogenous leukemia model cell line (K562). Highly reproducible half-life estimates were obtained that correlated with previous observations (Friedel et al., (2009) Nucleic Acids Res. 37:e115; FIG. 15). Inspection of individual transcripts revealed reads mapping to both a shorter isoform of ASXL1 (NM_001164603), as well as a longer isoform (NM_015338) of ASXL1. The ASXL1 protein is involved in epigenetic regulation of chromatin, and mutations in the longer isoform of this gene are implicated in myelodysplastic syndromes (MDSs) (Gelsi-Boyer et al., (2009) Br. J. Haematol. 145:788-800). Analysis of the mutational content of the individual exons from ASXL1 demonstrated that reads mapping to the longer isoform had substantially greater turnover than those mapping to the first four exons (FIG. 27A and FIG. 27B), a conclusion supported by transcriptional inhibition (FIG. 28). The different stability of ASXL1 isoforms is particularly intriguing given the importance of RNA processing to many pathologies, including MDS25.

TimeLapse-seq is based on the establishment of $s^4U$ as a latent convertible nucleoside. The chemistry described here accomplishes the opposite of the chemistry used in bisulfite mapping of methylated bases; that is, it results in conversion of a U to a C analogue rather than C to U, as in bisulfite mapping experiments (Frommer et al., 1992, Proc Natl Acad Sci U.S.A., 89:1827-1831; Hayatsu et al., 1970, Biochemistry, 9:2858-2865). The method reveals different rates of RNA turnover, changes in RNA processing, and acute changes in the transcriptome that are not apparent using standard RNA-seq. TimeLapse-seq is conceptually similar to SLAM-seq (Herzog et al., (2017) Nat. Methods 14:1198-1204), a method that was reported during the revision of this manuscript. Whereas SLAM-seq uses alkylation of the $s^4U$ thione to induce mutations, TimeLapse-seq instead uses an oxidative nucleophilic aromatic substitution reaction to fully recode the hydrogen bonding pattern of $s^4U$ to match the native pattern of cytidine. TimeLapse-seq allowed for the first enrichment-free analysis RNA dynamics transcriptome wide, covering entire transcripts including their intronic sequences. TimeLapse-seq is broadly applicable to any application compatible with metabolic labeling (e.g., TT-seq).

TimeLapse-seq provides a more accessible approach that complements existing methods to study RNA dynamics. Methods that require biochemical enrichment such as TT-seq, PRO-seq and NET-seq are better suited for studying the dynamics of RNA polymerase (e.g., transcriptional pausing) or transcriptional products that do not accumulate. On the other hand, whenever experiments are compatible with metabolic labeling, TimeLapse-seq can capture changes in the new transcript pool that develop over time, including changes in RNAs processing. An important advantage of TimeLapse-seq is that it requires substantially less starting RNA and is internally controlled—the T-to-C mutations are measured relative to the total RNA population of the same sample, thereby avoiding the challenges of external normalization. TimeLapse-seq makes analysis of temporal dynamics accessible to a standard sequencing pipeline, establishing it as a powerful tool to analyze the changing RNA populations that reflect the biological state of a sample. Without being bound to a particular theory, it is believed that TimeLapse-seq will provide a broad and flexible platform to investigate dynamic biological systems.

Example 2

Protocol

Provided below is an exemplary protocol for preparation of a TimeLapse-seq library.

Materials

K562 cells, HyClone RPMI 1640 Media, Fetal bovine serum (FBS), certified, Penicillin-Streptomycin, 100× solution, Phosphate buffered saline (PBS), 1×, 4-thiouridine, DEPC-treated water, Qiagen RNeasy Mini kit, 2-mercaptoethanol (BME), Ethanol, 200 proof, molecular biology grade, 3 M sodium acetate, pH 5.2, 2,2,2-trifluoroethylamine (TFEA), 0.5 M EDTA, pH 8, Sodium periodate (NaIO4), 0.2 mL PCR tube strips, 1.5 mL microcentrifuge tubes, PCR clean, 15 mL conical centrifuge tubes, 1 M dithiothreitol (DTT), 22-gauge disposable needle, Luer slip syringe, Agencocurt RNAClean XP beads, Magnetic PCR tube separation rack, SMARTer Stranded Total RNA-Seq Kit—Pico Input Mammalian, PCR Thermocycler, Nanodrop spectrophotometer, Mini centrifuge for PCR strips, Benchtop microcentrifuge.

Methods

K562 cells were cultured at 37° C. to approximately 50% confluence in RPMI media supplemented with 10% FBS and 1% P/S.

4-thiouridine was dissolved in a minimal volume of water and 5 mL was added cultured cells at 100 mM final concentration. Cells were agitated gently to evenly distribute the metabolic label and incubated 4 hours at 37° C. Steps were taken to protect 4-thiouridine treated cells and RNA in all subsequent steps from light exposure. The 4-thiouridine treatment time and concentration will vary by cell type and desired application. The provided protocol is an exemplary method to examine relatively long RNA half-lives.

Cells were transferred to a 15 mL conical Eppendorf tube and place on ice for 1 min.

Cells were pelleted by centrifugation at 4° C. for 3 minutes at 300×g in a pre-chilled centrifuge. Cell culture medium was aspirated from the cell pellet.

The cell pellet was rinsed with ice-cold 1× PBS then pelleted and aspirated as above prior to modified RNeasy isolation.

Modified RNeasy Isolation

The cell pellet was resuspended in 350 µl RLT buffer supplemented with 1% BME. The cell suspension was passed through a 22-gauge needle 5 times to lyse the cells and the mix was transferred to a 1.5 mL Eppendorf tube.

350 µl freshly prepared 70% ethanol was added to the lysis mixture and mixed well by inversion. 700 µl of mixture was transferred to an RNeasy spin column, and centrifuged at >10,000 RPM for 15 seconds. The flow through was discarded.

700 μl RW1 was added to the column and the column was centrifuged at >10,000 RPM for 15 seconds. The flow through was discarded.

500 μl RPE supplemented with 1% BME to was added to the column and the column was centrifuged at >10,000 RPM for 15 seconds. The flow through was discarded.

700 μl freshly prepared 80% ethanol to was added to the column and the column was centrifuged at maximum speed for 2 minutes. The column was transferred to a fresh collection tube and centrifuged at maximum speed for an additional 5 minutes.

The column was transferred to a 1.5 ml Eppendorf tube and 30 μl DEPC-treated water was added directly to the column membrane. The column was allowed to stand 1 min, then centrifuged >10,000 RPM for 1 minute. RNA concentration in the flow through was assessed by nanodrop.

TimeLapse Chemistry

A master mix was created by combining the following on ice (15 μl total per sample, +10% to account for pipetting errors): 0.84 μl 3M sodium acetate, pH 5.2; 12.7 μl DEPC-treated water; 0.2 μl 0.5M EDTA, pH 8; 1.3 μl TFEA, and combining well by vortexing. TFEA is volatile, therefore it was pipetted up and down several times prior to dispensing the reagent to ensure vapor pressure equilibration and accurate volumes.

15 μl of the above master mix was added to 8.7 μl RNA sample (e.g. 2 μg RNA in DEPC-treated water) in a 0.2 ml PCR tube strip. The reaction was combined well by flicking the PCR tubes, and was briefly spun to collect the sample at the bottom of the tube.

1.3 μl of a 192 mM solution of $NaIO_4$ in DEPC-treated water was added to the reaction. The reaction was combined well by flicking the PCR tubes, and was briefly spun to collect the sample at the bottom of the tube.

The sample was incubated at 45° C. for 1 hour in a pre-heated PCR thermocycler with a heated lid. The sample was cooled to 4° C. after incubation.

An equal volume (25 μl) of RNAClean beads was added to each sample and the mixture was gently vortexed to combine and incubated at room temperature for 10 minutes. An aliquot of RNAClean beads was brought to room temperature for 30 minutes prior to use.

A brief spin was performed to collect the sample at the bottom of the tube, and the tube was placed on a magnetic isolation rack until the solution was clear (~5 min).

The supernatant was removed without disturbing the bead pellet, and 2 washes were performed with 200 μl of freshly prepared 80% ethanol.

After removing the second ethanol wash, a spin was performed to collect the bead pellet at the bottom of the tube, and the beads were recaptured on the magnetic isolation rack for 1 minute. Residual ethanol was removed with a pipette and the bead pellet was allowed to dry until just cracked (2-4 minutes).

18 μl of DEPC-treated water was added to the dried beads. The samples were flicked until the beads were resuspended, and allowed to rehydrate for 2 minutes.

A brief spin was performed to collect the sample at the bottom of the tube, and the tube was placed on a magnetic isolation rack until the solution was clear (~2 min).

The supernatant was collected carefully and transferred to a fresh PCR tube strip.

2 μl of a freshly made 10× reducing master mix (100 μl recipe): 10 μl 1 M Tris-HCl, pH 7.4; 10 μl 1 M DTT; 20 μl 5 M NaCl; 2 μl 0.5 M EDTA, pH 8; 58 μl DEPC-treated water was added to the tube. Samples were incubated at 37° C. for 30 minutes.

Following incubation, the RNA was isolated using 20 μl of RNAClean beads following the steps as described above, and the samples were eluted into 12 μl DEPC-treated water. The RNA concentration and integrity was assessed by bioanalyzer.

The sample then proceeded to undergo RNA-seq library preparation using the SMARTer Stranded Total RNA-Seq Kit-Pico Input Mammalian according to the manufacturer's methods.

While the invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method for identifying newly synthesized nucleic acid molecules comprising:
   a) contacting a cell with a modified base, wherein the modified base is incorporated into at least one newly generated nucleic acid molecule;
   b) isolating the nucleic acid molecules from the cell;
   c) contacting the isolated nucleic acid molecules with an oxidant and a nucleophile, wherein the nucleophile is selected from the group consisting of 2,2,2-trifluoroethylamine (TFEA), benzylamine ($C_6H_5CH_2NH_2$), aniline ($C_6H_5NH_2$), 1,1-dimethylethylenediamine (($CH_3)_2NCH_2CH_2NH_2$), ethanolamine ($C_2H_7NO$) and 4-(Triflouromethyl)benzylamine ($CF_3C_6H_4CH_2NH_2$), and further wherein the modified base is converted to an analog of a different base;
   d) detecting the presence of the analog of a different base or a. mutation that is the result of amplification thereof; and
   e) identifying a nucleic acid molecule comprising the analog of a different base as being a newly generated nucleic acid molecule.

2. The method of claim 1, wherein the oxidant is selected from the group consisting of hydrogen peroxide ($H_2O_2$), sodium iodate ($NaIO_3$), potassium permagnate ($KMnO_4$), sodium periodate ($NaIO_4$), and meta-Chloroperoxybenzoic acid (mCPBA).

3. The method of claim 1, wherein the oxidant is $NaIO_4$ and the nucleophile is TFEA.

4. The method of claim 1, wherein the nucleic acid molecule is selected from the group consisting of: a ribonucleic acid molecule and a deoxyribonucleic acid molecule.

5. The method of claim 1, wherein the modified base is selected from the group consisting of 4-thiouridine ($s^4U$), 6-thioguanine ($s^6G$), 6-thiodeoxyguanosine ($s^6dG$) and 4-thiothymine ($s^4T$).

6. The method of claim 1, wherein the mutation is selected from the group consisting of: a U to C mutation and a G to A mutation.

7. The method of claim 1, wherein the modified base is selected from the group consisting of $s^4T$ and $s^4U$ and the modified base is converted into an analog of cytidine.

8. The method of claim 1, wherein the modified base is selected from the group consisting of $s^6G$ and $s^6dG$, and wherein the modified base is converted into an analog of adenine.

9. The method of claim 1, wherein the step of detecting comprises sequencing the nucleic acid molecules.

* * * * *

SEQUENCE LISTING

```
<160> NUMBER OF SEQ ID NOS: 59

<210> SEQ ID NO 1
<211> LENGTH: 48
<212> TYPE: DNA
<213> ORGANISM: Artificial Sequence
<220> FEATURE:
<223> OTHER INFORMATION: mActB1 Forward Sequence
<220> FEATURE:
<221> NAME/KEY: misc_feature
<222> LOCATION: (23)..(27)
<223> OTHER INFORMATION: any nucleotide sequence of any length (e.g.,
      barcode sequence)

<400> SEQUENCE: 1
ctacacgacg ctcttccgat ctnnnnnact gagctgcgtt ttacaccc                48

<210> SEQ ID NO 2
<211> LENGTH: 49
<212> TYPE: DNA
<213> ORGANISM: Artificial Sequence
```

```
<220> FEATURE:
<223> OTHER INFORMATION: mActB2 Forward Sequence
<220> FEATURE:
<221> NAME/KEY: misc_feature
<222> LOCATION: (23)..(27)
<223> OTHER INFORMATION: any nucleotide sequence of any length (e.g.,
      barcode sequence)

<400> SEQUENCE: 2
ctacacgacg ctcttccgat ctnnnnnaat ttctgaatgg cccaggtct        49

<210> SEQ ID NO 3
<211> LENGTH: 49
<212> TYPE: DNA
<213> ORGANISM: Artificial Sequence
<220> FEATURE:
<223> OTHER INFORMATION: mActB3 Forward Sequence
<220> FEATURE:
<221> NAME/KEY: misc_feature
<222> LOCATION: (23)..(27)
<223> OTHER INFORMATION: any nucleotide sequence of any length (e.g.,
      barcode sequence)

<400> SEQUENCE: 3
ctacacgacg ctcttccgat ctnnnnnatg gtgggaatgg gtcagaagg        49

<210> SEQ ID NO 4
<211> LENGTH: 49
<212> TYPE: DNA
<213> ORGANISM: Artificial Sequence
<220> FEATURE:
<223> OTHER INFORMATION: mActB4 Forward Sequence
<220> FEATURE:
<221> NAME/KEY: misc_feature
<222> LOCATION: (23)..(27)
<223> OTHER INFORMATION: any nucleotide sequence of any length (e.g.,
      barcode sequence)

<400> SEQUENCE: 4
ctacacgacg ctcttccgat ctnnnnntga agtgtgacgt tgacatccg        49

<210> SEQ ID NO 5
<211> LENGTH: 47
<212> TYPE: DNA
<213> ORGANISM: Artificial Sequence
<220> FEATURE:
<223> OTHER INFORMATION: mGapdh1 Forward Sequence
<220> FEATURE:
<221> NAME/KEY: misc_feature
<222> LOCATION: (23)..(27)
<223> OTHER INFORMATION: any nucleotide sequence of any length (e.g.,
      barcode sequence)

<400> SEQUENCE: 5
ctacacgacg ctcttccgat ctnnnnntcc gtcgtggatc tgacgtg          47

<210> SEQ ID NO 6
<211> LENGTH: 47
<212> TYPE: DNA
<213> ORGANISM: Artificial Sequence
<220> FEATURE:
<223> OTHER INFORMATION: mGapdh2 Forward Sequence
<220> FEATURE:
<221> NAME/KEY: misc_feature
<222> LOCATION: (23)..(27)
<223> OTHER INFORMATION: any nucleotide sequence of any length (e.g.,
      barcode sequence)

<400> SEQUENCE: 6
ctacacgacg ctcttccgat ctnnnnnctc ttccaccttc gatgccg          47
```

-continued

<210> SEQ ID NO 7
<211> LENGTH: 48
<212> TYPE: DNA
<213> ORGANISM: Artificial Sequence
<220> FEATURE:
<223> OTHER INFORMATION: mGapdh3 Forward Sequence
<220> FEATURE:
<221> NAME/KEY: misc_feature
<222> LOCATION: (23)..(27)
<223> OTHER INFORMATION: any nucleotide sequence of any length (e.g., barcode sequence)

<400> SEQUENCE: 7
ctacacgacg ctcttccgat ctnnnnnagg acactgagca agagaggc                48

<210> SEQ ID NO 8
<211> LENGTH: 47
<212> TYPE: DNA
<213> ORGANISM: Artificial Sequence
<220> FEATURE:
<223> OTHER INFORMATION: mGapdh4 Forward Sequence
<220> FEATURE:
<221> NAME/KEY: misc_feature
<222> LOCATION: (23)..(27)
<223> OTHER INFORMATION: any nucleotide sequence of any length (e.g., barcode sequence)

<400> SEQUENCE: 8
ctacacgacg ctcttccgat ctnnnnncag caatgcatcc tgcacca                 47

<210> SEQ ID NO 9
<211> LENGTH: 45
<212> TYPE: DNA
<213> ORGANISM: Artificial Sequence
<220> FEATURE:
<223> OTHER INFORMATION: mActB1 Reverse Sequence

<400> SEQUENCE: 9
cagacgtgtg ctcttccgat cttcctgagt caaaagcgcc aaaac                   45

<210> SEQ ID NO 10
<211> LENGTH: 50
<212> TYPE: DNA
<213> ORGANISM: Artificial Sequence
<220> FEATURE:
<223> OTHER INFORMATION: mActB2 Reverse Sequence

<400> SEQUENCE: 10
cagacgtgtg ctcttccgat ctggtgtggc acttttattg gtctcaagtc              50

<210> SEQ ID NO 11
<211> LENGTH: 43
<212> TYPE: DNA
<213> ORGANISM: Artificial Sequence
<220> FEATURE:
<223> OTHER INFORMATION: mActB3 Reverse Sequence

<400> SEQUENCE: 11
cagacgtgtg ctcttccgat ctgccacacg cagctcattg tag                     43

<210> SEQ ID NO 12
<211> LENGTH: 49
<212> TYPE: DNA
<213> ORGANISM: Artificial Sequence
<220> FEATURE:
<223> OTHER INFORMATION: mActB4 Reverse Sequence

<400> SEQUENCE: 12
cagacgtgtg ctcttccgat ctgaggagca atgatcttga tcttcatgg      49

<210> SEQ ID NO 13
<211> LENGTH: 43
<212> TYPE: DNA
<213> ORGANISM: Artificial Sequence
<220> FEATURE:
<223> OTHER INFORMATION: mGapdh1 Reverse Sequence

<400> SEQUENCE: 13
cagacgtgtg ctcttccgat ctcatcgaag gtggaagagt ggg      43

<210> SEQ ID NO 14
<211> LENGTH: 42
<212> TYPE: DNA
<213> ORGANISM: Artificial Sequence
<220> FEATURE:
<223> OTHER INFORMATION: mGapdh2 Reverse Sequence

<400> SEQUENCE: 14
cagacgtgtg ctcttccgat ctggtgggtg gtccagggtt tc      42

<210> SEQ ID NO 15
<211> LENGTH: 44
<212> TYPE: DNA
<213> ORGANISM: Artificial Sequence
<220> FEATURE:
<223> OTHER INFORMATION: mGapdh3 Reverse Sequence

<400> SEQUENCE: 15
cagacgtgtg ctcttccgat ctgtgggtgc agcgaacttt attg      44

<210> SEQ ID NO 16
<211> LENGTH: 41
<212> TYPE: DNA
<213> ORGANISM: Artificial Sequence
<220> FEATURE:
<223> OTHER INFORMATION: mGapdh4 Reverse Sequence

<400> SEQUENCE: 16
cagacgtgtg ctcttccgat ctacagcttt ccagagggc c      41

<210> SEQ ID NO 17
<211> LENGTH: 21
<212> TYPE: DNA
<213> ORGANISM: Artificial Sequence
<220> FEATURE:
<223> OTHER INFORMATION: Forward PCR Amplification primer

<400> SEQUENCE: 17
cagacgtgtg ctcttccgat c      21

<210> SEQ ID NO 18
<211> LENGTH: 22
<212> TYPE: DNA
<213> ORGANISM: Artificial Sequence
<220> FEATURE:
<223> OTHER INFORMATION: Reverse PCR Amplification primer

<400> SEQUENCE: 18
ctacacgacg ctcttccgat ct      22

<210> SEQ ID NO 19
<211> LENGTH: 22

```
<212> TYPE: DNA
<213> ORGANISM: Artificial Sequence
<220> FEATURE:
<223> OTHER INFORMATION: IVT T7 promoter

<400> SEQUENCE: 19
gaaattaata cgactcacta ta                                          22

<210> SEQ ID NO 20
<211> LENGTH: 20
<212> TYPE: DNA
<213> ORGANISM: Artificial Sequence
<220> FEATURE:
<223> OTHER INFORMATION: RE RT and reverse primer

<400> SEQUENCE: 20
cttgcgtttc tctcgtcctt                                             20

<210> SEQ ID NO 21
<211> LENGTH: 20
<212> TYPE: DNA
<213> ORGANISM: Artificial Sequence
<220> FEATURE:
<223> OTHER INFORMATION: RE fluorescent forward primer
<220> FEATURE:
<221> NAME/KEY: misc_feature
<222> LOCATION: (1)..(1)
<223> OTHER INFORMATION: Cy5 label

<400> SEQUENCE: 21
aggacaaaag acacaaccgc                                             20

<210> SEQ ID NO 22
<211> LENGTH: 20
<212> TYPE: DNA
<213> ORGANISM: Artificial Sequence
<220> FEATURE:
<223> OTHER INFORMATION: RE forward primer

<400> SEQUENCE: 22
aggacaaaag acacaaccgc                                             20

<210> SEQ ID NO 23
<211> LENGTH: 95
<212> TYPE: DNA
<213> ORGANISM: Artificial Sequence
<220> FEATURE:
<223> OTHER INFORMATION: IVT template

<400> SEQUENCE: 23
cttgcgtttc tctcgtcctt ctgtcttgct gttgttcgcg accgccctgt gcggttgtgt    60
cttttgtcct gcctatagtg agtcgtatta atttc                               95

<210> SEQ ID NO 24
<211> LENGTH: 95
<212> TYPE: DNA
<213> ORGANISM: Artificial Sequence
<220> FEATURE:
<223> OTHER INFORMATION: IVT positive control template

<400> SEQUENCE: 24
cttgcgtttc tctcgtcctt ctgtcttgct gttgttcgcg gccgccctgt gcggttgtgt    60
cttttgtcct gcctatagtg agtcgtatta atttc                               95

<210> SEQ ID NO 25
```

```
<211> LENGTH: 20
<212> TYPE: DNA
<213> ORGANISM: Artificial Sequence
<220> FEATURE:
<223> OTHER INFORMATION: Primer extension RT
<220> FEATURE:
<221> NAME/KEY: misc_feature
<222> LOCATION: (1)..(1)
<223> OTHER INFORMATION: Cy5 label

<400> SEQUENCE: 25
cttgcgtttc tctcgtcctt                                              20

<210> SEQ ID NO 26
<211> LENGTH: 47
<212> TYPE: DNA
<213> ORGANISM: Artificial Sequence
<220> FEATURE:
<223> OTHER INFORMATION: hMYC1 Forward Sequence
<220> FEATURE:
<221> NAME/KEY: misc_feature
<222> LOCATION: (23)..(27)
<223> OTHER INFORMATION: any nucleotide sequence of any length (e.g.,
      barcode sequence)

<400> SEQUENCE: 26
ctacacgacg ctcttccgat ctnnnnnctt ggcgggaaaa agaacgg                 47

<210> SEQ ID NO 27
<211> LENGTH: 47
<212> TYPE: DNA
<213> ORGANISM: Artificial Sequence
<220> FEATURE:
<223> OTHER INFORMATION: hMYC2 Forward Sequence
<220> FEATURE:
<221> NAME/KEY: misc_feature
<222> LOCATION: (23)..(27)
<223> OTHER INFORMATION: any nucleotide sequence of any length (e.g.,
      barcode sequence)

<400> SEQUENCE: 27
ctacacgacg ctcttccgat ctnnnnngca tccacgaaac tttgccc                 47

<210> SEQ ID NO 28
<211> LENGTH: 47
<212> TYPE: DNA
<213> ORGANISM: Artificial Sequence
<220> FEATURE:
<223> OTHER INFORMATION: hMYC3 Forward Sequence
<220> FEATURE:
<221> NAME/KEY: misc_feature
<222> LOCATION: (23)..(27)
<223> OTHER INFORMATION: any nucleotide sequence of any length (e.g.,
      barcode sequence)

<400> SEQUENCE: 28
ctacacgacg ctcttccgat ctnnnnntac tgcgacgagg aggagaa                 47

<210> SEQ ID NO 29
<211> LENGTH: 47
<212> TYPE: DNA
<213> ORGANISM: Artificial Sequence
<220> FEATURE:
<223> OTHER INFORMATION: hMYC4 Forward Sequence
<220> FEATURE:
<221> NAME/KEY: misc_feature
<222> LOCATION: (23)..(27)
<223> OTHER INFORMATION: any nucleotide sequence of any length (e.g.,
      barcode sequence)

<400> SEQUENCE: 29
```
ctacacgacg ctcttccgat ctnnnnncag gactgtatgt ggagcgg            47

<210> SEQ ID NO 30
<211> LENGTH: 42
<212> TYPE: DNA
<213> ORGANISM: Artificial Sequence
<220> FEATURE:
<223> OTHER INFORMATION: hMYC1 Reverse Sequence

<400> SEQUENCE: 30
cagacgtgtg ctcttccgat cttattcgct ccggatctcc ct                 42

<210> SEQ ID NO 31
<211> LENGTH: 42
<212> TYPE: DNA
<213> ORGANISM: Artificial Sequence
<220> FEATURE:
<223> OTHER INFORMATION: hMYC2 Reverse Sequence

<400> SEQUENCE: 31
cagacgtgtg ctcttccgat ctcctttcag agaagcgggt cc                 42

<210> SEQ ID NO 32
<211> LENGTH: 42
<212> TYPE: DNA
<213> ORGANISM: Artificial Sequence
<220> FEATURE:
<223> OTHER INFORMATION: hMYC3 Reverse Sequence

<400> SEQUENCE: 32
cagacgtgtg ctcttccgat ctcgaaggga gaagggtgtg ac                 42

<210> SEQ ID NO 33
<211> LENGTH: 42
<212> TYPE: DNA
<213> ORGANISM: Artificial Sequence
<220> FEATURE:
<223> OTHER INFORMATION: hMYC4 Reverse Sequence

<400> SEQUENCE: 33
cagacgtgtg ctcttccgat ctggtacaag ctggaggtgg ag                 42

<210> SEQ ID NO 34
<211> LENGTH: 20
<212> TYPE: DNA
<213> ORGANISM: Artificial Sequence
<220> FEATURE:
<223> OTHER INFORMATION: Rsrp1 (a) Forward Sequence

<400> SEQUENCE: 34
aagtacaggc gctactcacg                                          20

<210> SEQ ID NO 35
<211> LENGTH: 20
<212> TYPE: DNA
<213> ORGANISM: Artificial Sequence
<220> FEATURE:
<223> OTHER INFORMATION: Rsrp1 (b) Forward Sequence

<400> SEQUENCE: 35
aagatccaga accaggtcgc                                          20

<210> SEQ ID NO 36
<211> LENGTH: 20
<212> TYPE: DNA

<213> ORGANISM: Artificial Sequence
<220> FEATURE:
<223> OTHER INFORMATION: Rsrp1 (c) Forward Sequence

<400> SEQUENCE: 36
tccttggaca gctaggggat                                        20

<210> SEQ ID NO 37
<211> LENGTH: 20
<212> TYPE: DNA
<213> ORGANISM: Artificial Sequence
<220> FEATURE:
<223> OTHER INFORMATION: Rsrp1 (d) Forward Sequence

<400> SEQUENCE: 37 gagggtttg tgtccagcat                                         20

<210> SEQ ID NO 38
<211> LENGTH: 21
<212> TYPE: DNA
<213> ORGANISM: Artificial Sequence
<220> FEATURE:
<223> OTHER INFORMATION: Hist1h1d (a) Forward Sequence

<400> SEQUENCE: 38
aagaaggcag caaagagtcc a                                      21

<210> SEQ ID NO 39
<211> LENGTH: 20
<212> TYPE: DNA
<213> ORGANISM: Artificial Sequence
<220> FEATURE:
<223> OTHER INFORMATION: Hist1h1d (b) Forward Sequence

<400> SEQUENCE: 39
aagcctaaga aggcgactgg                                        20

<210> SEQ ID NO 40
<211> LENGTH: 19
<212> TYPE: DNA
<213> ORGANISM: Artificial Sequence
<220> FEATURE:
<223> OTHER INFORMATION: ACTB Forward Sequence

<400> SEQUENCE: 40
ggcatgggtc agaaggatt                                         19

<210> SEQ ID NO 41
<211> LENGTH: 20
<212> TYPE: DNA
<213> ORGANISM: Artificial Sequence
<220> FEATURE:
<223> OTHER INFORMATION: DHX9 Forward Sequence

<400> SEQUENCE: 41
ccgattcctc catgcgagtt                                        20

<210> SEQ ID NO 42
<211> LENGTH: 20
<212> TYPE: DNA
<213> ORGANISM: Artificial Sequence
<220> FEATURE:
<223> OTHER INFORMATION: ASXL1 (Pair 1) Forward Sequence

<400> SEQUENCE: 42
tcggatgctc caatgacacc                                        20

<210> SEQ ID NO 43
<211> LENGTH: 21
<212> TYPE: DNA
<213> ORGANISM: Artificial Sequence
<220> FEATURE:
<223> OTHER INFORMATION: ASXL1 (Pair 2) Forward Sequence

<400> SEQUENCE: 43
accaggcccc ttcatcttaa t                                        21

<210> SEQ ID NO 44
<211> LENGTH: 19
<212> TYPE: DNA
<213> ORGANISM: Artificial Sequence
<220> FEATURE:
<223> OTHER INFORMATION: ASXL1 (Pair 3) Forward Sequence

<400> SEQUENCE: 44
gaagccccgg cttgaagat                                           19

<210> SEQ ID NO 45
<211> LENGTH: 20
<212> TYPE: DNA
<213> ORGANISM: Artificial Sequence
<220> FEATURE:
<223> OTHER INFORMATION: ASXL1 (Pair 4) Forward Sequence

<400> SEQUENCE: 45
atcctcaccg actgattgcc                                          20

<210> SEQ ID NO 46
<211> LENGTH: 20
<212> TYPE: DNA
<213> ORGANISM: Artificial Sequence
<220> FEATURE:
<223> OTHER INFORMATION: ASXL1 (Pair 5) Forward Sequence

<400> SEQUENCE: 46
tgcattgcct ggggatttga                                          20

<210> SEQ ID NO 47
<211> LENGTH: 20
<212> TYPE: DNA
<213> ORGANISM: Artificial Sequence
<220> FEATURE:
<223> OTHER INFORMATION: Rsrp1 (a) Reverse Sequence

<400> SEQUENCE: 47
gacggcgact tgtagtacct                                          20

<210> SEQ ID NO 48
<211> LENGTH: 20
<212> TYPE: DNA
<213> ORGANISM: Artificial Sequence
<220> FEATURE:
<223> OTHER INFORMATION: Rsrp1 (b) Reverse Sequence

<400> SEQUENCE: 48
gcagtggctt tgctacggaa                                          20

<210> SEQ ID NO 49
<211> LENGTH: 20
<212> TYPE: DNA
<213> ORGANISM: Artificial Sequence
<220> FEATURE:

<223> OTHER INFORMATION: Rsrp1 (c) Reverse Sequence

<400> SEQUENCE: 49
cacgaatacc cgactcctgt                                       20

<210> SEQ ID NO 50
<211> LENGTH: 20
<212> TYPE: DNA
<213> ORGANISM: Artificial Sequence
<220> FEATURE:
<223> OTHER INFORMATION: Rsrp1 (d) Reverse Sequence

<400> SEQUENCE: 50
acctcaacca tgaacgtccc                                       20

<210> SEQ ID NO 51
<211> LENGTH: 21
<212> TYPE: DNA
<213> ORGANISM: Artificial Sequence
<220> FEATURE:
<223> OTHER INFORMATION: Hist1h1d (a) Reverse Sequence

<400> SEQUENCE: 51
agattttcaa agcaggacgc a                                     21

<210> SEQ ID NO 52
<211> LENGTH: 20
<212> TYPE: DNA
<213> ORGANISM: Artificial Sequence
<220> FEATURE:
<223> OTHER INFORMATION: Hist1h1d (b) Reverse Sequence

<400> SEQUENCE: 52
tctacttctt gcgaggggca                                       20

<210> SEQ ID NO 53
<211> LENGTH: 20
<212> TYPE: DNA
<213> ORGANISM: Artificial Sequence
<220> FEATURE:
<223> OTHER INFORMATION: ACTB Reverse Sequence

<400> SEQUENCE: 53
cacacgcagc tcattgtaga                                       20

<210> SEQ ID NO 54
<211> LENGTH: 20
<212> TYPE: DNA
<213> ORGANISM: Artificial Sequence
<220> FEATURE:
<223> OTHER INFORMATION: DHX9 Reverse Sequence

<400> SEQUENCE: 54
tctggccttc taccgagaca                                       20

<210> SEQ ID NO 55
<211> LENGTH: 21
<212> TYPE: DNA
<213> ORGANISM: Artificial Sequence
<220> FEATURE:
<223> OTHER INFORMATION: ASXL1 (Pair 1) Reverse Sequence

<400> SEQUENCE: 55
ccttctgcct ctatgacctg c                                     21

```
<210> SEQ ID NO 56
<211> LENGTH: 20
<212> TYPE: DNA
<213> ORGANISM: Artificial Sequence
<220> FEATURE:
<223> OTHER INFORMATION: ASXL1 (Pair 2) Reverse Sequence

<400> SEQUENCE: 56
tcccaagctt acagcaggtt                                              20

<210> SEQ ID NO 57
<211> LENGTH: 20
<212> TYPE: DNA
<213> ORGANISM: Artificial Sequence
<220> FEATURE:
<223> OTHER INFORMATION: ASXL1 (Pair 3) Reverse Sequence

<400> SEQUENCE: 57
tgtggctttt cggtgtgaac                                              20

<210> SEQ ID NO 58
<211> LENGTH: 20
<212> TYPE: DNA
<213> ORGANISM: Artificial Sequence
<220> FEATURE:
<223> OTHER INFORMATION: ASXL1 (Pair 4) Reverse Sequence

<400> SEQUENCE: 58
catgagccac caagccctaa                                              20

<210> SEQ ID NO 59
<211> LENGTH: 20
<212> TYPE: DNA
<213> ORGANISM: Artificial Sequence
<220> FEATURE:
<223> OTHER INFORMATION: ASXL1 (Pair 5) Reverse Sequence

<400> SEQUENCE: 59
ctcgagatgg cacagtccag                                              20
```